United States Patent
Pulé et al.

(10) Patent No.: US 11,058,722 B2
(45) Date of Patent: Jul. 13, 2021

(54) CHIMERIC ANTIGEN RECEPTOR COMPRISING A CARTILAGE-OLIGOMERIC MATRIX PROTEIN (COMP) COILED-COIL SPACER DOMAIN

(71) Applicant: AUTOLUS LIMITED, London (GB)

(72) Inventors: Martin Pulé, London (GB); Shaun Cordoba, London (GB)

(73) Assignee: AUTOLUS LIMITED, London (GB)

( * ) Notice: Subject to any disclaimer, the term of this patent is extended or adjusted under 35 U.S.C. 154(b) by 0 days.

(21) Appl. No.: 15/560,558

(22) PCT Filed: Mar. 22, 2016

(86) PCT No.: PCT/GB2016/050795
§ 371 (c)(1),
(2) Date: Sep. 22, 2017

(87) PCT Pub. No.: WO2016/151315
PCT Pub. Date: Sep. 29, 2016

(65) Prior Publication Data
US 2018/0050065 A1    Feb. 22, 2018

(30) Foreign Application Priority Data
Mar. 23, 2015    (GB) ..................................... 1504840

(51) Int. Cl.
*A61K 35/17*    (2015.01)
*C07K 14/705*    (2006.01)

(52) U.S. Cl.
CPC ............ *A61K 35/17* (2013.01); *C07K 14/705* (2013.01); *C07K 2319/00* (2013.01); *C07K 2319/03* (2013.01)

(58) Field of Classification Search
None
See application file for complete search history.

(56) References Cited

U.S. PATENT DOCUMENTS

| 2006/0074230 | A1 | 4/2006 | Koh | |
| 2014/0056892 | A1* | 2/2014 | Noelle | A61K 39/39558 424/134.1 |

FOREIGN PATENT DOCUMENTS

| CN | 103145849 A | 6/2013 | |
| KR | 20110089015 | * 8/2011 | C07K 14/705 |
| WO | WO-2010/102518 A1 | 9/2010 | |
| WO | WO-2014/039523 A1 | 3/2014 | |
| WO | WO-2014/127261 A1 | 8/2014 | |
| WO | WO-2015095895 A1 | * 6/2015 | A61K 35/17 |
| WO | WO-2015/105522 A1 | 7/2015 | |
| WO | WO-2016/030691 A1 | 3/2016 | |
| WO | WO-2017/216561 A1 | 12/2017 | |

OTHER PUBLICATIONS

Malashkevich et al. (Science 1996 274: 761-765), (Year: 1996).*
COMP_Human (P49747.2 Oct. 14, 2008 https://www.ncbi.nlm.nih.gov/protein/209572601?sat=11&satkey=8715899) (Year: 2008).*
Hegde et al. (Molecular Therapy Nov. 2013 21(11): 2087-2101), (Year: 2013).*
Bitra et al. (J. Biol. Chem 2018 293 (26):9958-9969) (Year: 2018).*
Kim et al. (Immune Network Aug. 2011 11(4): 216-222), (Year: 2011).*
Anurathapan et al., Kinetics of tumor destruction by chimeric antigen receptor-modified T cells. *Mol. Ther.* 22(3): 623-33 (2014).
Baskar et al., Targeting malignant B cells with an immunotoxin against ROR1. *MAbs*, 4(3): 349-61 (2012).
Boross et al., Anti-tumor activity of human IgG1 anti-gp75 TA99 mAb against B16F10 melanoma in human FcgammaR1 transgenic mice. *Immunol. Lett.* 160(2): 151-7 (2014).
Carpenter et al., B-cell maturation antigen is a promising target for adoptive T-cell therapy of multiple myeloma. *Clin Cancer Res.* 19(8): 2048-60 (2013).
Chang et al., A general method for facilitating heterodimeric pairing between two proteins: Application to expression of alpha and beta T-cell receptor extracellular segments. *Proc. Natl. Acad. Sci. USA*, 91: 11408-12 (1994).
Donnelly et al., The 'cleavage' activities of foot-and-mouth disease virus 2A site-directed mutants and naturally occurring '2A-like' sequences. *J. Gen. Virol.* 82: 1027-41 (2001).
Guest et al., The role of extracellular spacer regions in the optimal design of chimeric immune receptors—Evaluation of four different scFvs and antigens. *J. Immunother.* 28(3): 203-11 (2005).
Hudecek et al., The nonsignaling extracellular spacer domain of chimeric antigen receptors in decisive for in vivo antitumor activity. *Cancer Immunol. Res.* 3(2): 125-35 (2014).
James et al., Mathematical modeling of chimeric TCR triggering predicts the magnitude of target lysis and its impairment by TCR downmodulation. *J. Immunol.* 184(8): 4284-94 (2010).
Liu et al., A seven-helix coiled coil. *Proc. Natl. Acad. Sci. USA*, 103: 15457-62 (2006).
Lupas et al., The structure of alpha-helical coiled coils. *Adv. Protein Chem.* 70: 37-8 (2007).
Mahrenholz et al., Complex networks govern coiled-coil oligomerization—predicting and profiling by means of a machine learning approach. *Mol. Cell. Proteomics*, 10(5): M110.004994 (2011).
Rossi et al., Stably tethered multifunctional structures of defined composition made by the dock and lock method for use in cancer targeting. *Pros. Natl. Acad. Sci. USA*; 103(18): 6841-6 (2006).
Sadelain et al., The basic principles of chimeric antigen receptor design. *Cancer Discov.* 3(4): 388-98 (2013).
Tai et al., Novel anti-B-cell maturation antigen antibody-drug conjugate (GSK2857916) selectively induces killing of multiple myeloma. *Blood*, 123(20): 3128-38 (2014).

(Continued)

*Primary Examiner* — Peter J Reddig
(74) *Attorney, Agent, or Firm* — Marshall, Gerstein & Borun LLP

(57) ABSTRACT

The present invention provides a chimeric antigen-receptor (CAR)-forming polypeptide comprising: (i) an antigen-binding domain; (ii) a coiled-coil spacer domain; (iii) a transmembrane domain; and (iv) an endodomain. The invention also provides a multimeric CAR formed by association of a plurality of CAR-forming polypeptides by virtue of association of their coiled-coil spacer domains.

13 Claims, 20 Drawing Sheets

Specification includes a Sequence Listing.

(56) References Cited

OTHER PUBLICATIONS

Yang et al., Therapeutic potential and challenges of targeting receptor tyrosine kinase ROR1 with monoclonal antibodies in B-cell malignancies. *PLoS One*, 6(6): e21018 (2011).

Zaccai et al., A de novo peptide hexamer with a mutable channel. *Nat. Chem. Biol.* 7: 935-41 (2011).

Ahmad et al., "Revisiting ligand-induced conformational changes in proteins: essence, advancements, implications and future challenges," Journal of Biomolecular Structure and Dynamics 31(6):630-648 (2013).

Bridgeman et al., "The optimal antigen response of chimeric antigen receptors harboring the CD3? transmembrane domain is dependent upon incorporation of the receptor into the endogenous TCR/CD3 complex," The Journal of Immunology 184(12):6938-6949 (2010).

Dodge et al., "Production of cartilage oligomeric matrix protein (COMP) by cultured human dermal and synovial fibroblasts," Osteoarthritis and Cartilage 6:435-440 (1998).

Golden et al., "High-level production of a secreted, heterodimeric αβ murine T-cell receptor in *Escherichia coli*," J of Immunological Methods 206:163-169 (1997).

Holden et al., "Secretion of Cartilage Oligomeric Matrix Protein Is Affected by the Signal Peptide," The Journal of Biological Chemistry 280(17):17172-17179 (2005).

Hudecek et al., "Receptor Affinity and Extracellular Domain Modifications Affect Tumor Recognition by ROR1-Specific Chimeric Antigen Receptor T Cells," Clinical Cancer Research 19(12):3153-3164 (2013).

International Search Report and Written Opinion from International Application No. PCT/GB2016/050795 dated May 30, 2016.

Irving et al., "The cytoplasmic domain of the T cell receptor ζ chain is sufficient to coule to receptor-associated signal transduction pathways," Cell 64(5):891-901 (1991).

Künkele et al., "Functional Tuning of CARs Reveals Signaling Threshold above Which CD8+ CTL Antitumor Potency Is Attenuated due to Cell Fas-FasL-Dependent AICD," Cancer Immunol Res 3(4):368-379 (2015).

Likar et al., "Use of human deoxycitidine kinase mutant variant as a reporter gene for evaluation of adoptive T-cell therapy," Onkologii Immunopatologii Pediatrii, 11(2):23-31 (2012).

Shi et al., "Chimeric antigen receptor for adoptive immunotherapy of cancer: latest research and future prospects," Molecular Cancer 13:219, 8 pages (2014).

Surette et al,. "Role of α-Helical Coiled-coil Interactions in Receptor Dimerization, Signaling, and Adaptation during Bacterial Chemotaxis", Journal of Biological Chemistry, 271(30):17966-7973 (1996).

Burns et al., "A High Molecular Weight Melanoma-Associated Antigen-Specific Chimeric Antigen Receptor Redirects Lymphocytes to Target Human Melanomas," Cancer Res; 70(8):3027-3033 (2010).

Chen et al., "Fusion Protein Linkers: Property, Design and Functionality," Adv Drug Deliv Rev, 65(10):1357-1369 (2013).

Courtney et al., "TCR Signaling: Mechanisms of Initiation and Propagation," Trends Biochem Sci., 43(2):108-123 (2018).

Dolezal et al., "ScFv multimers of the anti-neuraminidase antibody NC10: shortening of the linker in a single-chain Fv fragment assembled in $V_L$ to $V_H$ orientation drives the formation of dimers, trimers, tetramers and higher molecular mass multimers," Protein Engineering,13(8):565-574 (2000).

Guedan et al., "Enhancing CAR T cell persistence through ICOS and 4-1BB costimulation," JCI Insight: 3(1):1-17 (2018).

Guha et al., "Frontline Science: Functionally impaired geriatric CAR-T cells rescued by increased alpha5beta1 integrin expression," Journal of Leukocyte Biology, 102:201-208 (2017).

Hege et al., "Safety, tumor trafficking and immunogenicity of chimeric antigen receptor (CAR)-T cells specific for TAG-72 in colorectal cancer," Journal for ImmunoTherapy of Cancer, 5:22, pp. 1-14 (2017).

Long et al., "4-1BB Costimulation Ameliorates T Cell Exhaustion Induced by Tonic Signaling of Chimeric Antigen Receptors," Nat Med.; 21(6) 581-590 (2015).

Maeda et al., "Engineering of Functional Chimeric Protein G-Vargula Luciferase," Analytical Biochemistry 249, Article No. AB972181, 147-152 (1997).

Maus et al., "T Cells Expressing Chimeric Antigen Receptors Can Cause Anaphylaxis in Humans," Cancer Immunol Res: 1(1):26-31 (2013).

Richman et al., "High-Affinity GD2-Specific CAR T Cells Induce Fatal Encephalitis in a Preclinical Neuroblastoma Model," Cancer Immunol Res: 6(1):36-46 (2018).

Schamel et al., "The TCE is an allosterically regulated macromolecular machinery changing its conformation while working," Immunological Reviews 291:8-25 (2019).

Teplyakov et al., "Antibody modeling assessment II. Structures of models," Proteins 82:1563-1582 (2014).

Turtle et al., "CD19 CAR-T cells of defined $CD4^+$:$CD8^+$ composition in adult B cell ALL patients," J. Clin Invest. 126(6):2123-2138 (2016).

Arndt et al., "Helix-stabilized Fv (hsFv) Antibody Fragments: Substituting the Constant Domains of a Fab Fragment for a Heterodimeric Coiled-coil Domain," J. Mol. Biol. 312:221-228 (2001).

Cordoba et al., "The large ectodomains of CD45 and CD148 regulate their segregation from and inhibition of ligated T-cell receptor," Blood 121(21):4295-4302 (2013).

Jones et al., "Lentirival Vector Design for Optimal T Cell Receptor Gene Expression in the Transduction of Peripheral Blood Lymphocytes and Tumor-Infiltrating Lymphocytes," Human Gene Therapy 20:630-640 (2009).

Lee et al., "Designing APRIL-Based Therapeutics for Targeting BCMA in Multiple Myeloma," Abstract, 22(1):S104 (2014).

Szatrowski et al., "Lineage Specific Treatment of Adult Patients with Acute Lymphoblastic Leukemia in first Remission with Anti-B4-Blocked Ricin or High-Dose Cytarabine," Cancer 97(6):1471-1480 (2003).

GenBank AAB86501.1, COMP_HUMAN [*Homo sapiens*], Nov. 18, 1997.

\* cited by examiner

A)

B)

Modified from prior art Andrei N. Lupas and Markus Gruber; Adv Protein Chem. 2005; 70:37-78

A)

- Binder domains
- Coiled coil
- Disulphide bonds
- Transmembrane
- Intracellular signalling domain

B)

anti-CD33 COMP CAR:

Control anti-CD33 IgG1 CAR:

anti-ROR-1 COMP CAR:

Control anti-ROR-1 IgG1 CAR:

Amino acid sequence of the coiled coil anti-CD33 COMP CAR (SEQ ID No. 26):

MGTSLLCWMALCLLGADHADACPYSNPSLCSGGGGSELPTQGTFSNVSTNVSPAKPTTTACPYSNPSLCSGGGGSPAPRPPTPAPTIASQ
PLSLRPEACRPAAGGAVHTRGLDFACDIYIWAPLAGTCGVLLLSLVITLYCNHRNRRRVCKCPRPVVRAEGRGSLLTCGDVEENPGPMAVP
TQVLGLLLLWLTDARCDIQMTQSPSSLSASVGDRVTITCRASEDIYFNLVWYQQKPGKAPKLLIYDTNRLADGVPSRFSGSGSGTQYTLTISS
LQPEDFATYYCQHYKNYPLTFGQGTKLEIKRSGGGGSGGGGSGGGGSGGGGSRSEVQLVESGGGLVQPGGSLRLSCAASGFTLSNYGMH
WIRQAPGKGLEWVSSISLNGGSTYYRDSVKGRFTISRDNAKSTLYLQMNSLRAEDTAVYYCAAQDAYTGGYFDYWGQGTLVTVSSMDPA
GSDLGPQMLRELQETNAALQDVRELLRQQVREITFLKNTVMECDACGSGKKDPKFWVLVVVGGVLACYSLLVTVAFIIFWVRSRVKFSRS
ADAPAYQQGQNQLYNELNLGRREEYDVLDKRRGRDPEMGGKPRRKNPQEGLYNELQKDKMAEAYSEIGMKGERRRGKGHDGLYQGL
STATKDTYDALHMQALPPR

Amino acid sequence of the coiled coil anti-ROR-1 COMP CAR(SEQ ID No. 27):

MGTSLLCWMALCLLGADHADACPYSNPSLCSGGGGSELPTQGTFSNVSTNVSPAKPTTTACPYSNPSLCSGGGGSPAPRPPTPAPTIASQPLS
LRPEACRPAAGGAVHTRGLDFACDIYIWAPLAGTCGVLLLSLVITLYCNHRNRRRVCKCPRPVVRAEGRGSLLTCGDVEENPGPMETDTLLLW
VLLLWVPGSTGQSVKESEGDLVTPAGNLTLTCTASGSDINDYPISWVRQAPGKGLEWIGFINSGGSTWYASWVKGRFTISRTSTTVDLKMTSL
TTDDTATYFCARGYSTYYGDFNIWGPGTLVTISSGGGGSGGGGSGGGGSELVMTQTPSSTSGAVGGTVTINCQASQSIDSNLAWFQQKPGQ
PPTLLIYRASNLASGVPSRFSGSRSGTEYTLTISGVQREDAATYYCLGGVGNVSYRTSFGGGTEVVVKRSDPAGSDLGPQMLRELQETNAALQD
VRELLRQQVREITFLKNTVMECDACGSGKKDPKFWVLVVVGGVLACYSLLVTVAFIIFWVRSRVKFSRSADAPAYQQGQNQLYNELNLGRREE
YDVLDKRRGRDPEMGGKPRRKNPQEGLYNELQKDKMAEAYSEIGMKGERRRGKGHDGLYQGLSTATKDTYDALHMQALPPR

FIGURE 5 – CONT.

D) DNA sequence of the coiled coil anti-CD33 COMP CAR (SEQ ID No. 28):

```
ATGGGCACCAGCCTGCTGTGCTGGATGGCCCTGTGCCTGCTGGGCGCCGACCACGCCGATGCCTGCCCCTACAGCAACCCCAGCC
TGTGCAGCGGAGGCGGCGGCAGCGAGCTGCCCACCCAGGGCACCTTCTCCAACGTGTCCACCAACGTGAGCCCAGCCAAGCCCA
CCACCACCGCCTGTCCTTATTCCAATCCTTCCCTGTGTAGCGGAGGGGGAGGCAGCCCAGCCCCCAGACCTCCCACCCCAGCCCCC
ACCATCGCCAGCCAGCCTCTGAGCCTGAGACCCGAGGCCTGCCGCCCAGCCGCCGGCGGCGCCGTGCACACCAGAGGCCTGGAT
TTCGCCTGCGATATCTACATCTGGGCCCCACTGGCCGGCACCTGTGGCGTGCTGCTGCTGAGCCTGGTGATCACCCTGTACTGCAA
CCACCGCAACCGCAGGCGCGTGTGCAAGTGCCCCAGGCCCGTGGTGAGAGCCGAGGGCAGAGGCAGCCTGCTGACCTGCGGCG
ACGTGGAGGAGAACCCAGGCCCCATGGCCGTGCCCACTCAGGTCCTGGGGTTGTTGCTACTGTGGCTTACAGATGCCAGATGTG
ACATCCAGATGACACAGTCTCCATCTTCCCTGTCTGCATCTGTCGGAGATCGCGTCACCATCACCTGTCGAGCAAGTGAGGACATT
TATTTTAATTTAGTGTGGTATCAGCAGAAACCAGGAAAGGCCCCTAAGCTCCTGATCTATGATACAAATCGCTTGGCAGATGGGG
TCCCATCACGGTTCAGTGGCTCTGGATCTGGCACACAGTATACTCTAACCATAAGTAGCCTGCAACCCGAAGATTTCGCAACCTAT
TATTGTCAACACTATAAGAATTATCCGCTCACGTTCGGTCAGGGGACCAAGCTGGAAATCAAAAGATCTGGTGGCGGAGGGTCA
GGAGGCGGAGGCAGCGGAGGCGGTGGCTCGGGAGGCGGAGGCTCGAGATCTGAGGTGCAGTTGGTGGAGTCTGGGGGCGGC
TTGGTGCAGCCTGGAGGGTCCCTGAGGCTCTCCTGTGCAGCCTCAGGATTCACTCTCAGTAATTATGGCATGCACTGGATCAGGC
AGGCTCCAGGGAAGGGTCTGGAGTGGGTCTCGTCTATTAGTCTTAATGGTGGTAGCACTTACTATCGAGACTCCGTGAAGGGCC
GATTCACTATCTCCAGGGACAATGCAAAAAGCACCCTCTACCTTCAAATGAATAGTCTGAGGGCCGAGGACACGGCCGTCTATTA
CTGTGCAGCACAGGACGCTTATACGGGAGGTTACTTTGATTACTGGGGCCAAGGAACGCTGGTCACAGTCTCGTCTATGGATCCC
GCCGGGAGCGACCTGGGCCCTCAGATGCTGCGGGAGCTGCAGGAGACAAATGCCGCCCTGCAGGACGTGCGCGAGCTGCTGAG
ACAGCAGGTGCGGGAGATTACATTCCTGAAGAACACCGTGATGGAGTGCGATGCCTGCGGATCTGGGAAGAAGGACCCCAAGT
TCTGGGTCCTGGTGGTGGTGGGAGGCGTGCTGGCCTGTTACTCTCTCCTGGTGACCGTGGCCTTCATCATCTTTTGGGTGCGCTCC
CGGGTGAAGTTTTCTCGCTCTGCCGATGCCCCAGCCTATCAGCAGGGCCAGAATCAGCTGTACAATGAACTGAACCTGGGCAGGC
GGGAGGAGTACGACGTGCTGGATAAGCGGAGAGGCAGAGACCCCGAGATGGGCGGCAAACCACGGCGCAAAAATCCCCAGGA
GGGACTCTATAACGAGCTGCAGAAGGACAAAATGGCCGAGGCCTATTCCGAGATCGGCATGAAGGGAGAGAGAAGACGCGGA
AAGGGCCACGACGGCCTGTATCAGGGATTGTCCACCGCTACAAAAGATACATATGATGCCCTGCACATGCAGGCCCTGCCACCCA
GATGA
```

DNA sequence of the coiled coil anti-ROR-1 COMP CAR (SEQ ID No. 29):

```
ATGGGCACCAGCCTGCTGTGCTGGATGGCCCTGTGCCTGCTGGGCGCCGACCACGCCGATGCCTGCCCCTACAGCAACCCCAGCCTGT
GCAGCGGAGGCGGCGGCAGCGAGCTGCCCACCCAGGGCACCTTCTCCAACGTGTCCACCAACGTGAGCCCAGCCAAGCCCACCACCA
CCGCCTGTCCTTATTCCAATCCTTCCCTGTGTAGCGGAGGGGGAGGCAGCCCAGCCCCCAGACCTCCCACCCCAGCCCCCACCATCGCC
AGCCAGCCTCTGAGCCTGAGACCCGAGGCCTGCCGCCCAGCCGCCGGCGGCGCCGTGCACACCAGAGGCCTGGATTTCGCCTGCGAT
ATCTACATCTGGGCCCCACTGGCCGGCACCTGTGGCGTGCTGCTGCTGAGCCTGGTGATCACCCTGTACTGCAACCACCGCAACCGCA
GGCGCGTGTGCAAGTGCCCCAGGCCCGTGGTGAGAGCCGAGGGCAGAGGCAGCCTGCTGACCTGCGGCGACGTGGAGGAGAACCC
AGGCCCCATGGAGACCGACACCCTGCTGCTGTGGGTGCTGCTGCTGTGGGTGCCCGGCAGCACCGGCCAGAGCGTGAAGGAGAGCG
AGGGCGACCTGGTGACCCCAGCCGGCAACCTGACCCTGACCTGCACCGCCAGCGGCAGCGACATCAACGACTACCCCATCAGCTGGG
TGCGGCAGGCCCCAGGCAAGGGCCTGGAGTGGATCGGCTTCATCAACAGCGGCGGCAGCACCTGGTACGCCAGCTGGGTGAAGGGC
CGGTTCACCATCAGCCGGACCAGCACCACCGTGGACCTGAAGATGACCAGCCTGACCACCGACGACACCGCCACCTACTTCTGCGCCA
GAGGCTACAGCACCTACTACGGCGACTTCAACATCTGGGGACCCGGCACCCTGGTGACCATCAGCAGCGGAGGCGGAGGGTCTGGG
GGCGGCGGTAGCGGCGGAGGAGGGAGCGAGCTGGTGATGACCCAGACCCCAAGCAGCACCAGCGGCGCCGTGGGCGGCACCGTGA
CCATCAACTGCCAGGCCAGCCAGAGCATCGACAGCAACCTGGCCTGGTTCCAGCAGAAGCCTGGCCAGCCACCCACCCTGCTGATCTA
CCGGGCCAGCAACCTGGCCAGCGGCGTGCCCAGCCGGTTCAGCGGCAGCCGGAGCGGCACCGAGTACACCCTGACCATCAGCGGCG
TGCAGCGGGAGGACGCCGCCACCTACTACTGCCTGGGCGGAGTGGGCAACGTGAGCTACCGGACCAGCTTCGGCGGAGGCACCGAG
GTGGTGGTGAAGCGGTCGGATCCCGCCGGGAGCGACCTGGGCCCTCAGATGCTGCGGGAGCTGCAGGAGACAAATGCCGCCCTGCA
GGACGTGCGCGAGCTGCTGAGACAGCAGGTGCGGGAGATTACATTCCTGAAGAACACCGTGATGGAGTGCGATGCCTGCGGATCTG
GGAAGAAGGACCCCAAGTTCTGGGTCCTGGTGGTGGTGGGAGGCGTGCTGGCCTGTTACTCTCTCCTGGTGACCGTGGCCTTCATCAT
CTTTTGGGTGCGCTCCCGGGTGAAGTTTTCTCGCTCTGCCGATGCCCCAGCCTATCAGCAGGGCCAGAATCAGCTGTACAATGAACTG
AACCTGGGCAGGCGGGAGGAGTACGACGTGCTGGATAAGCGGAGAGGCAGAGACCCCGAGATGGGCGGCAAACCACGGCGCAAAA
ATCCCCAGGAGGGACTCTATAACGAGCTGCAGAAGGACAAAATGGCCGAGGCCTATTCCGAGATCGGCATGAAGGGAGAGAGAAGA
CGCGGAAAGGGCCACGACGGCCTGTATCAGGGATTGTCCACCGCTACAAAAGATACATATGATGCCCTGCACATGCAGGCCCTGCCA
CCCAGA
```

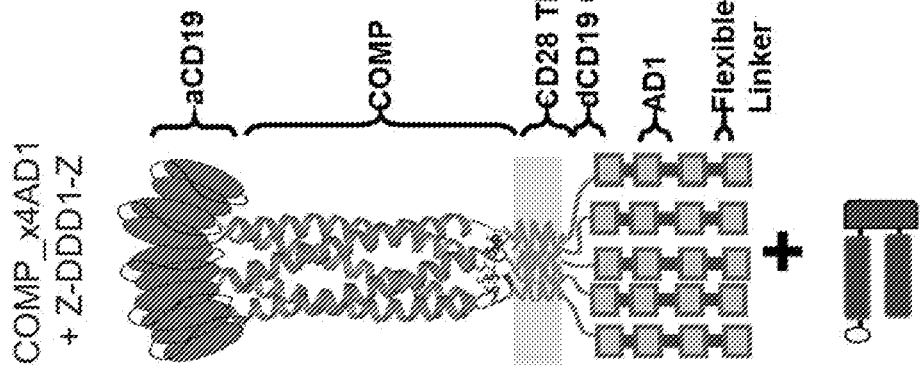
FIGURE 15
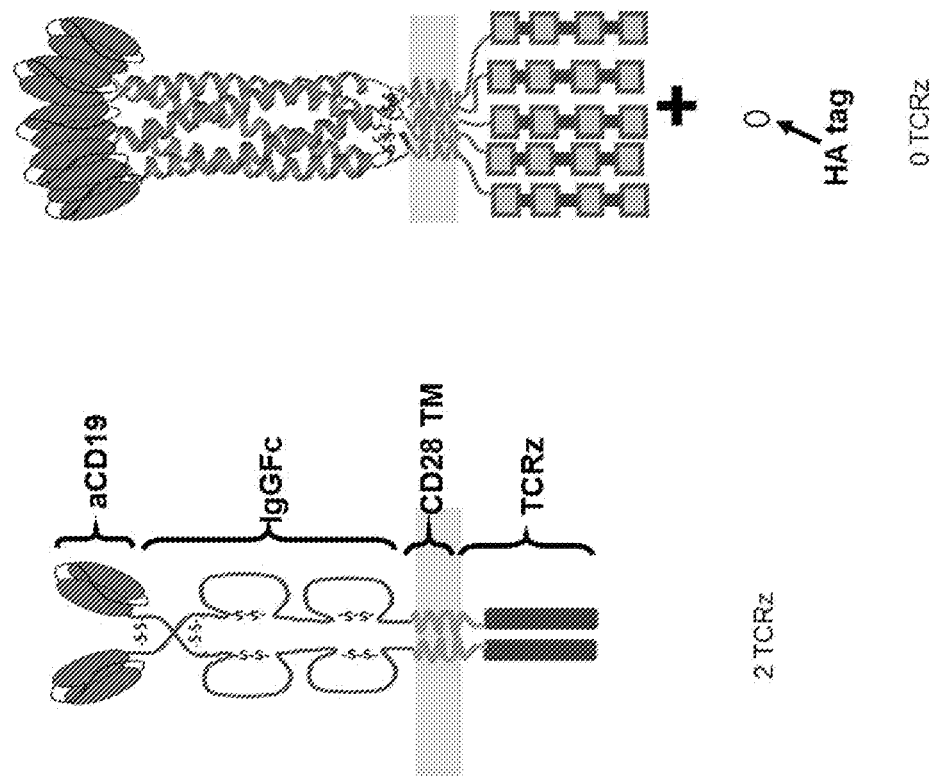

CHIMERIC ANTIGEN RECEPTOR COMPRISING A CARTILAGE-OLIGOMERIC MATRIX PROTEIN (COMP) COILED-COIL SPACER DOMAIN

CROSS-REFERENCE TO RELATED APPLICATION

This application is a U.S. National Phase of International Application No. PCT/GB2016/050795 filed Mar. 22, 2016, which claims priority from Application 1504840.8 filed on Mar. 23, 2015 in the United Kingdom.

INCORPORATION BY REFERENCE OF MATERIALS SUBMITTED ELECTRONICALLY

This application contains, as a separate part of the disclosure, a Sequence Listing in computer readable form (Filename: 52306 SubSeqlisting.txt; Size: 40,968 bytes; Created: Nov. 12, 2020), which is incorporated by reference in its entirety.

FIELD OF THE INVENTION

The present invention relates to a chimeric antigen receptor (CAR), comprising a particular spacer domain which causes the formation of multimeric CAR molecules at the cell surface. The multimeric CAR molecule may be "supersensitive" and capable of inducing T-cell activation in response to binding an antigen which is expressed at low density of a target cell.

BACKGROUND TO THE INVENTION

Chimeric Antigen Receptors (CARs)

Traditionally, antigen-specific T-cells have been generated by selective expansion of peripheral blood T-cells natively specific for the target antigen. However, it is difficult and quite often impossible to select and expand large numbers of T-cells specific for most cancer antigens. Gene-therapy with integrating vectors affords a solution to this problem as transgenic expression of Chimeric Antigen Receptor (CAR) allows generation of large numbers of T cells specific to any surface antigen by ex vivo viral vector transduction of a bulk population of peripheral blood T-cells.

Chimeric antigen receptors are proteins which graft the specificity of an antigen binder, such as a monoclonal antibody (mAb), to the effector function of a T-cell. Their usual form is that of a type I transmembrane domain protein with an antigen recognizing amino terminus, a spacer, a transmembrane domain all connected to a compound endodomain which transmits T-cell survival and activation signals (see FIG. 1A).

The most common forms of these molecules are fusions of single-chain variable fragments (scFv) derived from monoclonal antibodies which recognize a target antigen, fused via a spacer and a transmembrane domain to a signalling endodomain. Such molecules result in activation of the T-cell in response to recognition by the scFv of its target. When T cells express such a CAR, they recognize and kill target cells that express the target antigen. Several CARs have been developed against tumour associated antigens, and adoptive transfer approaches using such CAR-expressing T cells are currently in clinical trial for the treatment of various cancers.

CARs often comprise a spacer domain to provide an appropriate distance between the antigen-binding domain and the cell membrane and to allow for suitable orientation, reach and segregation from phosphatases upon ligand engagement.

Common spacers used are the Fc of IgG1, the stalk from CD8a and CD28 and even just the IgG1 hinge alone or the ectodomain of CD247 can suffice depending on the antigen (FIG. 2b).

These common spacers are limited because they either must contain whole domain structures in order to form a functional spacer or they are heavily glycosylated and changes in amino acid length would result in unpredictable changes in spacer size. For example IgG spacers must contain whole numbers of immunoglobulin domains. This requirement for a whole number of structural domains means that the alterations that can be made to the spacers are limited.

In addition, the above listed spacers are typically long primary amino acid sequences which fold to form the required secondary and tertiary structures. As such they are typically encoded by long nucleic acid sequences. This requirement for a long nucleic acid sequence is a problem for the construction of vectors encoding the CARs.

Classical CARs have certain design constraints. As a classical CAR is homodimer, there are commonly two (identical) binding specificities and a 1:1 ratio of antigen binding domains to intracellular T-cell signalling domains. This imposes a certain stoichiometry and limits the flexibility of the system as a whole.

There is thus a need for alternative CARs which offer greater flexibility in terms of design.

Affinity Issues

CAR binding domains are usually derived from the variable region of either pre-existing antibody or antibodies selected from a library. As a result, most selected CARs bind cognate ligand with nanomolar affinity. In contrast, the biophysical properties of TCR:peptide:MHC (TCR-pMHC) binding are usually 10-1 uM (orders of magnitude lower in affinity). Although higher affinity interactions increase specificity for a ligand at a given receptor concentration, there is emerging evidence that the TCR has evolved to have a lower affinity so as to allow T-cells to detect target cells that express low density cognate peptide MHC.

It has been reported that a T-cell can be activated by as few as ten cognate pMHC and that one pMHC can trigger a productive signal in up to 200 TCR molecules. This is thought to be achieved through a process known as serial triggering; where one cognate pMHC present on the target cell can go through a cycle of binding, triggering and then dissociating from a TCR multiple times, effectively amplifying the signal. As a consequence, only a low number of cognate pMHC are needed to transduce a productive signal.

The higher affinity of CARs means that the molecular dissociation of an interaction can take minutes to hours, unlike TCR which is typically in the order of seconds. For this reason it is unlikely that CAR signalling undergoes an effective serial triggering response but relies instead on the ligation of higher numbers of receptors. This may limit CARs to target ligands that are expressed on target cells at high density. It has been estimated that a high affinity CAR requires a target cell to express >10 k ligand molecules to elicit an effective killing response. More specifically, using a first generation CAR, James et al. have shown a requirement of ~30,000 target molecules/target cell (inducing endocytosis of ~20,000 CAR molecules) to trigger maximum lytic activity (S. James et al., The Journal of Immunology, vol. 184 (8) 4284-4294, 2010). Animal models indicate that target cells that express ligands below the threshold for killing can escape detection and can re-establish disease (U. Anurathapan et al., Molecular Therapy, vol. 22 (3) 623-633, 2014).

One method to increase CAR sensitivity to low density ligands is to use a low affinity binder domain which can then mimic the TCR-pMHC serial triggering response. However there are several limitations to this approach. The use of a low affinity CAR is currently unpredictable, due to the unknown contribution that co-stimulatory, pseudodimer formation and adhesion molecules play in TCR-pMHC serial triggering responses. In CAR therapy, these molecular interactions vary depending on the target cells and it is therefore difficult to obtain a robust serial triggering response. Furthermore, the methods to reduce the affinity of CARs to be on par with TCR usually involve starting with a high affinity CAR and then mutating the CDRs. This is a lengthy and often unsuccessful approach which can cause unpredictable results and increase the risk of off target binding.

Engineering a CAR that is able to trigger in the presence of low density ligand would allow the therapy to target many more cancers and also reduce the chance of cancer escape.

There is thus a need for CARs which are not associated with the problems outlined above.

SUMMARY OF ASPECTS OF THE INVENTION

In a first aspect the present invention provides a chimeric antigen receptor (CAR)-forming polypeptide comprising:
an antigen-binding domain;
(ii) a coiled-coil spacer domain;
(iii) a transmembrane domain; and
(iv) an endodomain.

The present invention also provides an accessory polypeptide comprising:
(i) a coiled-coil spacer domain;
(iii) a transmembrane domain; and
(iv) an endodomain.

The coiled-coil domain enables the multimerization of a plurality of CAR-forming polypeptides and/or accessory polypeptides, such as at least three CAR-forming polypeptides/accessory polypeptides, to form a multimeric CAR.

The coiled-coil domain may be derived from any of the following: cartilage-oligomeric matrix protein (COMP), mannose-binding protein A, coiled-coil serine-rich protein 1, polypeptide release factor 2, SNAP-25, SNARE, Lac repressor or apolipoprotein E.

The coiled-coil domain may comprise the sequence shown as SEQ ID No. 1 or a fragment thereof, or a variant thereof which has at least 80% sequence identity.

The endodomain may comprise at least one of CD3 zeta endodomain, CD28 endodomain, 41BB endodomain and OX40 endodomain.

The endodomain may comprise the sequence shown as SEQ ID No. 7 or a variant thereof which has at least 80% sequence identity.

The antigen-binding domain may bind an antigen which is expressed at a low density on a target cell. For example, the antigen-binding domain may bind to ROR-1, Typr-1 or BCMA.

The CAR-forming polypeptide may comprise an element capable of forming a bridge with another CAR.

For example, the element may be capable of forming a di-sulphide bridge with another CAR which contains such an element.

The second aspect of the invention relates to multimeric CARs which form due to interactions between the coiled-coil spacer domains or CAR-forming polypeptide(s) and/or accessory polypeptide(s).

In a first embodiment of the second aspect the present invention provides a multimeric chimeric antigen receptor (CAR) comprising a plurality of CAR-forming polypeptides as defined above.

In a second embodiment of the second aspect of the invention there is provided a multimeric chimeric antigen receptor (CAR) comprising one or more CAR-forming polypeptides and one or more accessory polypeptides as defined above.

The CAR-forming polypeptide(s) and/or accessory polypeptide(s) in a multimeric CAR may comprise different endodomains.

If the multimeric CAR comprises two or more CAR-forming polypeptides, they may have different antigen-binding domains, for example antigen-binding domains with different binding specificities.

One of the endodomains of the CAR-forming polypeptide and the accessory polypeptide may comprise a CD3 zeta endodomain and the other endodomain of the CAR-forming polypeptide and the accessory polypeptide may comprise a 41BB endodomain. Where there are two accessory polypeptides, one may comprise the 41BB endodomain and the other may comprise the CD28 endodomain.

The multimeric CAR may, for example, be dimeric, trimeric, tetrameric, pentameric, hexameric or heptameric.

A pentameric CAR may comprise any of the following combinations of CAR-forming polypeptide and accessory polypeptide chains:

| CAR-forming polypeptide | Accessory polypeptide |
|---|---|
| 5 | 0 |
| 4 | 1 |
| 3 | 2 |
| 2 | 3 |
| 1 | 4 |
| 0 | 5 |

Where a multimeric CAR comprises first and second CAR-forming polypeptides according to the first aspect of the invention, the antigen-binding domain of the first CAR may bind to a different epitope than the antigen-binding domain of the second CAR.

In this embodiment, the antigen-binding domain of the first CAR may bind to a different antigen than the antigen-binding domain of the second CAR.

The present invention also provides an engaged complex which comprises at least two multimeric CARs according to the second aspect of the invention, wherein a first CAR on a first multimeric CAR forms a bridge with a second CAR on a second multimeric CAR, such that the first and second multimeric CARs engage to form a complex.

The bridge may be a disulphide bridge or an additional coiled coil structure.

In a third aspect the present invention provides a chimeric antigen receptor (CAR) signalling system, which comprises:
(i) a multimeric CAR comprising a CAR-forming polypeptide or accessory polypeptide as defined above which comprises a first heterodimerization domain; and
(ii) an intracellular signalling component comprising a signalling domain and a second heterodimerization domain;

wherein heterodimerization between the first and second heterodimerization domains causes the multimeric CAR and signalling component to form a functional CAR complex.

The or each CAR-forming polypeptide(s) or accessory polypeptide(s) may comprise a plurality of heterodimerisation domains, such that a single CAR-forming polypeptide or accessory polypeptide is capable of heterodimerising with a plurality of signalling components.

The signalling component of a CAR signalling system may comprise a plurality of signalling domains.

In a fourth aspect the present invention provides a nucleic acid which encodes a CAR-forming polypeptide according to the first aspect of the invention and/or an accessory polypeptide as defined above.

The fifth aspect of the invention relates to nucleic acid constructs which comprise two or more nucleic acid sequences.

In a first embodiment of the fifth aspect of the invention there is provided a nucleic acid construct which encodes two or more CAR forming polypeptides according to the first aspect of the invention.

In a second embodiment of the fifth aspect of the invention there is provided a nucleic acid construct which encodes at least one CAR-forming polypeptide and at least one accessory polypeptide as defined above.

In a first embodiment of the fifth aspect of the invention there is provided a nucleic acid construct which encodes:
(i) at least one CAR-forming polypeptide according to the first aspect of the invention, which forms a multimeric CAR according to the second aspect of the invention; and
(ii) an intracellular signalling component as defined in relation to the fifth aspect of the invention.

In a sixth aspect the present invention provides a vector which comprises a nucleic acid sequence according to the fourth aspect of the invention or a nucleic acid construct according to the fifth aspect of the invention.

The vector may be, for example, a retroviral vector or a lentiviral vector or a transposon.

In a seventh aspect the present invention provides a cell which expresses a CAR-forming polypeptide or accessory polypeptide according to the first aspect of the invention, a multimeric CAR according the second aspect of the present invention, a CAR signalling system according to the third aspect of the invention; or an engaged complex as defined above.

The cell may be a T cell or NK cell.

In an eighth aspect the present invention provides a pharmaceutical composition which comprises a cell according to the seventh aspect of the invention.

In a ninth aspect the present invention relates to a cell according to the seventh aspect of the invention for use in treating a disease.

In a tenth aspect the present invention relates to the use of a cell according to the seventh aspect of the invention in the manufacture of a medicament for treating a disease.

In an eleventh aspect the present invention relates to a method for treating a disease which comprises the step of administering a cell according to the seventh aspect of the invention to a subject.

The disease may be cancer, for example Chronic lymphocytic leukaemia (CLL), melanoma or myeloma.

In a twelfth aspect the present invention relates to a kit which comprises a nucleic acid according to fourth aspect of the invention, a nucleic acid construct according to the fifth aspect of the invention or a vector according to the sixth aspect of the present invention.

In a thirteenth aspect the present invention provides a kit which comprises a cell according to the seventh aspect of the invention.

In a fourteenth aspect the present invention relates to a method for making a cell according to the seventh aspect of the invention, which comprises the step of introducing a nucleic acid according to fourth aspect of the invention, a nucleic acid construct according to the fifth aspect of the invention or a vector according to the sixth aspect of the present invention.

The cell may be from a sample isolated from a subject.

The use of a coiled coil domain as a spacer in a CAR provides a number of advantages over spacers which have been used previously, such as Fc domains derived from IgG.

For example, the use of a coiled coil domain enables the spacer dimensions to be altered in 0.15 nm increments. The addition or subtraction of individual amino acids or a number of amino acids means that the size of the coiled coil spacer can be incrementally altered. In contrast, the use of IgG spacers only allows the addition or removal of whole immunoglobulin domains. This means that the lowest increment of change is ~4 nm (i.e. the size of a folded immunoglobulin domain).

Coiled coil domains are coded by a smaller DNA fragment (e.g ~100 nucleotides) compared to the Fc domain derived from IgG (~700 nucleotides). This allows for a smaller DNA vector which is important for improving viral titre and transduction efficiency.

The use of a coiled coil spacer allows a selection from a large number of coiled coil spacers that will not cross-hybridize with other coiled coil domains. This is in contrast with other spacers where there are a more limited numbers of spacer options.

The use of a coiled coil spacer also much greater flexibility in terms of CAR design than a classical CAR. For example, it allows the formation of homo- or hetero-oligomeric CAR complexes. Hetero-oligomeric CAR complexes are useful when engineering multi-chain CARs with CD28/OX40/41BB and TCRz endodomains in order to ensure that each of the endodomains is located with optimal proximity to the membrane and present at the desired ratios.

The present inventors have engineered a hyper-sensitive CAR without changing the biophysical properties of the binder domain. This is desirable because methods to reduce the affinity of CAR binders are unpredictable and often have uncharacterised specificity.

The hyper-sensitive CAR is provided by increasing the valency of the CAR. In particular, the use of a coiled coil spacer domain which is capable of interacting to form a multimer comprising more than two CARs increases the sensitivity to targets expressing low density ligands due to the increase in ITAMs and avidity to the oligomeric CAR complex.

Sensitivity may be increased by increasing the ratio of coil-signal to scFv-coil, so each scFv is attached to many signaling elements (see FIG. 10c). Sensitivity may also me increased via the formation of complexes of multimeric CARs (FIG. 10f).

In a multimeric CAR of the invention, the signaling endodomains are provided in trans in a membrane proximal location, enabling fine tuning of the T-cell signalling domain combinations (FIGS. 10 a and b); and the incorporation of more than three distinct intracellular signalling domains (FIG. 10d) so that the structure includes more endodomain signals than a third generation CAR (FIG. 1d).

The use of a separate intracellular signalling component molecule which heterodimerizes with the CAR intracellularly enables the further amplification on the number of endodomains per antigen binding domain, producing a "superCAR" (FIG. 15).

A multimeric CAR of the invention may comprise more than one antigen-binding specificity, enabling a plurality of epitopes or antigens to be targeted (FIG. 10e).

A multimeric CAR having a plurality of binding domains will have much greater avidity than a classical homodimeric CAR. This can be important, for example for binding domains with low affinity, as the accumulated strength of multiple affinities provides high specificity binding. A multimeric CAR may bind antigen in a fashion analogous to IgM, which comprises multiple immunoglobulins covalently linked to form a pentameric or hexameric structure,

DESCRIPTION OF THE FIGURES

FIG. 15—Schematic diagram of the Coiled-coil Super-CAR constructs tested in Example 7:
aCD19-IgGFc-Z—a classical homodimeric CAR comprising 2 TCRz molecules per molecule, having the fmc63 aCD19 binder.
A coiled coil SuperCAR made up of five polypeptides each comprising four separate AD1 domains. The coiled-coil SuperCAR therefore comprises 20 AD1 domains.
COMP_x4AD1—the coiled-coil SuperCAR was tested in combination with a signalling component having 0 copies of the TCR zeta signalling domain. This was used as a negative control.
COMP_x4AD1+Z-DDD1-Z—the coiled-coil SuperCAR was tested in combination with a signalling component having 2 copies of the TCR zeta signalling domain. As DDD1 binds AD1 in a 2:1 stoichiometry, this signalling domains gives 80 copies of the TCR zeta domain for each 5-polypeptide coiled-coil CAR targeting component.

DETAILED DESCRIPTION

Chimeric Antigen Receptors (CARs)

Figure 1:
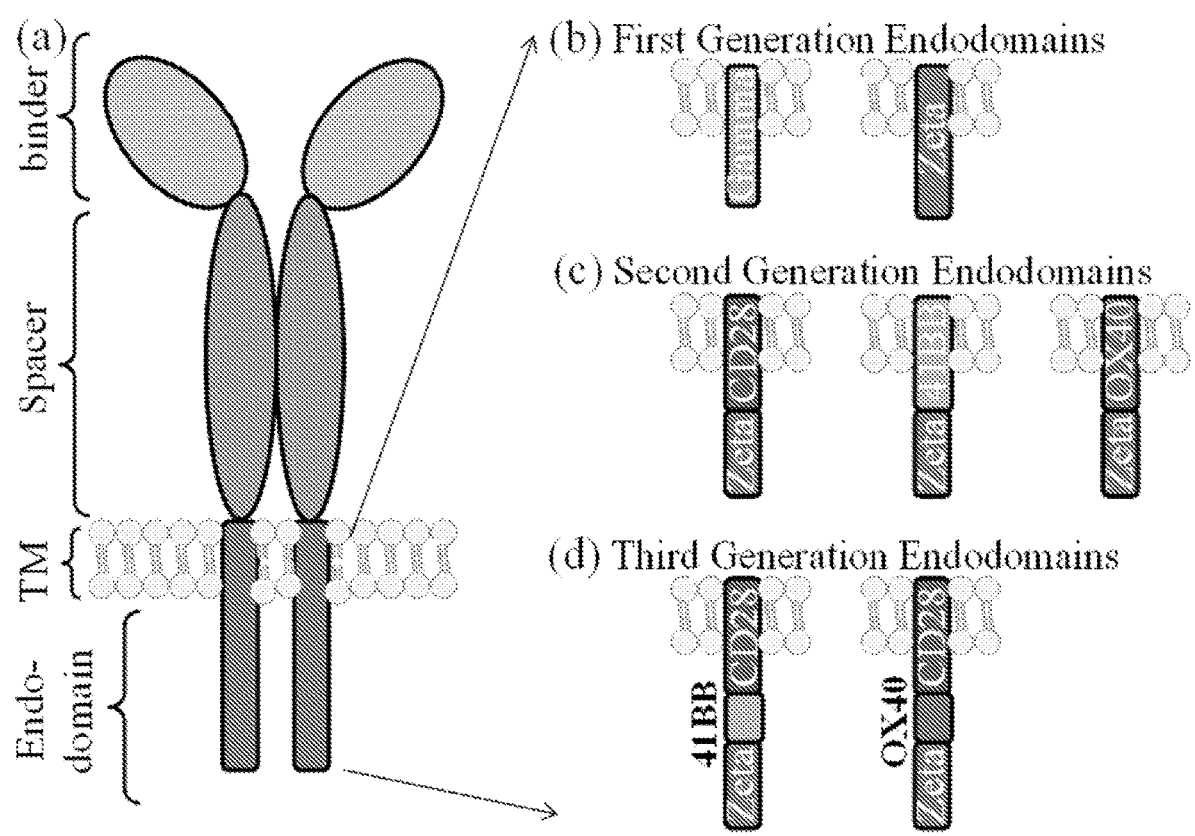
FIG. 1—a) Schematic diagram illustrating a classical CAR. (b) to (d): Different generations and permutations of CAR endodomains: (b) initial designs transmitted ITAM signals alone through FcεR1-γ or CD3ζ endodomain, while later designs transmitted additional (c) one or (d) two co-stimulatory signals in the same compound endodomain.
Figure 2:
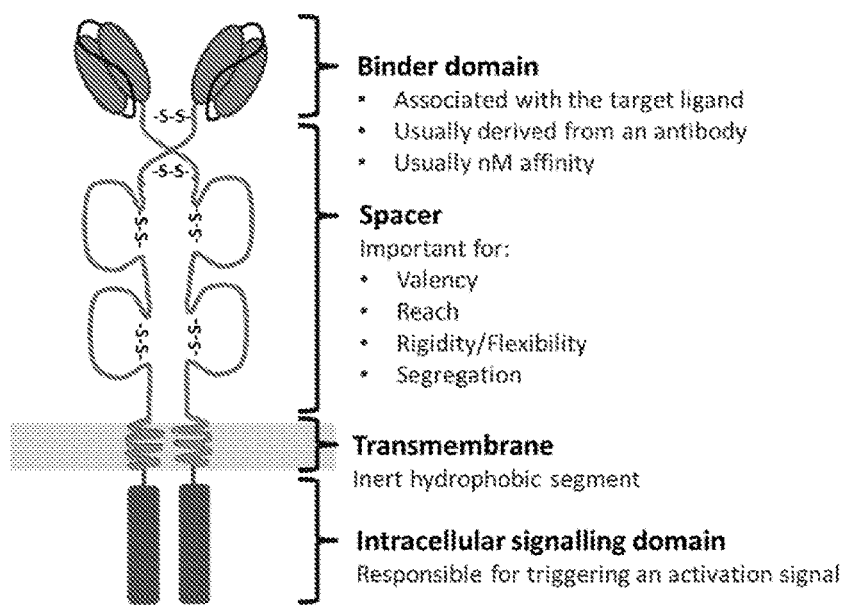
FIG. 2—a) Schematic diagram illustrating a classical CAR. b) Schematic diagram illustrating common CAR spacers. "S" denotes disulfide bonds.
Figure 2:
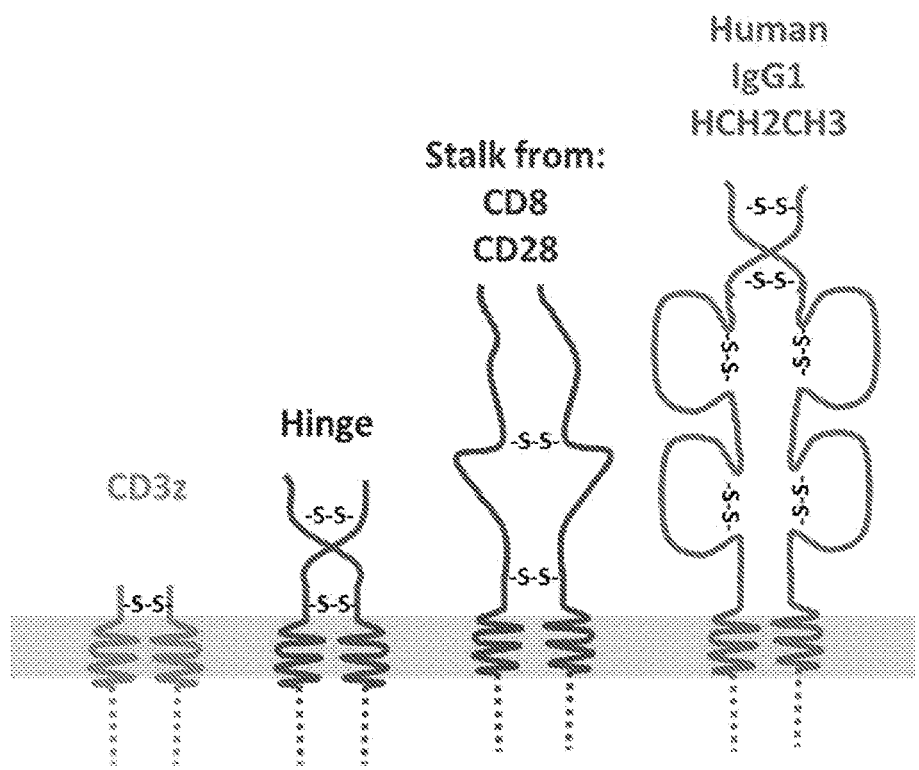

Classical CARs, which are shown schematically in FIG. 1, are chimeric type I transmembrane proteins which connect an extracellular antigen-recognizing domain (binder) to an intracellular signalling domain (endodomain). The binder is typically a single-chain variable fragment (scFv) derived from a monoclonal antibody (mAb), but it can be based on other formats which comprise an antibody-like or ligand-based antigen binding site. A transmembrane domain anchors the protein in the cell membrane and connects the spacer to the endodomain.

Early CAR designs had endodomains derived from the intracellular parts of either the κ chain of the FcεR1 or CD3ζ. Consequently, these first generation receptors transmitted immunological signal 1, which was sufficient to trigger T-cell killing of cognate target cells but failed to fully activate the T-cell to proliferate and survive. To overcome this limitation, compound endodomains have been constructed: fusion of the intracellular part of a T-cell co-stimulatory molecule to that of CD3ζ results in second generation receptors which can transmit an activating and co-stimulatory signal simultaneously after antigen recognition. The co-stimulatory domain most commonly used is that of CD28. This supplies the most potent co-stimulatory signal—namely immunological signal 2, which triggers T-cell proliferation. Some receptors have also been described which include TNF receptor family endodomains, such as the closely related OX40 and 41BB which transmit survival signals. Even more potent third generation CARs have now been described which have endodomains capable of transmitting activation, proliferation and survival signals.

CAR-encoding nucleic acids may be transferred to T cells using, for example, retroviral vectors. In this way, a large number of antigen-specific T cells can be generated for adoptive cell transfer. When the CAR binds the target-antigen, this results in the transmission of an activating signal to the T-cell it is expressed on. Thus the CAR directs the specificity and cytotoxicity of the T cell towards cells expressing the targeted antigen.

The present CAR comprises an antigen-binding domain, a coiled-coil spacer domain, a transmembrane domain and an endodomain. The coiled-coil spacer domain provides numerous advantages over the spacers previously described in the art.

Coiled Coil Domain

CARs typically comprise a spacer sequence to connect the antigen-binding domain with the transmembrane domain. The spacer allows the antigen-binding domain to have a suitable orientation and reach. The spacer also provides segregation from phosphatases upon ligand engagement.

The CAR of the present invention comprises a coiled coil spacer domain.

Figure 3:
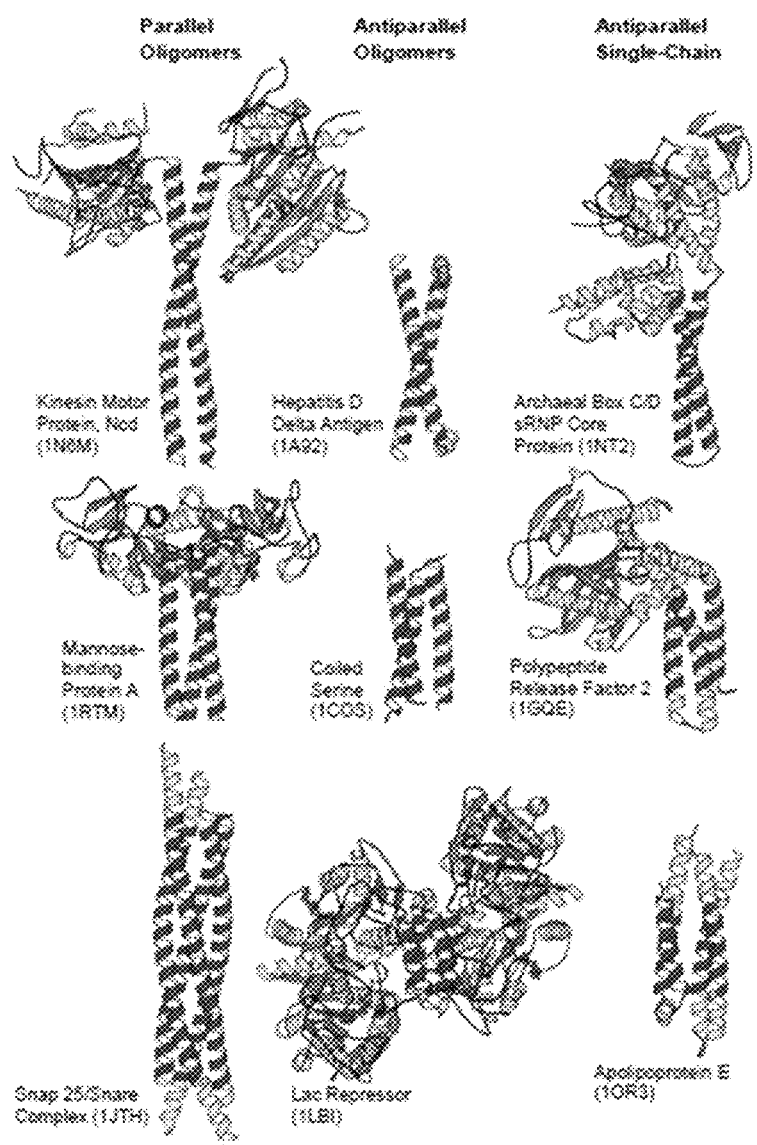
FIG. 3—Naturally occurring dimeric, trimeric and tetrameric coiled coil structures (modified from Andrei N. Lupas and Markus Gruber; Adv Protein Chem. 2005; 70:37-78)

A coiled coil is a structural motif in which two to seven alpha-helices are wrapped together like the strands of a rope (FIG. 3). Many endogenous proteins incorporate coiled coil domains. The coiled coil domain may be involved in protein folding (e.g. it interacts with several alpha helical motifs within the same protein chain) or responsible for protein-protein interaction. In the latter case, the coiled coil can initiate homo or hetero oligomer structures.

As used herein, the terms 'multimer' and 'multimerization' are synonymous and interchangeable with 'oligomer' and 'oligomerization'.

The structure of coiled coil domains is well known in the art. For example as described by Lupas & Gruber (Advances in Protein Chemistry; 2007; 70; 37-38).

Coiled coils usually contain a repeated pattern, hxxhcxc, of hydrophobic (h) and charged (c) amino-acid residues, referred to as a heptad repeat. The positions in the heptad repeat are usually labeled abcdefg, where a and d are the hydrophobic positions, often being occupied by isoleucine, leucine, or valine. Folding a sequence with this repeating pattern into an alpha-helical secondary structure causes the hydrophobic residues to be presented as a 'stripe' that coils gently around the helix in left-handed fashion, forming an amphipathic structure. The most favourable way for two such helices to arrange themselves in the cytoplasm is to wrap the hydrophobic strands against each other sandwiched between the hydrophilic amino acids. Thus, it is the burial of hydrophobic surfaces that provides the thermodynamic driving force for the oligomerization. The packing in a coiled-coil interface is exceptionally tight, with almost complete van der Waals contact between the side-chains of the a and d residues.

The α-helices may be parallel or anti-parallel, and usually adopt a left-handed super-coil. Although disfavoured, a few right-handed coiled coils have also been observed in nature and in designed proteins.

The coiled coil domain may be any coiled coil domain which is capable of forming a coiled coil multimer such that a complex of CARs or accessory polypeptides comprising the coiled coil domain is formed.

The relationship between the sequence and the final folded structure of a coiled coil domain are well understood in the art (Mahrenholz et al; Molecular & Cellular Proteomics; 2011; 10(5):M110.004994). As such the coiled coil domain may be a synthetically generated coiled coil domain.

Examples of proteins which contain a coiled coil domain include, but are not limited to, kinesin motor protein, hepatitis D delta antigen, archaeal box C/D sRNP core protein, cartilage-oligomeric matrix protein (COMP), mannose-binding protein A, coiled-coil serine-rich protein 1, polypeptide release factor 2, SNAP-25, SNARE, Lac repressor or apolipoprotein E.

The sequence of various coiled coil domains is shown below:

```
Kinesin motor protein: parallel homodimer
                                       (SEQ ID No. 30)
MHAALSTEVVHLRQRTEELLRCNEQQAAELETCKEQLFQSNMERKEL

HNTVMDLRGN

Hepatitis D delta antigen: parallel homodimer
                                       (SEQ ID No. 31)
GREDILEQWVSGRKKLEELERDLRKLKKKIKKLEEDNPWLGNIKGII

GKY

Archaeal box C/D sRNP core protein: anti-
parallel heterodimer
                                       (SEQ ID No. 32)
RYVVALVKALEEIDESINMLNEKLEDIRAVKESEITEKFEKKIRELR

ELRRDVEREIEEVM

Mannose-binding protein A: parallel homotrimer
                                       (SEQ ID No. 33)
AIEVKLANMEAEINTLKSKLELTNKLHAFSM Coiled-coil serine-rich protein 1: parallel
homotrimer
                                       (SEQ ID No. 34)
EWEALEKKLAALESKLQALEKKLEALEHG Polypeptide release factor 2: anti-parallel
heterotrimer
Chain A:
                                       (SEQ ID No. 35)
INPVNNRIQDLTERSDVLRGYLDY Chain B:
                                       (SEQ ID No. 36)
VVDTLDQMKQGLEDVSGLLELAVEADDEETFNEAVAELDALEEKLAQ

LEFR

SNAP-25 and SNARE: parallel heterotetramer

Chain A:
                                       (SEQ ID No. 37)
IETRHSEIIKLENSIRELHDMFMDMAMLVESQGEMIDRIEYNVEHAV

DYVE

Chain B:
                                       (SEQ ID No. 38)
ALSEIETRHSEIIKLENSIRELHDMFMDMAMLVESQGEMIDRIEYNV

EHAVDYVERAVSDTKKAVKY

Chain C:
                                       (SEQ ID No. 39)
ELEEMQRRADQLADESLESTRRMLQLVEESKDAGIRTLVMLDEQGEQ

LERIEEGMDQINKDMKEAEKNL

Chain D:
                                       (SEQ ID No. 40)
IETRHSEIIKLENSIRELHDMFMDMAMLVESQGEMIDRIEYNVEHAV

DYVE

Lac repressor: parallel homotetramer
                                       (SEQ ID No. 41)
SPRALADSLMQLARQVSRLE Apolipoprotein E: anti-parallel heterotetramer
                                       (SEQ ID No. 42)
SGQRWELALGRFWDYLRWVQTLSEQVQEELLSSQVTQELRALMDETM

KELKAYKSELEEQLTARLSKELQAAQARLGADMEDVCGRLVQYRGEV

QAMLGQSTEELRVRLASHLRKLRKRLLRDADDLQKRLAVYQA
```

The coiled coil domain is capable of oligomerization. In certain embodiments, the coiled coil domain may be capable of forming a trimer, a tetramer, a pentamer, a hexamer or a heptamer.

A coiled-coil domain is different from a leucine zipper. Leucine zippers are super-secondary structures that function as a dimerization domains. Their presence generates adhesion forces in parallel alpha helices. A single leucine zipper consists of multiple leucine residues at approximately 7-residue intervals, which forms an amphipathic alpha helix with a hydrophobic region running along one side. This hydrophobic region provides an area for dimerization, allowing the motifs to "zip" together. Leucine zippers are typically 20 to 40 amino acids in length, for example approximately 30 amino acids.

Leucine zippers are typically formed by two different sequences, for example an acidic leucine zipper heterodimerizes with a basic leucine zipper. An example of a leucine zipper is the docking domain (DDD1) and anchoring domain (AD1) which are described in more detail below.

Leucine zippers form dimers, whereas the coiled-coiled spacers of the present invention for multimers (trimers and above). Leucine zippers heterodimerise in the dimerization potion of the sequence, whereas coiled-coil domains homodimerise.

In one embodiment, the present invention provides a hyper-sensitive CAR.

The hyper-sensitive CAR is provided by increasing the valency of the CAR. In particular, the use of a coiled coil spacer domain which is capable of interacting to form a multimer comprising more than two coiled coil domains, and therefore more than two CARs, increases the sensitivity to targets expressing low density ligands due to increasing the number of ITAMs present and avidity of the oligomeric CAR complex.

Thus in one embodiment the present CAR-forming polypeptide comprises a coiled coil spacer domain which enables the multimerization of at least three CAR-forming polypeptides. In other words, the CAR comprises a coiled coil domain which is capable of forming a trimer, a tetramer, a pentamer, a hexamer or a heptamer of coiled coil domains.

Examples of coiled coil domains which are capable of forming multimers comprising more than two coiled coil domains include, but are not limited to, those from cartilage-oligomeric matrix protein (COMP), mannose-binding protein A, coiled-coil serine-rich protein 1, polypeptide release factor 2, SNAP-25, SNARE, Lac repressor or apolipoprotein E (see SEQ ID Nos. 30-42 above).

The coiled coil domain may be the COMP coiled coil domain.

Figure 4:
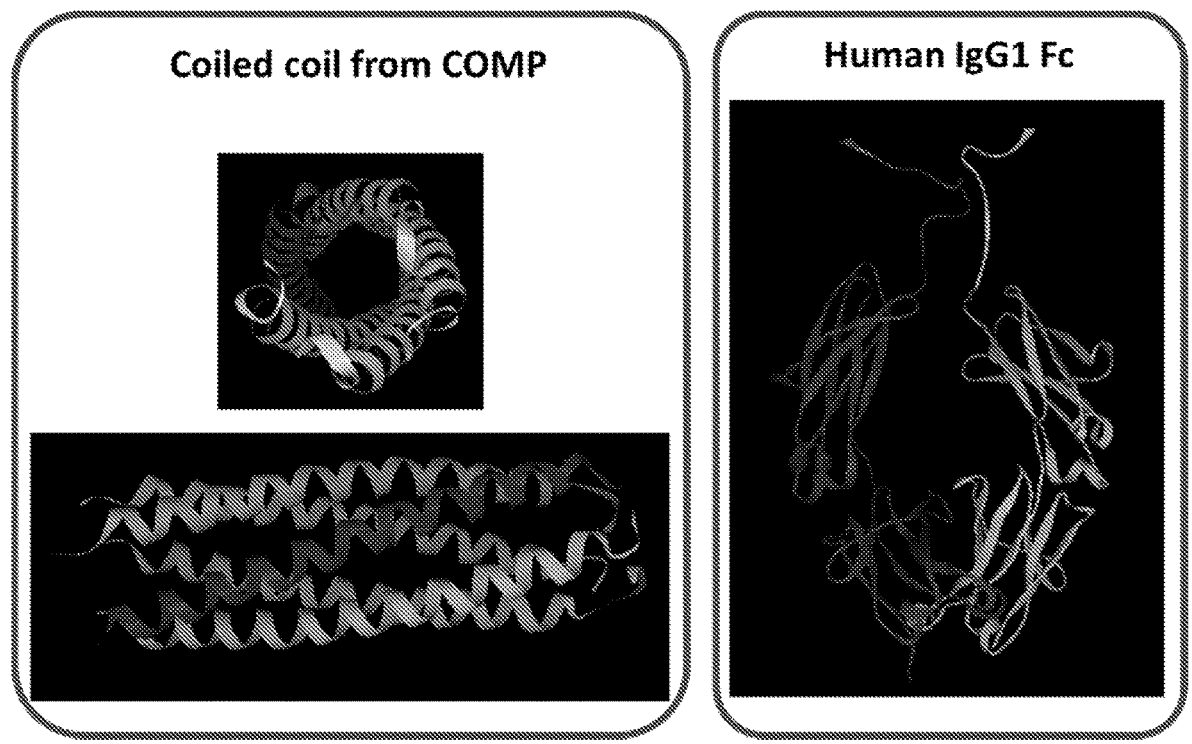
FIG. 4—Crystal structure of the pentameric coiled coil motif from collagen oligomeric matrix protein (COMP) and human IgG1. Individual chains are depicted with different colours. The coiled coil COMP structure is displayed from the N-terminus with the C-terminus extending into the page and also displayed from the profile with the C-terminus left to the N-terminus right. The human IgG1 is displayed from the profile with the N-terminus (top) to C-terminus (bottom).

COMP is one of the most stable protein complexes in nature (stable from 0° C.-100° C. and a wide range of pH) and can only be denatured with 4-6M guanidine hydrochloride. The COMP coiled coil domain is capable of forming a pentamer. COMP is also an endogenously expressed protein that is naturally expressed in the extracellular space. This reduces the risk of immunogenicity compared to synthetic spacers. Furthermore, the crystal structure of the COMP coiled coil motif has been solved which gives an accurate estimation on the spacer length (FIG. 4). The COMP structure is ~5.6 nm in length (compared to the hinge and CH2CH3 domains from human IgG which is ~8.1 nm).

The coiled coil domain may consist of or comprise the sequence shown as SEQ ID No. 1 or a fragment thereof.

```
                                          SEQ ID No. 1
DLGPQMLRELQETNAALQDVRELLRQQVREITFLKNTVMECDACG
```

Figure 11:
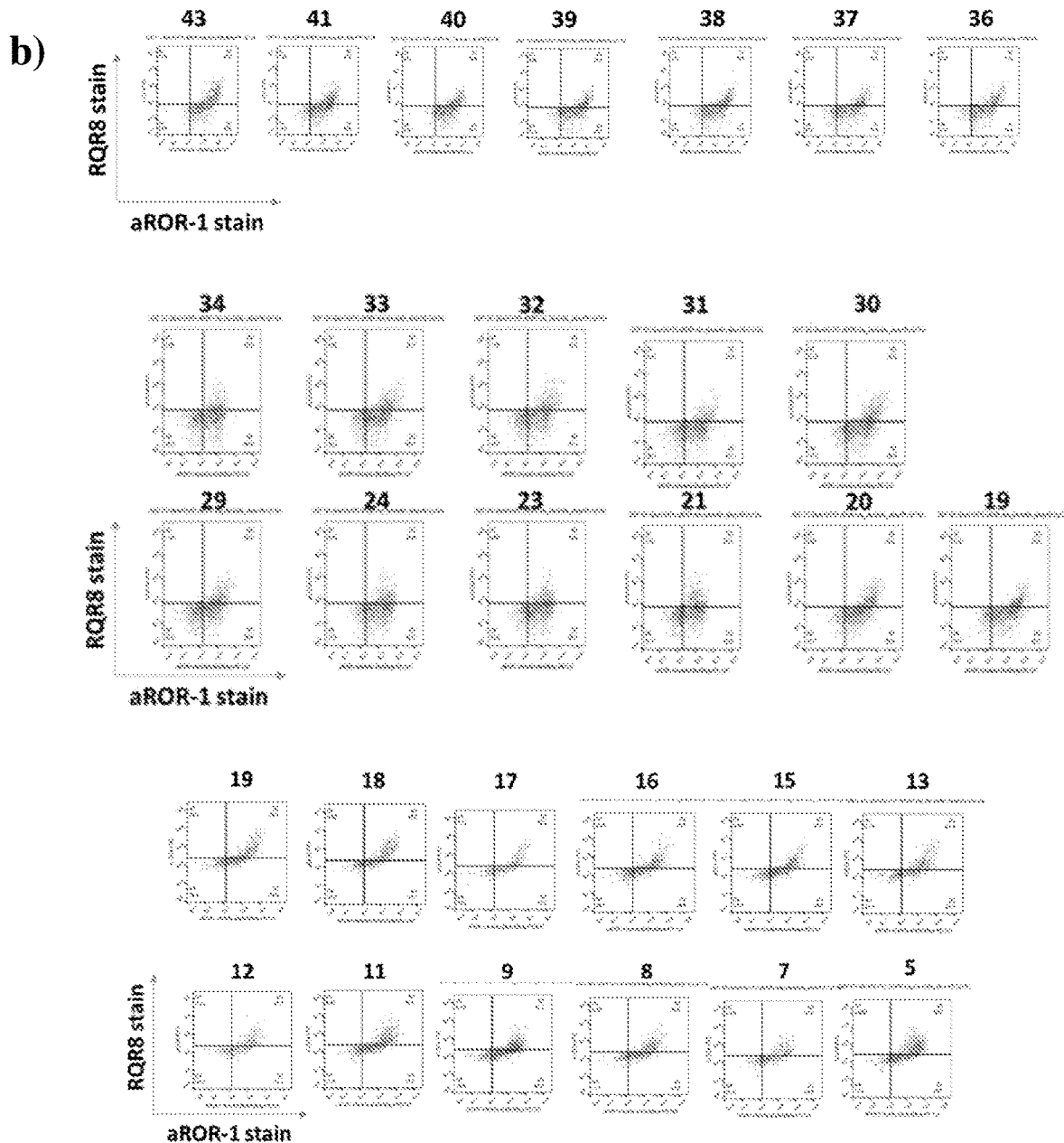
FIG. 11—Truncation of the COMP spacer
a) schematic diagram showing the anti-ROR-1 COMP CAR, the COMP spacer was truncated from the N-terminus from 45 amino acids to "x" amino acids
b) 293T cells were transfected with the truncated constructs and analysed by FACS.

As shown in FIG. 11, it is possible to truncate the COMP coiled-coil domain at the N-terminus and retain surface expression. The coiled-coil domain may therefore comprise or consist of a truncated version of SEQ ID No. 1, which is truncated at the N-terminus. The truncated COMP may comprise the 5 C-terminal amino acids of SEQ ID No. 1, i.e. the sequence CDACG (SEQ ID NO: 49). The truncated COMP may comprise 5 to 44 amino acids, for example, at least 5, 10, 15, 20, 25, 30, 35 or 40 amino acids. The truncated COMP may correspond to the C-terminus of SEQ ID No. 1. For example a truncated COMP comprising 20 amino acids may comprise the sequences QQVREITFLKNTVMECDACG (SEQ ID NO: 47). Truncated COMP may retain the cysteine residue(s) involved in multimerisation. Truncated COMP may retain the capacity to form multimers.

Various coiled coil domains are known which form hexamers such as gp41 derived from HIV, and an artificial protein designed hexamer coiled coil described by N. Zaccai et al. (2011) Nature Chem. Bio., (7) 935-941). A mutant form of the GCN4-p1 leucine zipper forms a heptameric coiled-coil structure (J. Liu. et al., (2006) PNAS (103) 15457-15462).

The coiled coil domain may comprise a variant of one of the coiled coil domains described above, providing that the variant sequence retains the capacity to form a coiled coil oligomer. For example, the coiled coil domain may comprise a variant of the sequence shown as SEQ ID No. 1 or 30 to 42 having at least 80, 85, 90, 95, 98 or 99% sequence identity, providing that the variant sequence retains the capacity to form a coiled coil oligomer.

The percentage identity between two polypeptide sequences may be readily determined by programs such as BLAST which is freely available at http://blast.ncbi.nlm.nih.gov.

Antigen Binding Domain

The antigen-binding domain is the portion of a classical CAR which recognizes antigen.

Numerous antigen-binding domains are known in the art, including those based on the antigen binding site of an antibody, antibody mimetics, and T-cell receptors. For example, the antigen-binding domain may comprise: a single-chain variable fragment (scFv) derived from a monoclonal antibody; a natural ligand of the target antigen; a peptide with sufficient affinity for the target; a single domain binder such as a camelid; an artificial binder single as a Darpin; or a single-chain derived from a T-cell receptor.

Various tumour associated antigens (TAA) are known, as shown in the following Table 1. The antigen-binding domain used in the present invention may be a domain which is capable of binding a TAA as indicated therein.

TABLE 1

| Cancer type | TAA |
|---|---|
| Diffuse Large B-cell Lymphoma | CD19, CD20, CD22 |
| Breast cancer | ErbB2, MUC1 |
| AML | CD13, CD33 |
| Neuroblastoma | GD2, NCAM, ALK, GD2 |
| B-CLL | CD19, CD52, CD160 |
| Colorectal cancer | Folate binding protein, CA-125 |
| Chronic Lymphocytic Leukaemia | CD5, CD19 |
| Glioma | EGFR, Vimentin |
| Multiple myeloma | BCMA, CD138 |
| Renal Cell Carcinoma | Carbonic anhydrase IX, G250 |
| Prostate cancer | PSMA |
| Bowel cancer | A33 |

In certain embodiments, the present invention provides a hyper-sensitive CAR which is capable of stimulating cell activation in response to antigen which is expressed on a target cell at a low density.

The antigen binding domain may bind a TAA which is expressed on a cell, for example a cancer cell, at a low density. A TAA expressed at low density may refer, for example, to a TAA expressed at a level of 10s to 1000s molecules per cell.

Examples of TAAs which are known to be expressed at low densities in certain cancers include, but are not limited to, ROR1 in CLL, Typr-1 in melanoma and BCMA in myeloma.

Antigen-binding domains (such as scFvs or mAbs) which bind these TAAs have previously been described, for example as shown in the following table:

| Tumour-associated antigen | Antigen-binding domain | Reference |
|---|---|---|
| ROR-1 | 2A2, 2D11 | S. Baskar et al., Landes Bioscience, vol. 4, (3) 349-361), R12, R11, Y31 (J. Yang et al., PLOSone, vol. 6, (6), e21018, 2011 |
| Tyrp-1 | TA99 | P. Boross et al., Immunology Letters, vol. 160, (2), 151-157, 2014 |
| BCMA | C12A3.2 and C11D5.3 | R. Carpenter et al., Clin Cancer Res., vol. 19, (8) 2048-2060, 2013), J6M0 (Y. Tai et al., Blood, vol 123, (20), 3128-3138, 2014 |

Transmembrane Domain

The transmembrane domain is the sequence of a CAR that spans the membrane. It may comprise a hydrophobic alpha helix. The transmembrane domain may be derived from CD28, which gives good receptor stability.

Signal Peptide

The CAR-forming polypeptides and/or accessory polypeptides of the present invention may comprise a signal peptide so that when it is expressed in a cell, such as a T-cell, the nascent protein is directed to the endoplasmic reticulum and subsequently to the cell surface, where it is expressed.

The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases.

The signal peptide may be at the amino terminus of the molecule.

The signal peptide may comprise the sequence shown as SEQ ID No. 2, 3 or 4 or a variant thereof having 5, 4, 3, 2 or 1 amino acid mutations (insertions, substitutions or additions) provided that the signal peptide still functions to cause cell surface expression of the CAR.

```
SEQ ID No. 2:
MGTSLLCWMALCLLGADHADG
```

The signal peptide of SEQ ID No. 2 is compact and highly efficient and is derived from TCR beta chain. It is predicted to give about 95% cleavage after the terminal glycine, giving efficient removal by signal peptidase.

```
SEQ ID No. 3:
MSLPVTALLLPLALLLHAARP
```

The signal peptide of SEQ ID No. 3 is derived from IgG1.

```
SEQ ID No. 4:
MAVPTQVLGLLLLWLTDARC
```

The signal peptide of SEQ ID No. 4 is derived from CD8a.

Endodomain

The endodomain is the portion of a classical CAR which is located on the intracellular side of the membrane.

The endodomain is the signal-transmission portion of a classical CAR. After antigen recognition by the antigen binding domain, individual CAR molecules cluster, native CD45 and CD148 are excluded from the synapse and a signal is transmitted to the cell.

The endodomain of a coiled-coil spacer CAR may be or comprise an intracellular signalling domain. In an alternative embodiment, the endodomain of the present CAR may be capable of interacting with an intracellular signalling molecule which is present in the cytoplasm, leading to signalling.

The intracellular signalling domain or separate intracellular signalling molecule may be or comprise a T cell signalling domain.

The most commonly used signalling domain is that of CD3-zeta endodomain, which contains 3 ITAMs. This transmits an activation signal to the T cell after antigen is bound. CD3-zeta may not provide a fully competent activation signal and additional co-stimulatory signalling may be needed. For example, chimeric CD28 and OX40 can be used with CD3-Zeta to transmit a proliferative/survival signal, or all three can be used together (illustrated in FIG. 1B).

The present CAR may comprise the CD3-Zeta endodomain alone, the CD3-Zeta endodomain with that of either CD28 or OX40 or the CD28 endodomain and OX40 and CD3-Zeta endodomain (FIG. 1).

The endodomain may comprise one or more of the following: an ICOS endodomain, a CD27 endodomain, a BTLA endodomain, a CD30 endodomain, a GITR endodomain and an HVEM endodomain.

The endomain may comprise the sequence shown as SEQ ID No. 5 to 13 or a variant thereof having at least 80% sequence identity.

```
CD3 Z endodomain
                                       SEQ ID No. 5
RVKFSRSADAPAYQQGQNQLYNELNLGRREEYDVLDKRRGRDPEM

GGKPRRKNPQEGLYNELQKDKMAEAYSEIGMKGERRRGKGHDGLY

QGLSTATKDTYDALHMQALPPR

CD28 and CD3 Zeta endodomains
                                       SEQ ID No. 6
SKRSRLLHSDYMNMTPRRPGPTRKHYQPYAPPRDFAAYRSRVKFS

RSADAPAYQQGQNQLYNELNLGRREEYDVLDKRRGRDPEMGGKPR

RKNPQEGLYNELQKDKMAEAYSEIGMKGERRRGKGHDGLYQGLST

ATKDTYDALHMQALPPR

CD28, OX40 and CD3 Zeta endodomains
                                       SEQ ID No. 7
SKRSRLLHSDYMNMTPRRPGPTRKHYQPYAPPRDFAAYRSRDQRL

PPDAHKPPGGGSFRTPIQEEQADAHSTLAKIRVKFSRSADAPAYQ

QGQNQLYNELNLGRREEYDVLDKRRGRDPEMGGKPRRKNPQEGLY

NELQKDKMAEAYSEIGMKGERRRGKGHDGLYQGLSTATKDTYDAL

HMQALPPR

ICOS endodomain
                                       SEQ ID No. 8
CWLTKKKYSSSVHDPNGEYMFMRAVNTAKKSRLTDVTL CD27 endodomain
                                       SEQ ID No. 9
QRRKYRSNKGESPVEPAEPCHYSCPREEEGSTIPIQEDYRKPEPA

CSP

BTLA endodomain
                                       SEQ ID No. 10
RRHQGKQNELSDTAGREINLVDAHLKSEQTEASTRQNSQVLLSET

GIYDNDPDLCFRMQEGSEVYSNPCLEENKPGIVYASLNHSVIGPN

SRLARNVKEAPTEYASICVRS

CD30 endodomain
                                       SEQ ID No. 11
HRRACRKRIRQKLHLCYPVQTSQPKLELVDSRPRRSSTQLRSGAS

VTEPVAEERGLMSQPLMETCHSVGAAYLESLPLQDASPAGGPSSP

RDLPEPRVSTEHTNNKIEKIYIMKADTVIVGTVKAELPEGRGLAG

PAEPELEEELEADHTPHYPEQETEPPLGSCSDVMLSVEEEGKEDP

LPTAASGK
```

```
-continued
GITR endodomain
                                     SEQ ID No. 12
QLGLHIWQLRSQCMWPRETQLLLEVPPSTEDARSCQFPEEERGER

SAEEKGRLGDLWV

HVEM endodomain
                                     SEQ ID No. 13
CVKRRKPRGDVVKVIVSVQRKRQEAEGEATVIEALQAPPDVTTVA

VEETIPSFTGRSPNH
```

A variant sequence may have at least 80%, 85%, 90%, 95%, 98% or 99% sequence identity to SEQ ID No. 5 to 13, provided that the sequence provides an effective intracellular signalling domain.

Chimeric Antigen Receptor (CAR)

In one aspect the present invention provides a CAR comprising a CAR-forming polypeptide according to the first aspect of the invention and an accessory polypeptide which comprises (i) a coiled-coil spacer domain; (ii) a transmembrane domain; and (iii) an endodomain, wherein the coiled-coil spacer domain of the accessory polypeptide is capable of interacting with the coiled-coil domain of the CAR-forming polypeptide.

The CAR-forming polypeptide provides the antigen-binding domain and hence the antigen specificity.

The accessory polypeptide provides an additional endodomain which may be used for generating a desired signalling response. This is advantageous over a compound signalling domain since each signalling domain remains unencumbered from other signalling domains.

In addition, it allows each signalling domain to be localised at an optimal proximity to the membrane for signalling.

The endodomain of the CAR-forming polypeptide may comprise at least a first intracellular signalling domain; and the endodomain of the accessory polypeptide may comprise at least a second intracellular signalling domain. For example, one of the endodomain of the CAR-forming polypeptide and the accessory polypeptide may comprise a CD3 zeta endodomain and the other endodomain of the CAR and the accessory polypeptide may comprise a 41BB endodomain.

In another embodiment, the present invention provides a CAR according to the second aspect of the present invention, further comprising a second accessory polypeptide comprising: (i) a coiled-coil domain; (ii) a transmembrane domain; and (iii) an endodomain; wherein the coiled-coil domain of the second accessory polypeptide is capable of interacting with the coiled-coil domains of the CAR-forming polypeptide and the first accessory polypeptide.

The endodomain of the CAR-forming polypeptide may comprise at least a first intracellular signalling domain, the endodomain of the first accessory polypeptide may comprise at least a second intracellular signalling domain and the endodomain of the second accessory polypeptide may comprise at least a third intracellular signalling domain.

For example, the endodomains of the CAR, the first accessory polypeptide and the second accessory polypeptide may comprise between them a CD3 zeta endodomain; a 41BB endodomain; and a CD28 endodomain.

The present invention also provides an accessory polypeptide suitable for use in a CAR as described herein.

Multimeric CAR

The present invention provides a multimeric CAR which comprises a plurality of CAR-forming polypeptides according to the present invention and optionally accessory polypeptide(s) which form a complex due to interactions between the coiled coil spacer domains.

The multimeric CAR may be, for example, trimeric, tetrameric, pentameric, hexameric or heptameric.

The number of CAR-foring polypeptides vs accessory proteins in each type of CAR is summarised in the Tables below:

Trimeric CAR:

| Number of CAR-forming polypeptides | Number of accessory polypeptides |
|---|---|
| 1 | 2 |
| 2 | 1 |
| 3 | 0 |

Tetrameric CAR:

| Number of CAR-forming polypeptides | Number of accessory polypeptides |
|---|---|
| 1 | 3 |
| 2 | 2 |
| 3 | 1 |
| 4 | 0 |

Pentameric CAR:

| Number of CAR-forming polypeptides | Number of accessory polypeptides |
|---|---|
| 1 | 4 |
| 2 | 3 |
| 3 | 2 |
| 4 | 1 |
| 5 | 0 |

The association of CAR-forming polypeptides and accessory polypeptides within a cell will be random, so the options given in the tables above may refer to a single multimeric CAR, in which the number of CAR-forming polypeptides and accessory polypeptides can be precisely defined, or the average number of CAR-forming polypeptides and accessory polypeptides in multiplexed CARs expressed on a cell. In systems where there is a high accessory polypeptide:CAR-forming polypeptide ratio, it is possible that some multiplexes of accessory polypeptide alone will be expressed on the cell surface. This is not a problem, as long as at least some of the multiplexes expressed at the cell surface comprise a CAR-foring polypeptide.

The plurality of CAR-forming polypeptides and optionally accessory polypeptide(s) may comprise the same endodomain.

Alternatively, the plurality of CAR-foring polypeptides and optionally accessory polypeptide(s) may comprise different endodomains. In this way, multiple different endodomains can be activated simultaneously. This is advantageous over a compound signalling domain since each signalling domain remains unencumbered from other signalling domains. In addition, it allows each signalling domain to be localised at an optimal proximity to the membrane for signalling.

Where a multimeric CAR comprises a plurality of antigen binding domains, this will increase the avidity of antigen binding. The multimeric CAR may mimic antigen binding by IgM, which comprises a pentameric or hexameric arrangement of immunoglobulins.

CAR Signalling System

The present invention also provides a chimeric antigen receptor (CAR) signalling system, which comprises:
(i) a multimeric CAR comprising a CAR-forming polypeptide or accessory polypeptide as defined above which comprises a first heterodimerization domain; and
(ii) an intracellular signalling component comprising a signalling domain and a second heterodimerization domain;
wherein heterodimerization between the first and second heterodimerization domains causes the multimeric CAR and signalling component to form a functional CAR complex.

Each CAR-forming polypeptide(s) or accessory polypeptide(s) may comprise a plurality of heterodimerisation domains, such that a single CAR-forming polypeptide or accessory polypeptide is capable of heterodimerising with a plurality of signalling components. An example of such a system is illustrated in FIG. 15.

In order to increase the signalling domain:antigen-binding domain even further, each signalling component may comprise a plurality of signalling domains.

Heterodimerisation may occur only in the presence of a small molecule, for example using a system such as the one described in WO2016/030691.

Alternatively heterodimerization may occur spontaneously The first and second heterodimerization domains are capable of spontaneous dimerization with each other. Heterodimerization occurs with the first and second heterodimerization domains alone, without the need for any separate molecule acting as an "inducer" of dimerization.

The signalling system of the present invention is not limited by the arrangement of a specific pair of heterodimerization domains. The targeting component (i.e. the multimeric CAR) may comprise either domain from a pair of heterodimerizing domains so long as the signalling component comprises the corresponding, complementary domain which enables the targeting component and the signalling component to co-localize at the cell membrane.

The heterodimerization domains for use in the present CAR system are not limited to those which interact at a 1:1 ratio. For example, heterodimerization domains may interact to form multimers (e.g. trimers or tetramers). The domains may interact in a manner which co-localises a single first heterodimerization domain with multiple (e.g. 2 or 3) second heterodimerization domains. Herein it may be advantageous to have a signalling domain which comprises the second heterodimerization domain, such that multiple signalling components can co-localise with a single multimeric CAR. This may be advantageous, for example, when a high level of signalling is required upon binding of antigen to the multimeric CAR.

The multimeric CAR may comprise a plurality of heterodimerization domains, so that it interacts with a plurality of signalling components. For example, the multimeric CAR may comprise more than two heterodimerization domains, such a 3 to 10 heterodimerization domains. FIG. 15 shows a multimeric CAR which comprises 20 heterodimerization domains, four per CAR-forming polypeptide/accessory polypeptide.

For convenience, the term heterodimerization domain is used herein for all domains which mediate co-localization of the multimeric CAR and signalling components.

A large variety of appropriate heterodimerization domains are known in the art, examples of which are provided herein.

The first and second heterodimerization domains may be leucine zippers.

Leucine zippers are well known in the art (see Hakoshima; Encyclopedia of Life Sciences; 2005, for example). The leucine zipper is a super-secondary structure that functions as a dimerization domain. Its presence generates adhesion forces in parallel alpha helices. A single leucine zipper consists of multiple leucine residues at approximately 7-residue intervals, which forms an amphipathic alpha helix with a hydrophobic region running along one side. This hydrophobic region provides an area for dimerization, allowing the motifs to "zip" together. Leucine zippers are typically 20 to 40 amino acids in length, for example approximately 30 amino acids.

The first and/or second heterodimerization domain may comprise the sequence shown as SEQ ID NO: 43 or 44. The first heterodimerization domain may comprise the sequence shown as SEQ ID NO: 43 and the second heterodimerization domain may comprise the sequence shown as SEQ ID NO: 44, or vice versa.

```
SEQ ID NO: 43:
QLEKELQALEKENAQLEWELQALEKELAQ

SEQ ID NO: 44:
QLEKKLQALKKKNAQLKWKLQALKKKLAQ
```

In certain embodiments, the first and second heterodimerization domains may be acidic (e.g. SEQ ID NO: 43) or basic (e.g. SEQ ID NO: 44) leucine zippers. In particular, where the first heterodimerization domain is an acidic leucine zipper, the second heterodimerization is a basic leucine zipper and vice versa.

The first and second heterodimerization domains may be dimerization and docking domain (DDD1) and anchoring domain (AD1). These domains and the interaction between them is known in the art (Rossi et al.; PNAS; 2006; 103(18); 6841-6846).

DDD1 is a short alpha helical structure derived from Protein Kinase A (PKA). AD1 is a short alpha helical structure derived from A-kinase anchor proteins (AKAPs).

The DDD1 domain may comprise the sequence shown as SEQ ID NO: 45.

```
SEQ ID NO: 45:
SHIQIPPGLTELLQGYTVEVLRQQPPDLVEFAVEYFTRLREARA
```

The AD1 domain may comprise the sequence shown as SEQ ID NO: 46

```
SEQ ID NO: 46:
VQIEYLAKQIVDNAIQQA
```

Since the DDD1/AD1 interaction is trimeric, an AD1 domain present on the CAR endodomain will recruit three signalling domains comprising a DDD1 domain. Thus in a particular embodiment, the CAR endodomain comprises an AD1 domain and the intracellular signalling component comprises a DDD1 domain.

The heterodimerization domains may be derived from the Bacterial Ribonuclease (Barnase) and Barnstar peptides.

Barnase is the *Bacillus amyloliquefaciens* ribonuclease protein. It is composed on 110 amino acids. Barnstar functions to inhibit the nuclease activity of Barnase and therefore binds Barnstar with a very high affinity (an on-rate of 108s-1M-1).

The heterodimerization domains may be derived from Human Pancreatic RNases and S-peptide.

Human Pancreatic RNase are pyrimidine-specific endonucleases. S-peptide is the enzymatically inactive proteolytic fragment of RNase A, which lacks the RNA binding site.

The present invention also encompasses variants of the heterodimerization sequences described herein which retain the ability to dimerize with the corresponding heterodimerization domain. The heterodimerization domain may be a variant having 5, 4, 3, 2 or 1 amino acid mutations (insertions, substitutions or additions) or at least 80%, 85%, 90%, 95%, 98% or 99% sequence identity compared to the sequence shown as SEQ ID No. 43, 44, 45 or 46 provided that they still cause heterodimerization between the CAR and the signalling component.

Nucleic Acid

The present invention further provides a nucleic acid encoding the CAR-forming polypeptide according to the first aspect of the present invention and/or an accessory polypeptide as defined in the first aspect of the invention.

As used herein, the terms "polynucleotide", "nucleotide", and "nucleic acid" are intended to be synonymous with each other.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

Nucleic acids according to the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the use as described herein, it is to be understood that the polynucleotides may be modified by any method available in the art. Such modifications may be carried out in order to enhance the in vivo activity or life span of polynucleotides of interest.

The terms "variant", "homologue" or "derivative" in relation to a nucleotide sequence include any substitution of, variation of, modification of, replacement of, deletion of or addition of one (or more) nucleic acid from or to the sequence.

The present invention also provides a nucleic acid sequence encoding an accessory polypeptide suitable for use in the CAR according to the second aspect of the present invention.

Nucleic Acid Construct

The present invention also provides a nucleic acid construct which encodes a plurality of nucleic acid sequences.

For example the nucleic acid construct may encode two or more CAR forming polypeptides as defined in the first aspect of the invention.

In this embodiment, the nucleic acid construct may comprise at least two nucleic acid sequences:
(i) a first nucleic acid sequence which encodes a first CAR-forming polypeptide; and
(ii) a second nucleic acid sequence which encodes a second CAR-forming polypeptide.

The nucleic acid construct may encodes at least one CAR-forming polypeptide as defined in the first aspect of the invention and at least one accessory polypeptide as defined above.

In this embodiment, the nucleic acid construct may comprise at least two nucleic acid sequences:
(i) a first nucleic acid sequence which encodes a CAR-forming polypeptide; and
(ii) a second nucleic acid sequence which encodes an accessory polypeptide.

The nucleic acid construct may encode:
(i) at least one CAR-forming polypeptide, which forms a multimeric CAR as defined in the second aspect of the invention; and
(ii) an intracellular signalling component as defined above.

In this embodiment, the nucleic acid construct may comprise at least two nucleic acid sequences:
(i) a first nucleic acid sequence which encodes a CAR-forming polypeptide; and
(ii) a second nucleic acid sequence which encodes an intracellular signalling component.

The nucleic acid construct may comprise a third nucleic acid sequence which encodes an accessory polypeptide.

The nucleic acid construct may therefore produce two or more polypeptide(s) joined by a cleavage site(s). The cleavage site may be self-cleaving, such that when the nascent translation product is produced, it is immediately cleaved into individual polypeptides without the need for any external cleavage activity.

The cleavage site may be any sequence which enables the polypeptide comprising multiple CARs and/or accessory polypeptides to become separated.

The term "cleavage" is used herein for convenience, but the cleavage site may cause the peptides to separate into individual entities by a mechanism other than classical cleavage. For example, for the Foot-and-Mouth disease virus (FMDV) 2A self-cleaving peptide (see below), various models have been proposed for to account for the "cleavage" activity: proteolysis by a host-cell proteinase, autoproteolysis or a translational effect (Donnelly et al (2001) J. Gen. Virol. 82:1027-1041). The exact mechanism of such "cleavage" is not important for the purposes of the present invention, as long as the cleavage site, when positioned between nucleic acid sequences which encode proteins, causes the proteins to be expressed as separate entities.

The cleavage site may be a furin cleavage site.

Furin is an enzyme which belongs to the subtilisin-like proprotein convertase family. The members of this family are proprotein convertases that process latent precursor proteins into their biologically active products. Furin is a calcium-dependent serine endoprotease that can efficiently cleave precursor proteins at their paired basic amino acid processing sites. Examples of furin substrates include proparathyroid hormone, transforming growth factor beta 1 precursor, proalbumin, pro-beta-secretase, membrane type-1 matrix metalloproteinase, beta subunit of pro-nerve growth factor and von Willebrand factor. Furin cleaves proteins just downstream of a basic amino acid target sequence (canonically, Arg-X-(Arg/Lys)-Arg') and is enriched in the Golgi apparatus.

The cleavage site may be a Tobacco Etch Virus (TEV) cleavage site.

TEV protease is a highly sequence-specific cysteine protease which is chymotrypsin-like proteases. It is very specific for its target cleavage site and is therefore frequently used for the controlled cleavage of fusion proteins both in vitro and in vivo. The consensus TEV cleavage site is ENLYFQ\S (where '\' denotes the cleaved peptide bond). Mammalian cells, such as human cells, do not express TEV protease. Thus in embodiments in which the present nucleic acid construct comprises a TEV cleavage site and is expressed in a mammalian cell—exogenous TEV protease must also expressed in the mammalian cell.

The cleavage site may encode a self-cleaving peptide.

A 'self-cleaving peptide' refers to a peptide which functions such that when the nascent product comprising the polypeptides and the self-cleaving peptide is produced, it is immediately "cleaved" or separated into distinct and discrete first and second polypeptides without the need for any external cleavage activity.

The self-cleaving peptide may be a 2A self-cleaving peptide from an aphtho- or a cardiovirus. The primary 2A/2B cleavage of the aptho- and cardioviruses is mediated by 2A "cleaving" at its own C-terminus. In apthoviruses, such as foot-and-mouth disease viruses (FMDV) and equine rhinitis A virus, the 2A region is a short section of about 18 amino acids, which, together with the N-terminal residue of protein 2B (a conserved proline residue) represents an autonomous element capable of mediating "cleavage" at its own C-terminus (Donelly et al (2001) as above).

"2A-like" sequences have been found in picornaviruses other than aptho- or cardioviruses, 'picornavirus-like' insect viruses, type C rotaviruses and repeated sequences within *Trypanosoma* spp and a bacterial sequence (Donnelly et al (2001) as above). The cleavage site may comprise one of these 2A-like sequences, such as:

```
                            (SEQ ID No. 14)
YHADYYKQRLIHDVEMNPGP (SEQ ID No. 15)
HYAGYFADLLIHDIETNPGP (SEQ ID No. 16)
QCTNYALLKLAGDVESNPGP (SEQ ID No. 17)
ATNFSLLKQAGDVEENPGP (SEQ ID No. 18)
AARQMLLLLSGDVETNPGP (SEQ ID No. 19)
RAEGRGSLLTCGDVEENPGP (SEQ ID No. 20)
TRAEIEDELIRAGIESNPGP (SEQ ID No. 21)
TRAEIEDELIRADIESNPGP (SEQ ID No. 22)
AKFQIDKILISGDVELNPGP (SEQ ID No. 23)
SSIIRTKMLVSGDVEENPGP (SEQ ID No. 24)
CDAQRQKLLLSGDIEQNPGP (SEQ ID No. 25)
YPIDFGGFLVKADSEFNPGP
```

The cleavage site may comprise the 2A-like sequence shown as SEQ ID No. 19

```
(RAEGRGSLLTCGDVEENPGP).
```

The present invention also provides a kit comprising one or more nucleic acid sequence(s) encoding a CAR-foring polypeptide according to the first aspect of the present invention and/or an accessory polypeptide suitable for producing a CAR according to the second aspect of the invention.

Vector

The present invention also provides a vector, or kit of vectors, which comprises one or more nucleic acid sequence(s) or nucleic acid construct as defined above. Such a vector may be used to introduce the nucleic acid sequence(s) into a host cell so that it expresses a CAR-forming polypeptide or an accessory peptide according to the first aspect of the invention and/or a CAR according to the second aspect of the invention.

The vector may, for example, be a plasmid or a viral vector, such as a retroviral vector or a lentiviral vector, or a transposon based vector or synthetic mRNA.

The vector may be capable of transfecting or transducing an immune cell such as a T cell or a NK cell.

Cell

The present invention also relates to a cell, such as an immune cell, comprising a CAR-forming polypeptide, CAR, or CAR signalling system as described above.

The cell may comprise a nucleic acid, nucleic acid construct or a vector of the present invention.

The cell may be an immune cell, in particular a cytolytic immune cell, such as a T cell or an NK cell.

T cells or T lymphocytes are a type of lymphocyte that play a central role in cell-mediated immunity. They can be distinguished from other lymphocytes, such as B cells and natural killer cells (NK cells), by the presence of a T-cell receptor (TCR) on the cell surface. There are various types of T cell, as summarised below.

Helper T helper cells (TH cells) assist other white blood cells in immunologic processes, including maturation of B cells into plasma cells and memory B cells, and activation of cytotoxic T cells and macrophages. TH cells express CD4 on their surface. TH cells become activated when they are presented with peptide antigens by MHC class II molecules on the surface of antigen presenting cells (APCs). These cells can differentiate into one of several subtypes, including TH1, TH2, TH3, TH17, Th9, or TFH, which secrete different cytokines to facilitate different types of immune responses.

Cytolytic T cells (TC cells, or CTLs) destroy virally infected cells and tumor cells, and are also implicated in transplant rejection. CTLs express the CD8 at their surface. These cells recognize their targets by binding to antigen associated with MHC class I, which is present on the surface of all nucleated cells. Through IL-10, adenosine and other molecules secreted by regulatory T cells, the CD8+ cells can be inactivated to an anergic state, which prevent autoimmune diseases such as experimental autoimmune encephalomyelitis.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells (TCM cells) and two types of effector memory T cells (TEM cells and TEMRA cells). Memory cells may be either CD4+ or CD8+. Memory T cells typically express the cell surface protein CD45RO.

Regulatory T cells (Treg cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of CD4+ Treg cells have been described—naturally occurring Treg cells and adaptive Treg cells.

Naturally occurring Treg cells (also known as CD4+ CD25+FoxP3+ Treg cells) arise in the thymus and have been linked to interactions between developing T cells with both myeloid (CD11c+) and plasmacytoid (CD123+) dendritic cells that have been activated with TSLP. Naturally occurring Treg cells can be distinguished from other T cells by the presence of an intracellular molecule called FoxP3. Mutations of the FOXP3 gene can prevent regulatory T cell development, causing the fatal autoimmune disease IPEX.

Adaptive Treg cells (also known as Tr1 cells or Th3 cells) may originate during a normal immune response.

The cell may be a Natural Killer cell (or NK cell). NK cells form part of the innate immune system. NK cells provide rapid responses to innate signals from virally infected cells in an MHC independent manner NK cells (belonging to the group of innate lymphoid cells) are defined as large granular lymphocytes (LGL) and constitute the third kind of cells differentiated from the common lymphoid progenitor generating B and T lymphocytes. NK cells are known to differentiate and mature in the bone marrow, lymph node, spleen, tonsils and thymus where they then enter into the circulation.

The CAR cells of the invention may be any of the cell types mentioned above.

T or NK cells expressing a CAR according to the invention or components thereof, may either be created ex vivo either from a patient's own peripheral blood (1st party), or in the setting of a haematopoietic stem cell transplant from donor peripheral blood (2nd party), or peripheral blood from an unconnected donor (3rd party).

Alternatively, T or NK cells expressing a CAR according to the invention or components thereof may be derived from ex vivo differentiation of inducible progenitor cells or embryonic progenitor cells to T or NK cells. Alternatively, an immortalized T-cell line which retains its lytic function and could act as a therapeutic may be used.

In all these embodiments, CAR cells are generated by introducing DNA or RNA coding for the CAR of the invention or a component(s) or a component thereof by one of many means including transduction with a viral vector, transfection with DNA or RNA.

The CAR cell of the invention may be an ex vivo T or NK cell from a subject. The T or NK cell may be from a peripheral blood mononuclear cell (PBMC) sample. T or NK cells may be activated and/or expanded prior to being transduced with nucleic acid encoding the molecules providing the CAR of the invention or a component(s) of the CAR, for example by treatment with an anti-CD3 monoclonal antibody.

The T or NK cell of the invention may be made by:
(i) isolation of a T or NK cell-containing sample from a subject or other sources listed above; and
(ii) transduction or transfection of the T or NK cells with one or more a nucleic acid sequence(s) or nucleic acid construct(s) as described above.

The T or NK cells may then by purified, for example, selected on the basis of expression of the antigen-binding domain of the antigen-binding polypeptide.

Pharmaceutical Composition

The present invention also relates to a pharmaceutical composition containing a plurality of cells expressing the CAR according to the invention or the components thereof.

The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

Method of Treatment

The present invention provides a method for treating and/or preventing a disease which comprises the step of administering the cells of the present invention (for example in a pharmaceutical composition as described above) to a subject.

A method for treating a disease relates to the therapeutic use of the cells of the present invention. Herein the cells may be administered to a subject having an existing disease or condition in order to lessen, reduce or improve at least one symptom associated with the disease and/or to slow down, reduce or block the progression of the disease.

The method for preventing a disease relates to the prophylactic use of the cells of the present invention. Herein such cells may be administered to a subject who has not yet contracted the disease and/or who is not showing any symptoms of the disease to prevent or impair the cause of the disease or to reduce or prevent development of at least one symptom associated with the disease. The subject may have a predisposition for, or be thought to be at risk of developing, the disease.

The method may involve the steps of:
(i) isolating a T or NK cell-containing sample;
(ii) transducing or transfecting such cells with a nucleic acid sequence, nucleic acid construct or vector of the invention;
(iii) administering the cells from (ii) to a subject.

The T or NK cell-containing sample may be isolated from a subject or from other sources, for example as described above. The T or NK cells may be isolated from a subject's own peripheral blood (1st party), or in the setting of a haematopoietic stem cell transplant from donor peripheral blood (2nd party), or peripheral blood from an unconnected donor (3rd party).

The present invention provides a CAR cell of the present invention for use in treating and/or preventing a disease.

The invention also relates to the use of a CAR cell of the present invention in the manufacture of a medicament for the treatment and/or prevention of a disease.

The disease to be treated and/or prevented by the methods of the present invention may be a cancerous disease, such as bladder cancer, breast cancer, colon cancer, endometrial cancer, kidney cancer (renal cell), leukaemia, lung cancer, melanoma, non-Hodgkin lymphoma, pancreatic cancer, prostate cancer and thyroid cancer.

The CAR cells of the present invention may be capable of killing target cells, such as cancer cells. The target cell may be recognisable by expression of a TAA, for example the expression of a TAA provided above in Table 1.

The CAR cells of the present invention may be capable of killing target cells, such as cancer cells, which express a low density of the TAA. Examples of TAAs which are known to be expressed at low densities in certain cancers include, but are not limited to, ROR1 in CLL, Typr-1 in melanoma and BCMA in myeloma.

The CAR cells and pharmaceutical compositions of present invention may be for use in the treatment and/or prevention of the diseases described above.

The CAR cells and pharmaceutical compositions of present invention may be for use in any of the methods described above.

The invention will now be further described by way of Examples, which are meant to serve to assist one of ordinary skill in the art in carrying out the invention and are not intended in any way to limit the scope of the invention.

EXAMPLES

Example 1—Expression of COMP CARs at the Cell Surface

Figure 5:
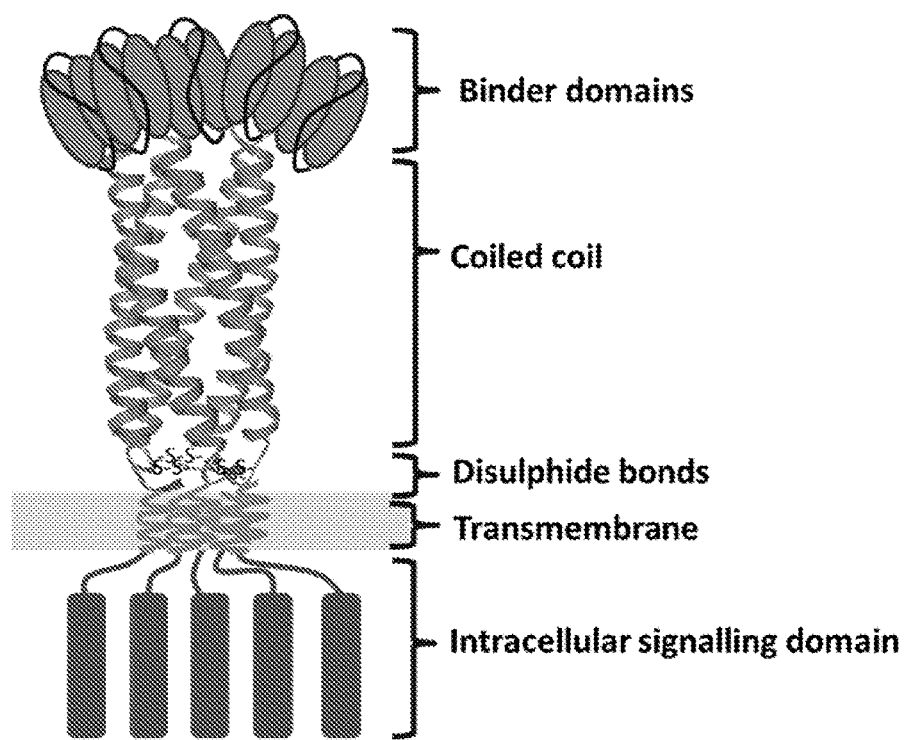
FIG. 5—Coiled coil spacer CAR. a) Schematic diagram illustrating a CAR with a pentameric coiled coil spacer derived from COMP. b) Construct map displaying the ORF of the COMP CARs and control CARs. c) Amino acid sequence of the ORF of the anti-CD33 COMP CAR and anti-ROR-1 COMP CAR. d) DNA sequence of the ORF of the anti-CD33 COMP CAR and anti-ROR-1 COMP CAR.
Figure 5:
Figure 5:
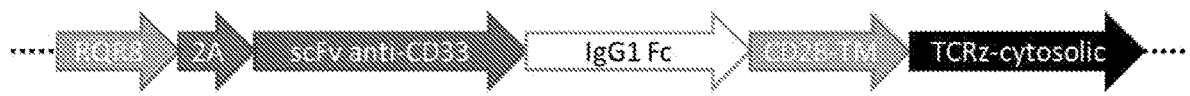
Figure 5:
Figure 5:
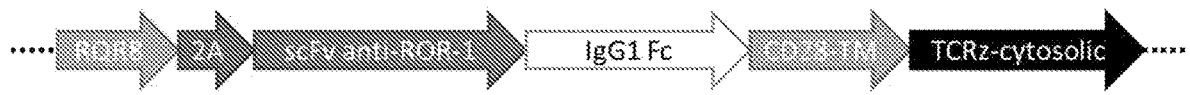

A murine T-cell line was transduced with the anti-CD33 COMP CAR (amino acid sequence shown in FIG. 5c and nucleic acid sequence shown in FIG. 5d) or anti-CD33 IgG1 CAR.

Figure 6:
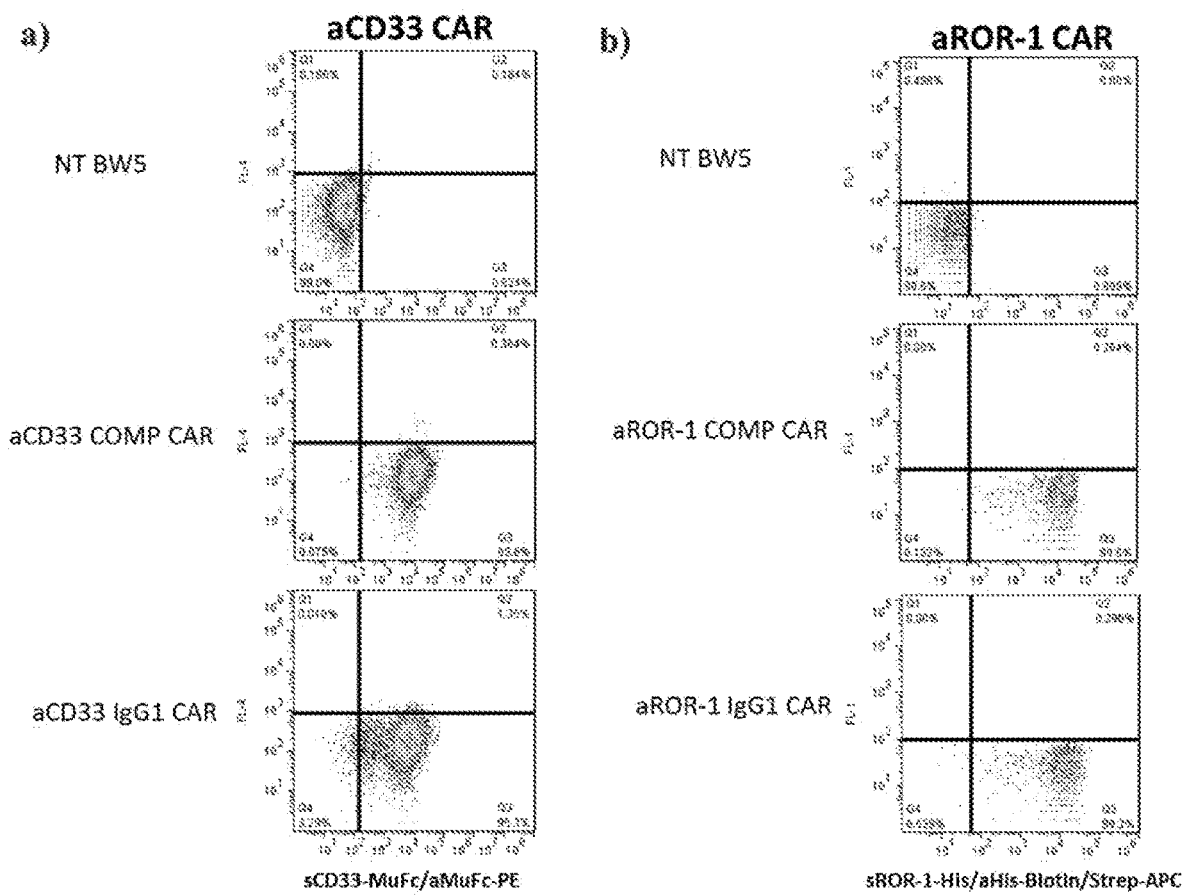
FIG. 6—Coiled coil CAR surface expression levels. a) A murine T-cell line was transduced with the anti-CD33 COMP CAR or anti-CD33 IgG1 CAR. These cells were then stained with chimeric soluble CD33 fused to murine Fc IgG2a before a secondary stain with anti-mouse IgG PE. b) A murine T-cell line was transduced with the anti-ROR-1 COMP CAR or anti-ROR-1 IgG1 CAR. These cells were then stained with soluble His tagged ROR-1 followed by a secondary stain with anti-His-biotin and then a third stain with streptavidin-APC.

These cells were then stained with chimeric soluble CD33 fused to murine Fc IgG2a before a secondary stain with anti-mouse IgG PE (FIG. 6a)

A murine T-cell line was transduced with the anti-ROR-1 COMP CAR CAR (amino acid sequence shown in FIG. 5c and nucleic acid sequence shown in FIG. 5d) or anti-ROR-1 IgG1 CAR.

These cells were then stained with soluble His tagged ROR-1 followed by a secondary stain with anti-His-biotin and then a third stain with streptavidin-APC (FIG. 6b).

All four CARs were successfully expressed on the cell surface. These data also demonstrate that that the CAR binding domain is orientated in a way that does not impede ligand binding when linked to a COMP spacer.

Example 2—Stimulation of COMP CAR T-Cells with Immobilised Ligand

T-cells with beads coated with immobilised ligand were used to stimulate COMP ROR-1 CAR T-cells. To achieve this, soluble His-tag ROR-1 was constructed and expressed. Supernatants containing these soluble ligands were then incubated at various concentrations with a set number of anti-His beads. The beads were then washed to remove unbound ligand and these beads were used to stimulate T-cells transduced with either the COMP CAR platforms or an equivalent CAR with an IgG spacer.

Figure 7:
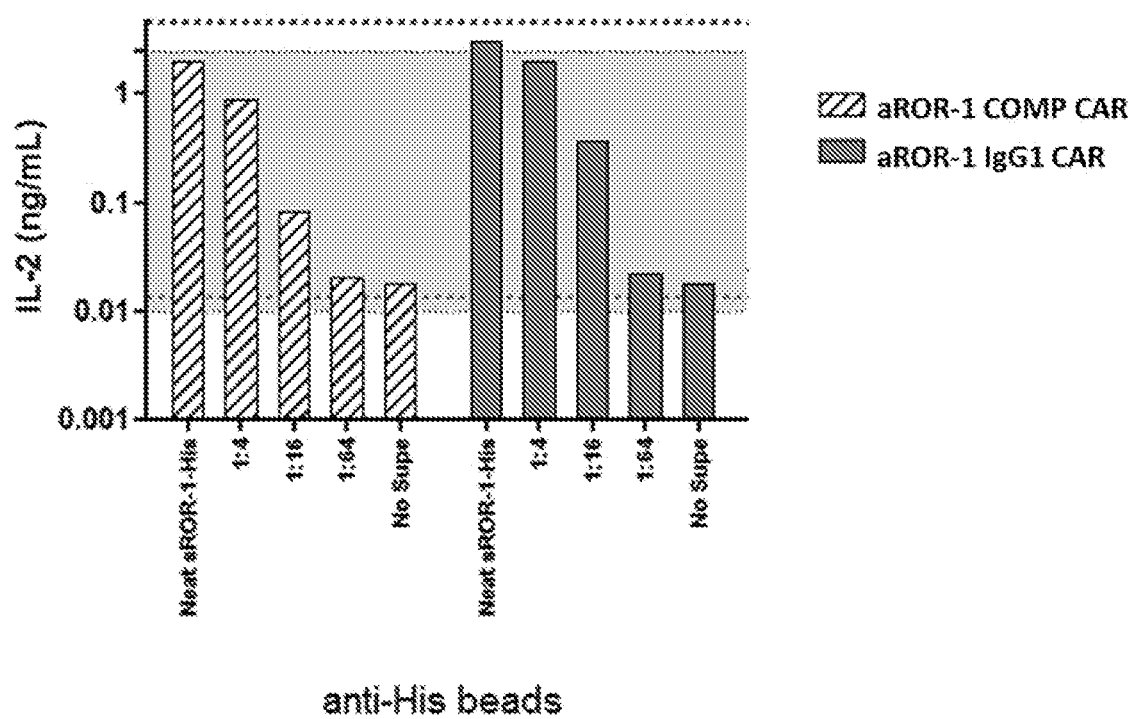
FIG. 7—Stimulation of anti-ROR-1 COMP CAR T-cells with immobilised ligand. Transduced murine T-cells were co-cultured with anti-His beads that were pre-coated with different concentrations of soluble His tagged ROR-1 supernatant. The amount of IL-2 in the co-culture supernatant was analysed after 16-24 hours via ELISA.

Transduced murine T-cells were co-cultured with anti-His beads that were pre-coated with different concentrations of soluble His tagged ROR-1 supernatant. The amount of IL-2 in the co-culture supernatant was analysed after 16-24 hours via ELISA (FIG. 7).

Example 3—Expression Levels of ROR-1 Target Cells

Figure 8:
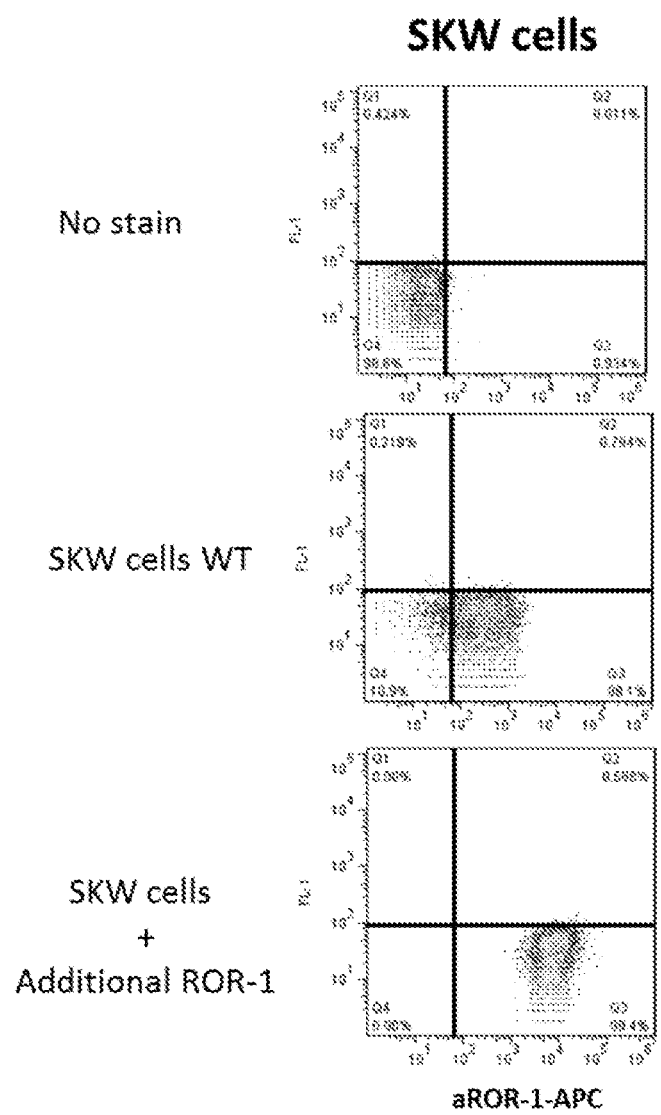
FIG. 8—Expression levels of ROR-1 on target cells. The SKW cell line naturally expresses low levels of ROR-1. These cells were transduced with ROR-1 to increase the expression levels. These cells were stained with anti-ROR-1 APC and compared to non-stained cells.

The SKW cell line naturally expresses low levels of ROR-1. These cells were transduced with ROR-1 to increase the expression levels. These cells were stained with anti-ROR-1 APC and compared to non-stained cells (FIG. 8).

Figure 9:
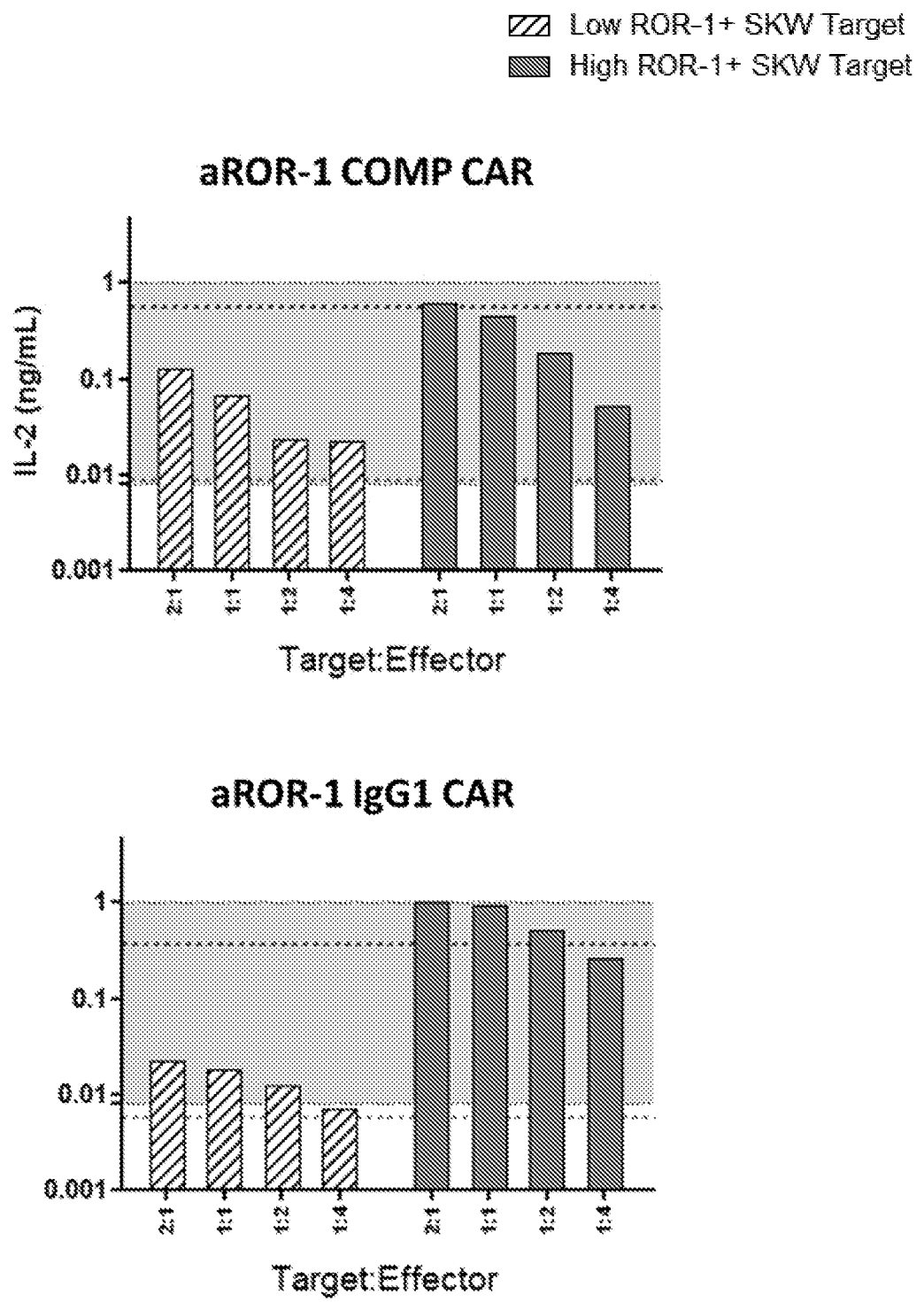
FIG. 9—Stimulation of anti-ROR-1 COMP CAR T-cells with ROR-1 positive SKW cells. Transduced murine T-cells were co-cultured with SKW target cells that express the ROR-1 ligand at low or high density. T-cells were maintained at a constant number and the number of target cells was varied. The amount of IL-2 in the co-culture supernatant was analysed after 16-24 hours via ELISA. The grey shaded region denotes the standard curve range for that experiment. The dotted blue line is the average IL-2 secretion from PMA and Ionomycin stimulation. The red dotted line is the average IL-2 detected from cultures of just T-cells (non-stimulated).
Figure 10:
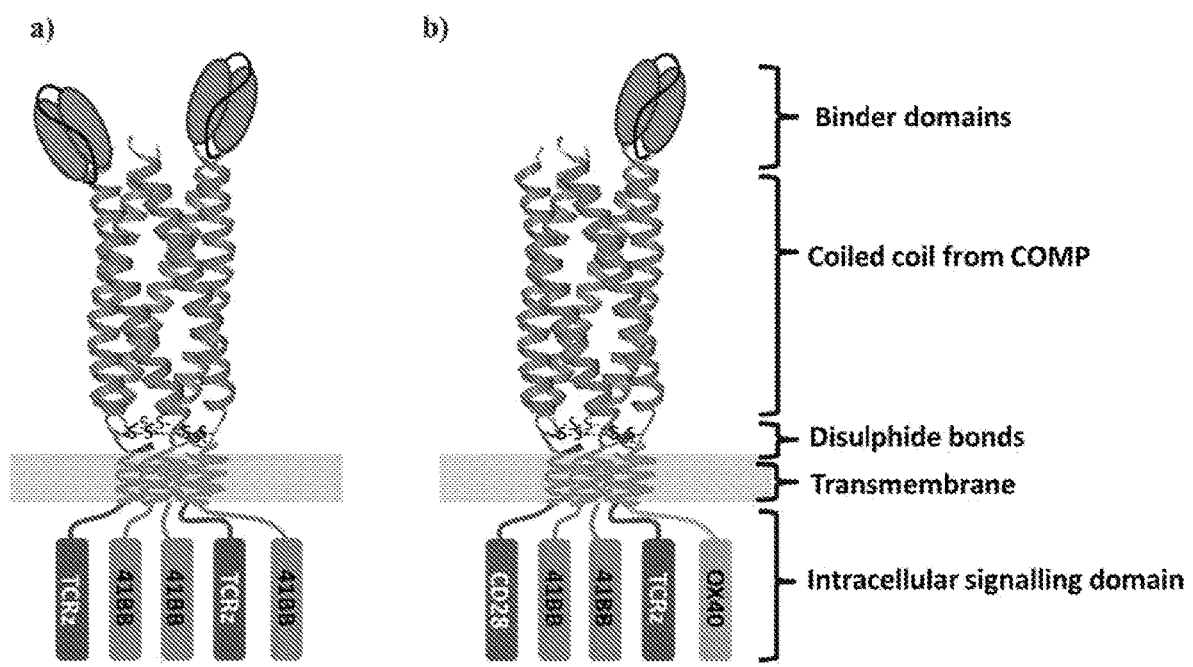
FIG. 10—Coiled coil CAR designs. a) Schematic diagram illustrating a CAR made up of a CAR-forming polypeptide and an accessory polypeptide. The CAR-forming polypeptide provides signal one to the T-cell and consists of a scFv binder on the N-terminus followed by a COMP spacer, transmembrane and TCRz. The accessory polypeptide provides signal three to the T-cell and consists of no N-terminal ligand binder but begins with the COMP spacer followed by a transmembrane and the signalling motif of 41BB; b) Schematic diagram illustrating another coiled coil CAR system which includes a CAR-forming polypeptide and two accessory polypeptides. The CAR-forming polypeptide provides signal one to the T-cell and consists of a scFv binder on the N-terminus followed by a COMP spacer, transmembrane and TCRz. The first accessory polypeptide provides signal two to the T-cell and consists of no N-terminal ligand binder but begins with the COMP spacer followed by a transmembrane and the signalling motif of CD28. The second accessory polypeptide provides signal three to the T-cell and consists of no N-terminal ligand binder but begins with the COMP spacer followed by a transmembrane and the signalling motif of 41BB. "S" denotes disulfide bonds. This arrangement allows the signalling endodomains to be in trans in a membrane-proximal location, leading to better signalling; c) Schematic diagram illustrating another coiled coil CAR system in which the ratio of scFv:coil is much less than that of coil:signal, so each scFv is attached to may signalling elements. This is an amplification system: by limiting the scFv to one per complex, each engaged ligand will signal through 5 TCRz chains (two ligands through 10TCRz). This is as opposed to the traditional dimeric CARs where two ligands signal through 2TCRz chains. This system will essentially increase triggering power by 5 fold; d) Schematic diagram illustrating another coiled coil CAR system which comprises more endodomains than a third generation CAR. The coiled coil spacer enables the introduction of two additional signalling domains ("EXTRA") over and above a traditional third generation CAR; e) Schematic diagram illustrating another coiled coil CAR signalling system which comprises multiple targets (here two target-binding specificities are shown: one which binds ligand A and one which binds ligand B). This arrangement is an alternative architecture for a TanCAR; f) Schematic diagram illustrating another coiled coil CAR system which comprises an element which forms a link such a bridging di-sulphides with another coiled-coil spacer CAR giving an engaged complex which further increases the valency of the scFv:signalling domain. Like the arrangement shown in FIG. 10c), this is an amplification system. Each engaged complex will signal through 10 TCRz chains. As opposed to the traditional dimeric CARs that signal through 2 TCRz chains. This system will essentially increase triggering power by 5 fold. Replacing the IgG hinge with a trimeric coiled coil structure would increase this to just short of 8 fold, whereas a tetrameric coiled coil would increase it by 10 fold.
Figure 10C:
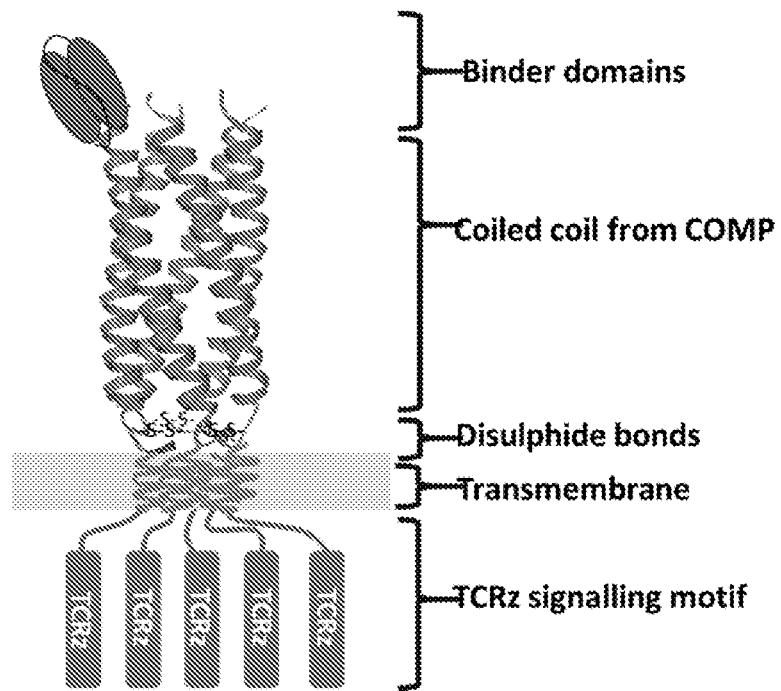
Figure 10D:
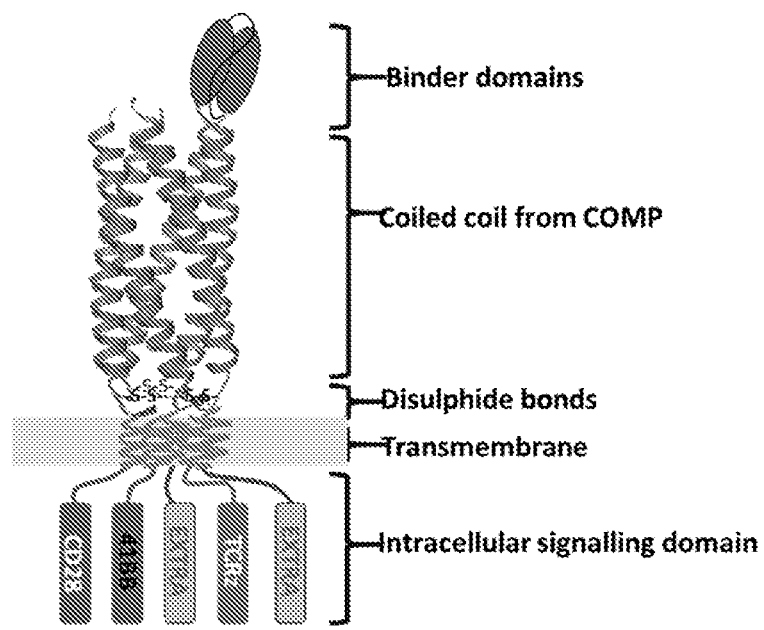
Figure 10E:
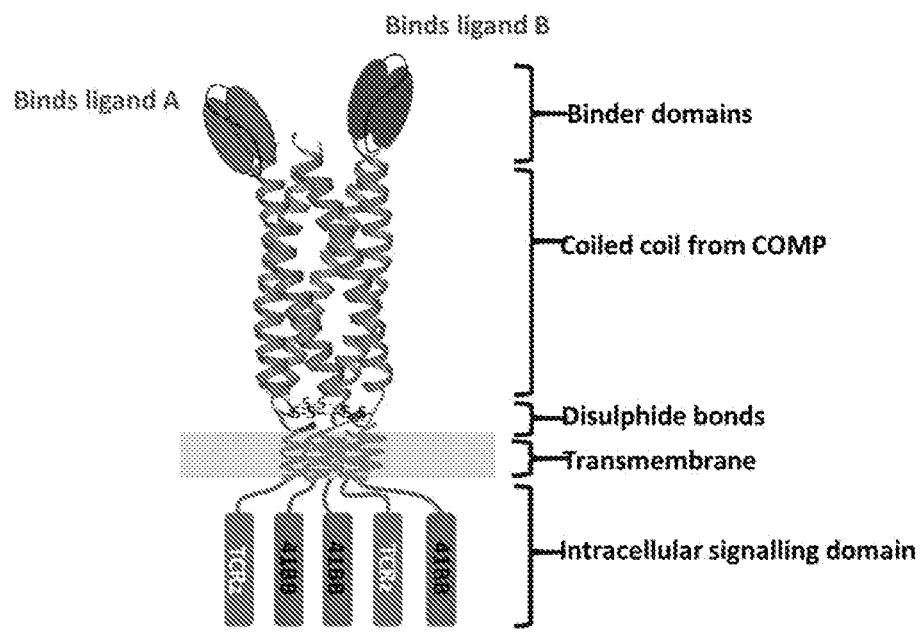
Figure 10F:
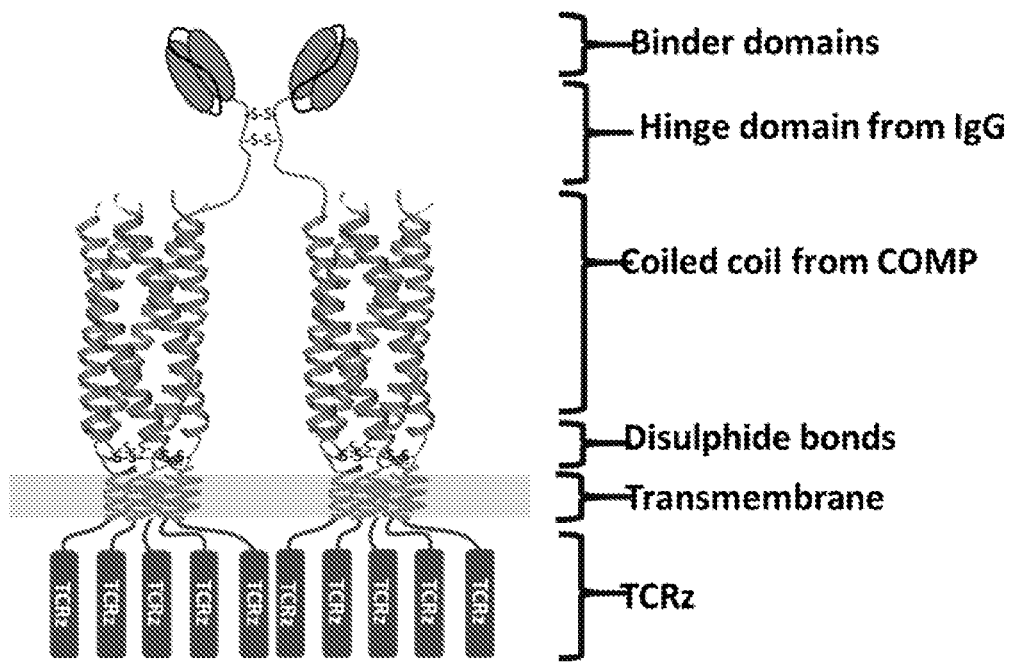

Example 4—Stimulation of Anti-ROR-1 COMP CAR T-Cells with ROR-1 Positive SKW Cells Transduced murine T-cells (described in Examples 1 and 2) were co-cultured with SKW target cells that express the ROR-1 ligand at either a low or a high density. T-cells were maintained at a constant number and the target cells were varied. The amount of IL-2 in the co-culture supernatant was analysed after 16-24 hours via ELISA (FIG. 9).

Higher levels of IL-2 were detected when the anti-ROR-1 COMP CAR T cells were co-cultured with SKW target cells expressing a low density of ROR-1 ligand compared to the anti-ROR-1 IgG1 CAR.

Both CARs were able to initiate an activation response with SKW-high target cells.

Example 5—Truncation of the COMP Spacer

The aROR-1 CAR with a COMP spacer was truncated from its original length of 45 amino acids. These COMP truncated constructs were transfected into 293T cells and then stained for CAR surface expression with sROR-1 His followed by and anti-His-Biotin followed by a streptavidin-PE.Cy7. These cells were also stained for the RQR8 marker with an anti-CD34-FITC antibody. These FACS plots show stable surface expression of various truncated forms of the COMP spacer, displaying the ability to vary the length of the coiled coil spacer by one to a few amino acids at a time (FIG. 11).

Example 6—Comparison of Multimeric Coiled-Coil Spacer CARs with a Classical Dimeric CAR In order to compare the function of coiled-coil spacers CARs of the invention with a conventional CAR, a series of constructs were made with the same antigen-binding domains and equivalent endodomains, but with different spacers, leading to a completely different CAR structure. The different CARs are shown in FIG. 12.

All CARs comprised an anti-CD19 antigen-binding domain based on fmc63 and a "second generation" endodomain comprising 41BB and CD3zeta endodomains. The following formats ere tested:
  a) a heteromultimeric CAR which comprises: a polypeptide having an anti-CD19 antigen binding domain; a coiled-coil spacer domain and a CD3zeta endodomain; and an accessory polypeptide having a coiled-coil spacer domain and a 41BB endodomain (FIG. 12A);
  b) a homomultimeric CAR made up of polypeptides comprising an anti-CD19 antigen binding domain; a coiled-coil spacer domain and a combined 41BB/CD3zeta endodomain (FIG. 12B); and
  c) a classical second generation homodimeric CAR which comprises two polypeptides having an anti-CD19 antigen-binding domain, a CD8 stalk spacer domain and a combined 41BB/CD3zeta endodomain (FIG. 12C).

Figure 12:
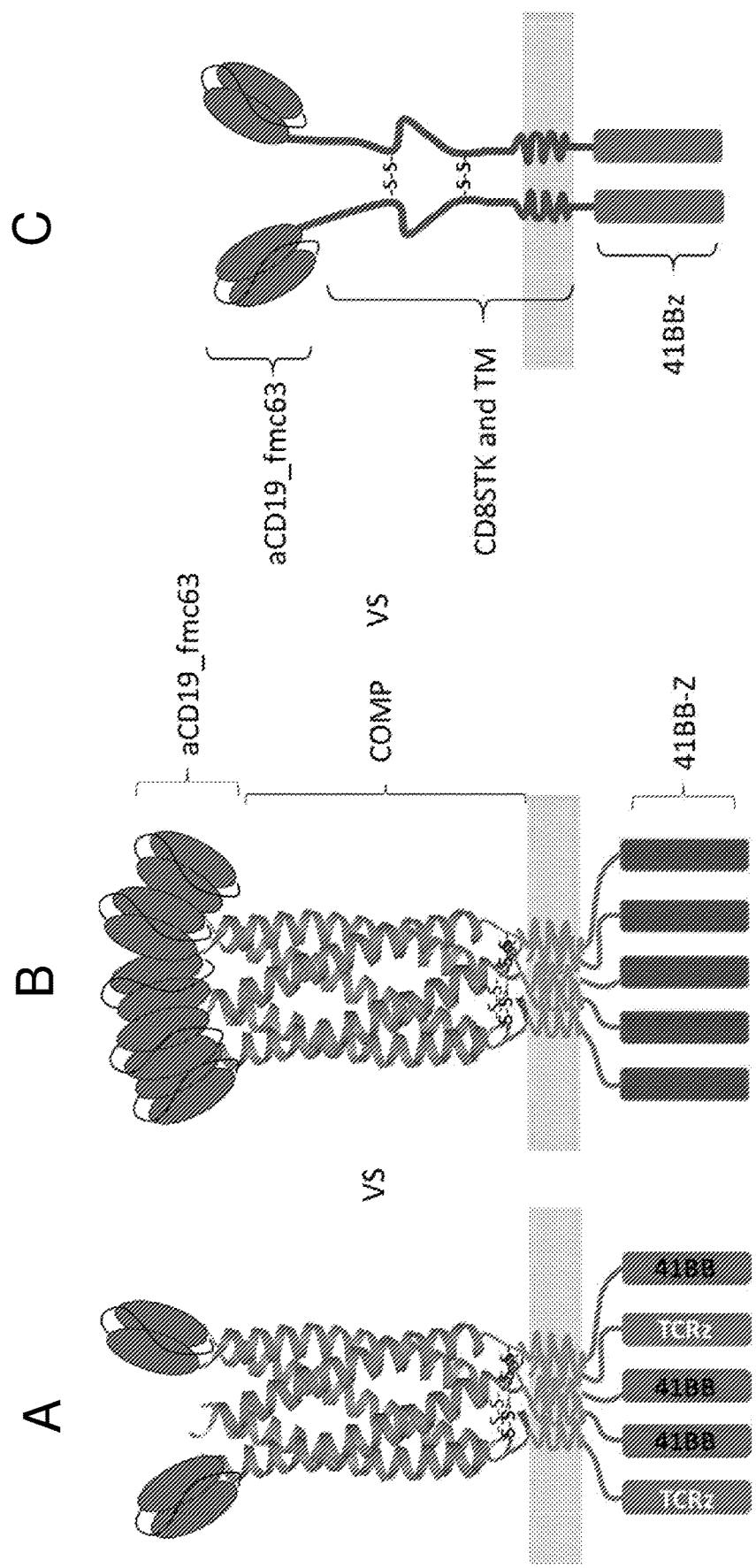
FIG. 12—Schematic diagram showing the multimeric and classical CARs tested in Example 6
A) a heteromultimeric CAR which comprises: a polypeptide having an anti-CD19 antigen binding domain; a coiled-coil spacer domain and a CD3zeta endodomain; and an accessory polypeptide having a coiled-coil spacer domain and a 41BB endodomain. The CAR is encoded by a bicistronic construct having the structure: aCD19fmc63-COMP-CD28tmZ-2A-COMP-CD28tm-41BB. In this CAR structure, the 41BB and TCRzeta signalling motifs are in parallel.
B) a homomutimeric CAR made up of polypeptides comprising an anti-CD19 antigen binding domain; a coiled-coil spacer domain and a combined 41BB/CD3zeta endodomain. The CAR is encoded by a construct having the structure: aCD19fmc63-COMP-CD8TM-41BB-Z. In this CAR structure, the 41BB and TCRzeta signalling motifs are in sequential order.
C) a classical second generation homodimeric CAR which comprises two polypeptides having an anti-CD19 antigen-binding domain, a CD8 stalk spacer domain and a combined 41BB/CD3zeta endodomain. The CAR is encoded by a bicistronic construct which also encodes the suicide gene RQR8. The construct has the structure: RQR8-2A-aCD19fmc63-CD8STK-41BBZ.

Vectors encoding the CAR illustrated in FIG. 12 were RD114-pseudotyped retrovirus encoding the various CAR structures was produced.

T cells were depleted of CD56-expressing cells and co-cultured with an equal number of SupT1 to achieve an effector:target ratio of 1:1. Prior to analysis by flow cytometry, an equal number of fluorescent counting beads was added to each co-culture to allow normalization of cell numbers and to account for any differences in uptake volumes. CAR-mediated cytotoxicity was assessed by flow cytometry as follows: T cells were differentiated from tumour cells by staining for CD3 expression vs FCS and tumour cells identified by their lack of CD3 and higher FCS signal. Viability was assessed by staining with the dead cell exclusion dye 7-AAD and viable cells defined as those which did not uptake the dye. Viable tumour cells were enumerated for each co-culture condition and percentage cytotoxicity was calculated by normalizing the number of viable tumour cells to that recovered from co-cultures carried out with non-transduced PBMCs (100%). Killing of targets cells was assessed at day 2 and 5.

Figure 13:
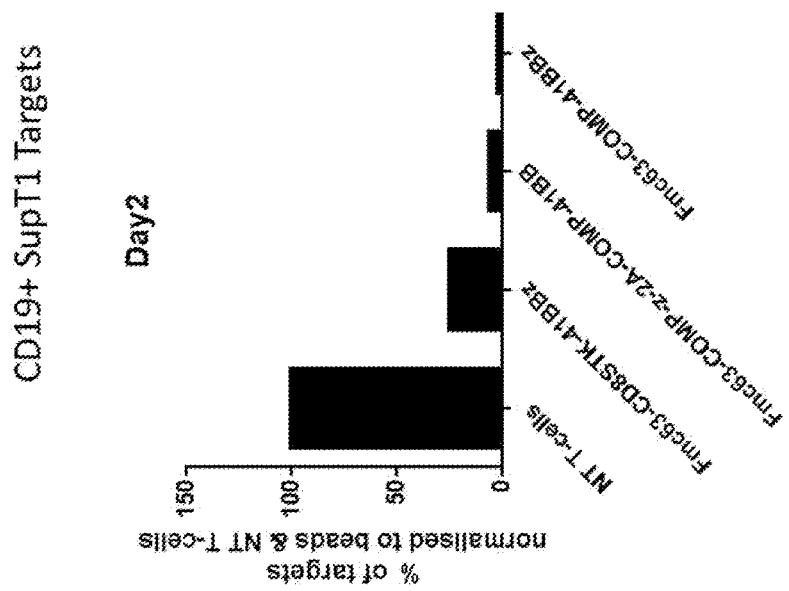
FIG. 13—Killing of CD19+ SupT1 target cells by the CARs shown in FIG. 12 at day 2.
Figure 13:
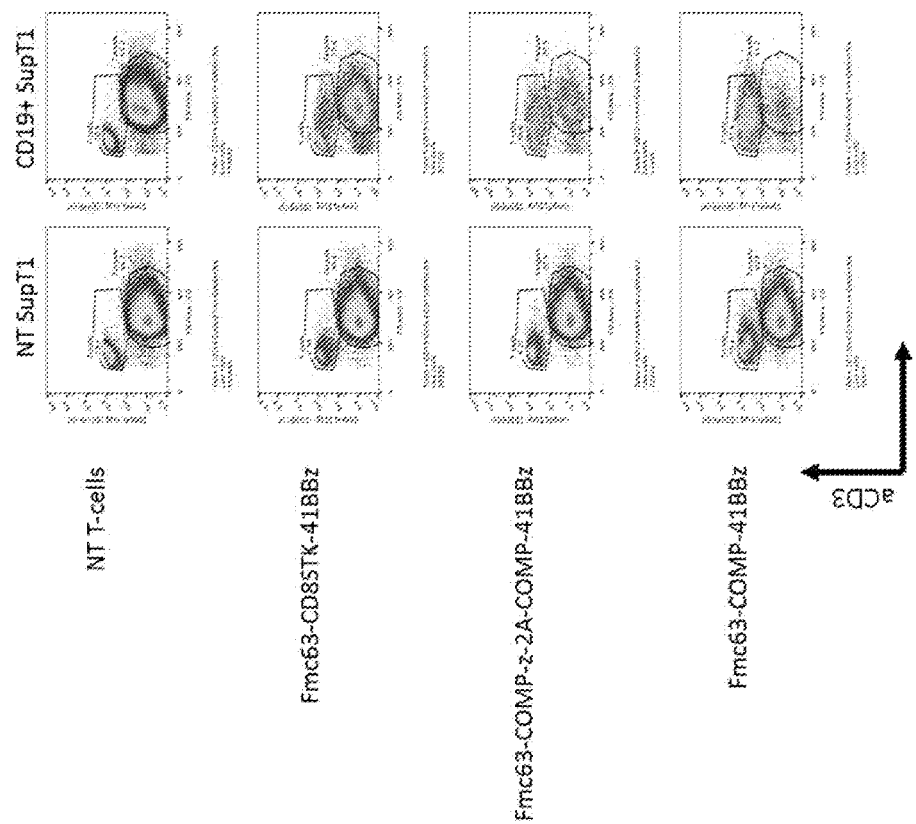
Figure 14:
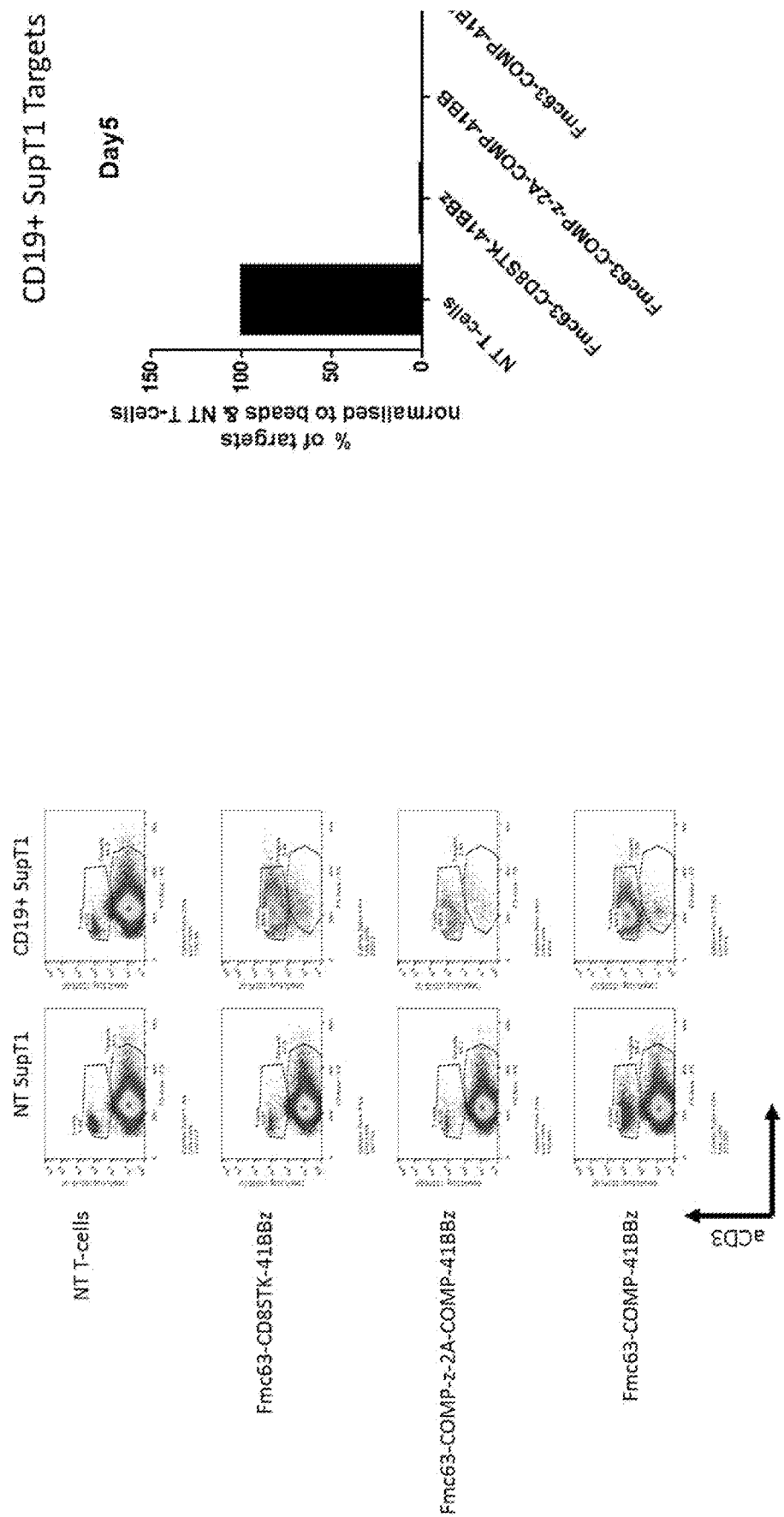
FIG. 14—Killing of CD19+ SupT1 target cells by the CARs shown in FIG. 12 at day 5.

The results are shown in FIG. 13 (day 2) and FIG. 14 (day 5). After two days, II three CAR structures showed killing of CD19+ SupT1 target cells. The two multimeric CARs showed superior killing to the equivalent classical homodimeric CAR. The homomultimeric CAR (Fmc63-COMP-41BBz) showed the most killing. At day 5, some residual target cells remained with the classical homodimeric CAR (Fmc63-CD8STK-41BBz) but viable target cells were virtually undetectable for both the multimeric CARs.

Example 7—Production and Testing of Coiled-Coil SuperCARs

A major challenge for CAR technologies is the detection of antigens which are present at low densities on target cells. In order to address this issue, the present inventors have designed "SuperCARs" based on the coiled-coil spacer format which recruit multiple TCRzeta chains for each antigen interaction.

The intracellular part of the polypeptide making up the coiled-coil CAR structure comprises a plurality of heterodimerization domains, each or which is capable of interacting with one or more intracellular signalling components which comprises one or more intracellular signalling domains.

In the constructs illustrated in FIG. 15, intracellular dimerization is between dimerization and docking domain (DDD1) and anchoring domain (AD1). Each polypeptide making up the coiled-coil spacer CAR comprises four separate AD1 domains. A coiled-coil CAR comprising 5 polypeptides will therefore comprise 20 AD1 domains The coiled coil SuperCAR was tested in combination with different signalling components having 0 or 2 copies of the TCR zeta signalling domain. As DDD1 binds AD1 in a 2:1 stoichiometry, these signalling domains give 0 and 80 copies of the TCR zeta domain respectively for each 5-polypeptide coiled-coil CAR targeting component.

As a control, a classical homodimeric anti-CD19 CAR was used (FIG. 15: aCD19-IgGFc-Z) with the same antigen-binding domain.

The murine T-cell line BW5 was transduced with each CAR and challenged with SupT1 cells expressing the cognate antigen (CD19) at different concentrations: low, mid and high. These SupT1 cells were engineered to express CD19 at different levels by the use of suboptimal signal peptides and/or the introduction of cytoplasmic retention motifs derived from Tyrp-1 (inserted proximal to the membrane) or glycoprotein E3-19k from adenovirus (inserted on the C-terminus). IL-2 release was measured after antigen challenge.

Figure 16:
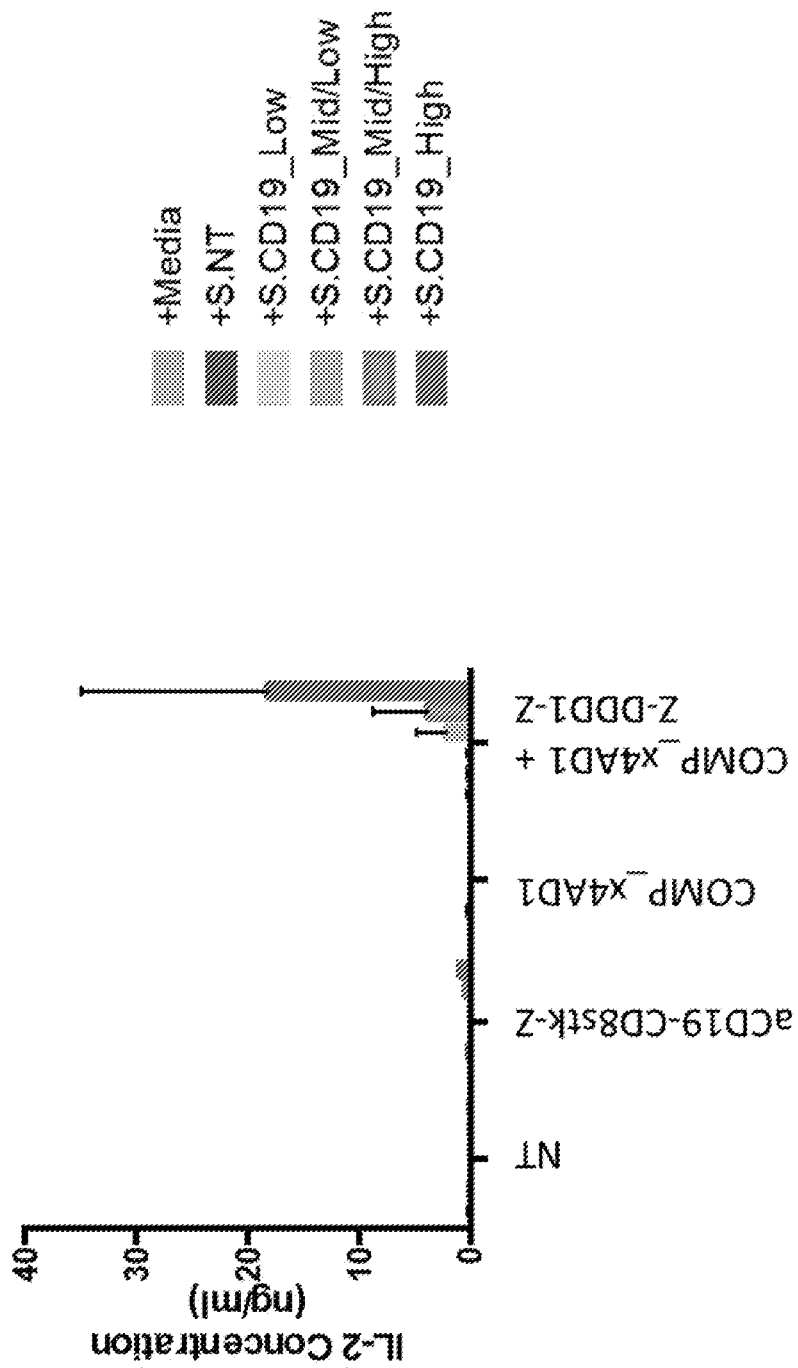
FIG. 16—IL2 release following challenge with target cells expressing the cognate antigen (CD19) at different concentrations: low, mid and high.

The results are shown in FIG. 16. It was found that coiled-coil the superCAR comprising 80 copies of TCR zeta per 5-mer coiled-coil CAR gave a much greater response to antigen than the equivalent classical CAR comprising two copies of TCR zeta per molecule.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, cell biology or related fields are intended to be within the scope of the following claims.

The invention claimed is:

1. A pentameric chimeric antigen receptor (CAR) comprising five CAR-forming polypeptides, wherein the CAR-forming polypeptides comprise in order from the amino terminus:
   (i) an antigen-binding domain,
   (ii) a cartilage-oligomeric matrix protein (COMP) coiled-coil spacer domain,
   (iii) a transmembrane domain and
   (iv) an endodomain comprising an intracellular signalling domain or an endodomain that interacts with an intracellular signaling molecule.

2. The pentameric CAR according claim 1 wherein the CAR-forming polypeptides comprise different intracellular signalling domains.

3. The pentameric CAR according to claim 1 wherein at least two of the CAR-forming polypeptides comprise different antigen-binding domains.

4. A nucleic acid construct which encodes a CAR-forming polypeptide, wherein the CAR-forming polypeptide comprises in order from the amino terminus:
   (i) an antigen-binding domain,
   (ii) a cartilage-oligomeric matrix protein (COMP) coiled-coil spacer domain,
   (iii) a transmembrane domain and
   (iv) an endodomain comprising an intracellular signalling domain or an endodomain that interacts with an intracellular signaling molecule.

5. A vector which comprises a nucleic acid construct according to claim 4.

6. A cell which expresses a pentameric CAR according claim 1.

7. The cell according to claim 6 which is a T cell or NK cell.

8. A pharmaceutical composition comprising the cell according to claim 6.

9. A method for treating a disease comprising the step of administering the cell according to claim 7 to a subject in need thereof.

10. The method according to claim 9 wherein the disease is cancer.

11. A method for making a cell that expresses a pentameric CAR, which comprises the step of introducing a nucleic acid construct according to 4 into the cell.

12. The pentameric CAR according to claim 1, wherein the COMP coiled-coil spacer domain is the COMP coiled-*coli* spacer domain shown as SEQ ID No. 1.

13. The nucleic acid construct according to claim 4, wherein the COMP coiled-coil spacer domain is the COMP coiled-*coli* spacer domain shown as SEQ ID No. 1.

* * * * *

UNITED STATES PATENT AND TRADEMARK OFFICE
CERTIFICATE OF CORRECTION

Page 1 of 2

PATENT NO. : 11,058,722 B2
APPLICATION NO. : 15/560558
DATED : July 13, 2021
INVENTOR(S) : Martin Pulé et al.

It is certified that error appears in the above-identified patent and that said Letters Patent is hereby corrected as shown below:

In the Claims

At Column 63, Lines 50-51, "the amino terminus:" should be -- an amino terminus: --.

At Column 63, Line 55, "domain and" should be -- domain, and --.

At Column 63, Line 57, "an endodomain" should be -- the endodomain --.

At Column 63, Line 59, "according claim" should be -- according to claim --.

At Column 63, Line 67, "the amino terminus:" should be -- an amino terminus: --.

At Column 64, Line 51, "domain and" should be -- domain, and --.

At Column 64, Line 53, "an endodomain" should be -- the endodomain --.

At Column 64, Line 55, "a nucleic acid construct" should be -- the nucleic acid construct --.

At Column 64, Line 57, "a pentameric CAR" should be -- the pentameric CAR --.

At Column 64, Line 57, "according" should be -- according to --.

At Column 65, Line 1, "a cell" should be -- the cell --.

At Column 65, Lines 1-2, "a pentameric CAR," should be -- the pentameric CAR, --.

At Column 65, Lines 2-3, "a nucleic acid construct according to 4" should be -- the nucleic acid construct according to claim 4 --.

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*

At Column 65, Lines 5-6, "coiled-coli" should be -- coiled-coil --.

At Column 65, Line 9, "coiled-coli" should be -- coiled-coil --.

SEQUENCE LISTING

```
<160> NUMBER OF SEQ ID NOS: 49

<210> SEQ ID NO 1
<211> LENGTH: 45
<212> TYPE: PRT
<213> ORGANISM: Artificial Sequence
<220> FEATURE:
<223> OTHER INFORMATION: coiled coil domain

<400> SEQUENCE: 1

Asp Leu Gly Pro Gln Met Leu Arg Glu Leu Gln Glu Thr Asn Ala Ala
1               5                   10                  15

Leu Gln Asp Val Arg Glu Leu Leu Arg Gln Gln Val Arg Glu Ile Thr
            20                  25                  30

Phe Leu Lys Asn Thr Val Met Glu Cys Asp Ala Cys Gly
        35                  40                  45

<210> SEQ ID NO 2
<211> LENGTH: 21
<212> TYPE: PRT
<213> ORGANISM: Artificial Sequence
<220> FEATURE:
<223> OTHER INFORMATION: signal peptide derived from TCR beta chain

<400> SEQUENCE: 2

Met Gly Thr Ser Leu Leu Cys Trp Met Ala Leu Cys Leu Leu Gly Ala
1               5                   10                  15
```

Asp His Ala Asp Gly
        20

<210> SEQ ID NO 3
<211> LENGTH: 21
<212> TYPE: PRT
<213> ORGANISM: Artificial Sequence
<220> FEATURE:
<223> OTHER INFORMATION: signal peptide derived from IgG1

<400> SEQUENCE: 3

Met Ser Leu Pro Val Thr Ala Leu Leu Leu Pro Leu Ala Leu Leu Leu
1               5                   10                  15

His Ala Ala Arg Pro
        20

<210> SEQ ID NO 4
<211> LENGTH: 20
<212> TYPE: PRT
<213> ORGANISM: Artificial Sequence
<220> FEATURE:
<223> OTHER INFORMATION: signal peptide derived from CD8a

<400> SEQUENCE: 4

Met Ala Val Pro Thr Gln Val Leu Gly Leu Leu Leu Leu Trp Leu Thr
1               5                   10                  15

Asp Ala Arg Cys
        20

<210> SEQ ID NO 5
<211> LENGTH: 112
<212> TYPE: PRT
<213> ORGANISM: Artificial Sequence
<220> FEATURE:
<223> OTHER INFORMATION: CD3 Z endodomain

<400> SEQUENCE: 5

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 6
<211> LENGTH: 152
<212> TYPE: PRT
<213> ORGANISM: Artificial Sequence
<220> FEATURE:
<223> OTHER INFORMATION: CD28 and CD3 Zeta endodomains

<400> SEQUENCE: 6

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser Arg Val Lys Phe Ser Arg Ser Ala
            35                  40                  45

Asp Ala Pro Ala Tyr Gln Gln Gly Gln Asn Gln Leu Tyr Asn Glu Leu
        50                  55                  60

Asn Leu Gly Arg Arg Glu Glu Tyr Asp Val Leu Asp Lys Arg Arg Gly
65                  70                  75                  80

Arg Asp Pro Glu Met Gly Gly Lys Pro Arg Arg Lys Asn Pro Gln Glu
                85                  90                  95

Gly Leu Tyr Asn Glu Leu Gln Lys Asp Lys Met Ala Glu Ala Tyr Ser
            100                 105                 110

Glu Ile Gly Met Lys Gly Glu Arg Arg Arg Gly Lys Gly His Asp Gly
            115                 120                 125

Leu Tyr Gln Gly Leu Ser Thr Ala Thr Lys Asp Thr Tyr Asp Ala Leu
        130                 135                 140

His Met Gln Ala Leu Pro Pro Arg
145                 150

<210> SEQ ID NO 7
<211> LENGTH: 188
<212> TYPE: PRT
<213> ORGANISM: Artificial Sequence
<220> FEATURE:
<223> OTHER INFORMATION: CD28, OX40 and CD3 Zeta endodomains

<400> SEQUENCE: 7

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser Arg Asp Gln Arg Leu Pro Pro Asp
            35                  40                  45

Ala His Lys Pro Pro Gly Gly Gly Ser Phe Arg Thr Pro Ile Gln Glu
        50                  55                  60

Glu Gln Ala Asp Ala His Ser Thr Leu Ala Lys Ile Arg Val Lys Phe
65                  70                  75                  80

Ser Arg Ser Ala Asp Ala Pro Ala Tyr Gln Gln Gly Gln Asn Gln Leu
                85                  90                  95

Tyr Asn Glu Leu Asn Leu Gly Arg Arg Glu Glu Tyr Asp Val Leu Asp
            100                 105                 110

Lys Arg Arg Gly Arg Asp Pro Glu Met Gly Gly Lys Pro Arg Arg Lys
            115                 120                 125

Asn Pro Gln Glu Gly Leu Tyr Asn Glu Leu Gln Lys Asp Lys Met Ala
        130                 135                 140

Glu Ala Tyr Ser Glu Ile Gly Met Lys Gly Glu Arg Arg Arg Gly Lys
145                 150                 155                 160

Gly His Asp Gly Leu Tyr Gln Gly Leu Ser Thr Ala Thr Lys Asp Thr
                165                 170                 175

Tyr Asp Ala Leu His Met Gln Ala Leu Pro Pro Arg
            180                 185

<210> SEQ ID NO 8
<211> LENGTH: 38
<212> TYPE: PRT
<213> ORGANISM: Artificial Sequence
<220> FEATURE:

<223> OTHER INFORMATION: ICOS endodomain

<400> SEQUENCE: 8

Cys Trp Leu Thr Lys Lys Lys Tyr Ser Ser Ser Val His Asp Pro Asn
1               5                   10                  15

Gly Glu Tyr Met Phe Met Arg Ala Val Asn Thr Ala Lys Lys Ser Arg
            20                  25                  30

Leu Thr Asp Val Thr Leu
        35

<210> SEQ ID NO 9
<211> LENGTH: 48
<212> TYPE: PRT
<213> ORGANISM: Artificial Sequence
<220> FEATURE:
<223> OTHER INFORMATION: CD27 endodomain

<400> SEQUENCE: 9

Gln Arg Arg Lys Tyr Arg Ser Asn Lys Gly Glu Ser Pro Val Glu Pro
1               5                   10                  15

Ala Glu Pro Cys His Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
        35                  40                  45

<210> SEQ ID NO 10
<211> LENGTH: 111
<212> TYPE: PRT
<213> ORGANISM: Artificial Sequence
<220> FEATURE:
<223> OTHER INFORMATION: BTLA endodomain

<400> SEQUENCE: 10

Arg Arg His Gln Gly Lys Gln Asn Glu Leu Ser Asp Thr Ala Gly Arg
1               5                   10                  15

Glu Ile Asn Leu Val Asp Ala His Leu Lys Ser Glu Gln Thr Glu Ala
            20                  25                  30

Ser Thr Arg Gln Asn Ser Gln Val Leu Leu Ser Glu Thr Gly Ile Tyr
        35                  40                  45

Asp Asn Asp Pro Asp Leu Cys Phe Arg Met Gln Glu Gly Ser Glu Val
    50                  55                  60

Tyr Ser Asn Pro Cys Leu Glu Glu Asn Lys Pro Gly Ile Val Tyr Ala
65                  70                  75                  80

Ser Leu Asn His Ser Val Ile Gly Pro Asn Ser Arg Leu Ala Arg Asn
                85                  90                  95

Val Lys Glu Ala Pro Thr Glu Tyr Ala Ser Ile Cys Val Arg Ser
            100                 105                 110

<210> SEQ ID NO 11
<211> LENGTH: 188
<212> TYPE: PRT
<213> ORGANISM: Artificial Sequence
<220> FEATURE:
<223> OTHER INFORMATION: CD30 endodomain

<400> SEQUENCE: 11

His Arg Arg Ala Cys Arg Lys Arg Ile Arg Gln Lys Leu His Leu Cys
1               5                   10                  15

Tyr Pro Val Gln Thr Ser Gln Pro Lys Leu Glu Leu Val Asp Ser Arg
            20                  25                  30

```
Pro Arg Arg Ser Ser Thr Gln Leu Arg Ser Gly Ala Ser Val Thr Glu
            35                  40                  45

Pro Val Ala Glu Glu Arg Gly Leu Met Ser Gln Pro Leu Met Glu Thr
 50                  55                  60

Cys His Ser Val Gly Ala Ala Tyr Leu Glu Ser Leu Pro Leu Gln Asp
 65                  70                  75                  80

Ala Ser Pro Ala Gly Gly Pro Ser Ser Pro Arg Asp Leu Pro Glu Pro
                 85                  90                  95

Arg Val Ser Thr Glu His Thr Asn Asn Lys Ile Glu Lys Ile Tyr Ile
            100                 105                 110

Met Lys Ala Asp Thr Val Ile Val Gly Thr Val Lys Ala Glu Leu Pro
            115                 120                 125

Glu Gly Arg Gly Leu Ala Gly Pro Ala Glu Pro Glu Leu Glu Glu Glu
            130                 135                 140

Leu Glu Ala Asp His Thr Pro His Tyr Pro Glu Gln Glu Thr Glu Pro
145                 150                 155                 160

Pro Leu Gly Ser Cys Ser Asp Val Met Leu Ser Val Glu Glu Glu Gly
                165                 170                 175

Lys Glu Asp Pro Leu Pro Thr Ala Ala Ser Gly Lys
            180                 185

<210> SEQ ID NO 12
<211> LENGTH: 58
<212> TYPE: PRT
<213> ORGANISM: Artificial Sequence
<220> FEATURE:
<223> OTHER INFORMATION: GITR endodomain

<400> SEQUENCE: 12

Gln Leu Gly Leu His Ile Trp Gln Leu Arg Ser Gln Cys Met Trp Pro
1               5                   10                  15

Arg Glu Thr Gln Leu Leu Leu Glu Val Pro Pro Ser Thr Glu Asp Ala
            20                  25                  30

Arg Ser Cys Gln Phe Pro Glu Glu Glu Arg Gly Glu Arg Ser Ala Glu
        35                  40                  45

Glu Lys Gly Arg Leu Gly Asp Leu Trp Val
    50                  55

<210> SEQ ID NO 13
<211> LENGTH: 60
<212> TYPE: PRT
<213> ORGANISM: Artificial Sequence
<220> FEATURE:
<223> OTHER INFORMATION: HVEM endodomain

<400> SEQUENCE: 13

Cys Val Lys Arg Arg Lys Pro Arg Gly Asp Val Val Lys Val Ile Val
1               5                   10                  15

Ser Val Gln Arg Lys Arg Gln Glu Ala Glu Gly Glu Ala Thr Val Ile
            20                  25                  30

Glu Ala Leu Gln Ala Pro Pro Asp Val Thr Thr Val Ala Val Glu Glu
        35                  40                  45

Thr Ile Pro Ser Phe Thr Gly Arg Ser Pro Asn His
    50                  55                  60

<210> SEQ ID NO 14
<211> LENGTH: 20
<212> TYPE: PRT
<213> ORGANISM: Artificial Sequence
```

<220> FEATURE:
<223> OTHER INFORMATION: 2A-like sequence

<400> SEQUENCE: 14

Tyr His Ala Asp Tyr Tyr Lys Gln Arg Leu Ile His Asp Val Glu Met
1               5                   10                  15

Asn Pro Gly Pro
            20

<210> SEQ ID NO 15
<211> LENGTH: 20
<212> TYPE: PRT
<213> ORGANISM: Artificial Sequence
<220> FEATURE:
<223> OTHER INFORMATION: 2A-like sequence

<400> SEQUENCE: 15

His Tyr Ala Gly Tyr Phe Ala Asp Leu Leu Ile His Asp Ile Glu Thr
1               5                   10                  15

Asn Pro Gly Pro
            20

<210> SEQ ID NO 16
<211> LENGTH: 20
<212> TYPE: PRT
<213> ORGANISM: Artificial Sequence
<220> FEATURE:
<223> OTHER INFORMATION: 2A-like sequence

<400> SEQUENCE: 16

Gln Cys Thr Asn Tyr Ala Leu Leu Lys Leu Ala Gly Asp Val Glu Ser
1               5                   10                  15

Asn Pro Gly Pro
            20

<210> SEQ ID NO 17
<211> LENGTH: 19
<212> TYPE: PRT
<213> ORGANISM: Artificial Sequence
<220> FEATURE:
<223> OTHER INFORMATION: 2A-like sequence

<400> SEQUENCE: 17

Ala Thr Asn Phe Ser Leu Leu Lys Gln Ala Gly Asp Val Glu Glu Asn
1               5                   10                  15

Pro Gly Pro

<210> SEQ ID NO 18
<211> LENGTH: 19
<212> TYPE: PRT
<213> ORGANISM: Artificial Sequence
<220> FEATURE:
<223> OTHER INFORMATION: 2A-like sequence

<400> SEQUENCE: 18

Ala Ala Arg Gln Met Leu Leu Leu Leu Ser Gly Asp Val Glu Thr Asn
1               5                   10                  15

Pro Gly Pro

<210> SEQ ID NO 19
<211> LENGTH: 20
<212> TYPE: PRT
<213> ORGANISM: Artificial Sequence
<220> FEATURE:

<223> OTHER INFORMATION: 2A-like sequence

<400> SEQUENCE: 19

Arg Ala Glu Gly Arg Gly Ser Leu Leu Thr Cys Gly Asp Val Glu Glu
1               5                   10                  15

Asn Pro Gly Pro
            20

<210> SEQ ID NO 20
<211> LENGTH: 20
<212> TYPE: PRT
<213> ORGANISM: Artificial Sequence
<220> FEATURE:
<223> OTHER INFORMATION: 2A-like sequence

<400> SEQUENCE: 20

Thr Arg Ala Glu Ile Glu Asp Glu Leu Ile Arg Ala Gly Ile Glu Ser
1               5                   10                  15

Asn Pro Gly Pro
            20

<210> SEQ ID NO 21
<211> LENGTH: 20
<212> TYPE: PRT
<213> ORGANISM: Artificial Sequence
<220> FEATURE:
<223> OTHER INFORMATION: 2A-like sequence

<400> SEQUENCE: 21

Thr Arg Ala Glu Ile Glu Asp Glu Leu Ile Arg Ala Asp Ile Glu Ser
1               5                   10                  15

Asn Pro Gly Pro
            20

<210> SEQ ID NO 22
<211> LENGTH: 20
<212> TYPE: PRT
<213> ORGANISM: Artificial Sequence
<220> FEATURE:
<223> OTHER INFORMATION: 2A-like sequence

<400> SEQUENCE: 22

Ala Lys Phe Gln Ile Asp Lys Ile Leu Ile Ser Gly Asp Val Glu Leu
1               5                   10                  15

Asn Pro Gly Pro
            20

<210> SEQ ID NO 23
<211> LENGTH: 20
<212> TYPE: PRT
<213> ORGANISM: Artificial Sequence
<220> FEATURE:
<223> OTHER INFORMATION: 2A-like sequence

<400> SEQUENCE: 23

Ser Ser Ile Ile Arg Thr Lys Met Leu Val Ser Gly Asp Val Glu Glu
1               5                   10                  15

Asn Pro Gly Pro
            20

<210> SEQ ID NO 24
<211> LENGTH: 20
<212> TYPE: PRT
<213> ORGANISM: Artificial Sequence

```
<220> FEATURE:
<223> OTHER INFORMATION: 2A-like sequence

<400> SEQUENCE: 24

Cys Asp Ala Gln Arg Gln Lys Leu Leu Leu Ser Gly Asp Ile Glu Gln
1               5                   10                  15

Asn Pro Gly Pro
            20

<210> SEQ ID NO 25
<211> LENGTH: 20
<212> TYPE: PRT
<213> ORGANISM: Artificial Sequence
<220> FEATURE:
<223> OTHER INFORMATION: 2A-like sequence

<400> SEQUENCE: 25

Tyr Pro Ile Asp Phe Gly Gly Phe Leu Val Lys Ala Asp Ser Glu Phe
1               5                   10                  15

Asn Pro Gly Pro
            20

<210> SEQ ID NO 26
<211> LENGTH: 647
<212> TYPE: PRT
<213> ORGANISM: Artificial Sequence
<220> FEATURE:
<223> OTHER INFORMATION: amino acid sequence of the ORF of the anti-CD33
      COMP CAR

<400> SEQUENCE: 26

Met Gly Thr Ser Leu Leu Cys Trp Met Ala Leu Cys Leu Leu Gly Ala
1               5                   10                  15

Asp His Ala Asp Ala Cys Pro Tyr Ser Asn Pro Ser Leu Cys Ser Gly
            20                  25                  30

Gly Gly Gly Ser Glu Leu Pro Thr Gln Gly Thr Phe Ser Asn Val Ser
        35                  40                  45

Thr Asn Val Ser Pro Ala Lys Pro Thr Thr Thr Ala Cys Pro Tyr Ser
    50                  55                  60

Asn Pro Ser Leu Cys Ser Gly Gly Gly Ser Pro Ala Pro Arg Pro
65                  70                  75                  80

Pro Thr Pro Ala Pro Thr Ile Ala Ser Gln Pro Leu Ser Leu Arg Pro
                85                  90                  95

Glu Ala Cys Arg Pro Ala Ala Gly Gly Ala Val His Thr Arg Gly Leu
            100                 105                 110

Asp Phe Ala Cys Asp Ile Tyr Ile Trp Ala Pro Leu Ala Gly Thr Cys
        115                 120                 125

Gly Val Leu Leu Leu Ser Leu Val Ile Thr Leu Tyr Cys Asn His Arg
    130                 135                 140

Asn Arg Arg Arg Val Cys Lys Cys Pro Arg Pro Val Val Arg Ala Glu
145                 150                 155                 160

Gly Arg Gly Ser Leu Leu Thr Cys Gly Asp Val Glu Glu Asn Pro Gly
                165                 170                 175

Pro Met Ala Val Pro Thr Gln Val Leu Gly Leu Leu Leu Leu Trp Leu
            180                 185                 190

Thr Asp Ala Arg Cys Asp Ile Gln Met Thr Gln Ser Pro Ser Ser Leu
        195                 200                 205

Ser Ala Ser Val Gly Asp Arg Val Thr Ile Thr Cys Arg Ala Ser Glu
    210                 215                 220
```

-continued

Asp Ile Tyr Phe Asn Leu Val Trp Tyr Gln Gln Lys Pro Gly Lys Ala
225                 230                 235                 240

Pro Lys Leu Leu Ile Tyr Asp Thr Asn Arg Leu Ala Asp Gly Val Pro
            245                 250                 255

Ser Arg Phe Ser Gly Ser Gly Ser Gly Thr Gln Tyr Thr Leu Thr Ile
        260                 265                 270

Ser Ser Leu Gln Pro Glu Asp Phe Ala Thr Tyr Tyr Cys Gln His Tyr
    275                 280                 285

Lys Asn Tyr Pro Leu Thr Phe Gly Gln Gly Thr Lys Leu Glu Ile Lys
290                 295                 300

Arg Ser Gly Gly Gly Gly Ser Gly Gly Gly Gly Ser Gly Gly Gly Gly
305                 310                 315                 320

Ser Gly Gly Gly Gly Ser Arg Ser Glu Val Gln Leu Val Glu Ser Gly
                325                 330                 335

Gly Gly Leu Val Gln Pro Gly Gly Ser Leu Arg Leu Ser Cys Ala Ala
            340                 345                 350

Ser Gly Phe Thr Leu Ser Asn Tyr Gly Met His Trp Ile Arg Gln Ala
        355                 360                 365

Pro Gly Lys Gly Leu Glu Trp Val Ser Ser Ile Ser Leu Asn Gly Gly
    370                 375                 380

Ser Thr Tyr Tyr Arg Asp Ser Val Lys Gly Arg Phe Thr Ile Ser Arg
385                 390                 395                 400

Asp Asn Ala Lys Ser Thr Leu Tyr Leu Gln Met Asn Ser Leu Arg Ala
                405                 410                 415

Glu Asp Thr Ala Val Tyr Tyr Cys Ala Ala Gln Asp Ala Tyr Thr Gly
            420                 425                 430

Gly Tyr Phe Asp Tyr Trp Gly Gln Gly Thr Leu Val Thr Val Ser Ser
        435                 440                 445

Met Asp Pro Ala Gly Ser Asp Leu Gly Pro Gln Met Leu Arg Glu Leu
    450                 455                 460

Gln Glu Thr Asn Ala Ala Leu Gln Asp Val Arg Glu Leu Leu Arg Gln
465                 470                 475                 480

Gln Val Arg Glu Ile Thr Phe Leu Lys Asn Thr Val Met Glu Cys Asp
                485                 490                 495

Ala Cys Gly Ser Gly Lys Lys Asp Pro Lys Phe Trp Val Leu Val Val
            500                 505                 510

Val Gly Gly Val Leu Ala Cys Tyr Ser Leu Leu Val Thr Val Ala Phe
        515                 520                 525

Ile Ile Phe Trp Val Arg Ser Arg Val Lys Phe Ser Arg Ser Ala Asp
    530                 535                 540

Ala Pro Ala Tyr Gln Gln Gly Gln Asn Gln Leu Tyr Asn Glu Leu Asn
545                 550                 555                 560

Leu Gly Arg Arg Glu Glu Tyr Asp Val Leu Asp Lys Arg Arg Gly Arg
                565                 570                 575

Asp Pro Glu Met Gly Gly Lys Pro Arg Arg Lys Asn Pro Gln Glu Gly
            580                 585                 590

Leu Tyr Asn Glu Leu Gln Lys Asp Lys Met Ala Glu Ala Tyr Ser Glu
        595                 600                 605

Ile Gly Met Lys Gly Glu Arg Arg Gly Lys Gly His Asp Gly Leu
    610                 615                 620

Tyr Gln Gly Leu Ser Thr Ala Thr Lys Asp Thr Tyr Asp Ala Leu His
625                 630                 635                 640

Met Gln Ala Leu Pro Pro Arg
            645

<210> SEQ ID NO 27
<211> LENGTH: 638
<212> TYPE: PRT
<213> ORGANISM: Artificial Sequence
<220> FEATURE:
<223> OTHER INFORMATION: amino acid sequence of the ORF of the
      anti-ROR-1 COMP CAR

<400> SEQUENCE: 27

Met Gly Thr Ser Leu Leu Cys Trp Met Ala Leu Cys Leu Leu Gly Ala
1               5                   10                  15

Asp His Ala Asp Ala Cys Pro Tyr Ser Asn Pro Ser Leu Cys Ser Gly
            20                  25                  30

Gly Gly Gly Ser Glu Leu Pro Thr Gln Gly Thr Phe Ser Asn Val Ser
        35                  40                  45

Thr Asn Val Ser Pro Ala Lys Pro Thr Thr Ala Cys Pro Tyr Ser
    50                  55                  60

Asn Pro Ser Leu Cys Ser Gly Gly Gly Ser Pro Ala Pro Arg Pro
65                  70                  75                  80

Pro Thr Pro Ala Pro Thr Ile Ala Ser Gln Pro Leu Ser Leu Arg Pro
                85                  90                  95

Glu Ala Cys Arg Pro Ala Ala Gly Gly Ala Val His Thr Arg Gly Leu
            100                 105                 110

Asp Phe Ala Cys Asp Ile Tyr Ile Trp Ala Pro Leu Ala Gly Thr Cys
        115                 120                 125

Gly Val Leu Leu Leu Ser Leu Val Ile Thr Leu Tyr Cys Asn His Arg
    130                 135                 140

Asn Arg Arg Val Cys Lys Cys Pro Arg Pro Val Val Arg Ala Glu
145                 150                 155                 160

Gly Arg Gly Ser Leu Leu Thr Cys Gly Asp Val Glu Glu Asn Pro Gly
                165                 170                 175

Pro Met Glu Thr Asp Thr Leu Leu Leu Trp Val Leu Leu Leu Trp Val
            180                 185                 190

Pro Gly Ser Thr Gly Gln Ser Val Lys Glu Ser Glu Gly Asp Leu Val
        195                 200                 205

Thr Pro Ala Gly Asn Leu Thr Leu Thr Cys Thr Ala Ser Gly Ser Asp
    210                 215                 220

Ile Asn Asp Tyr Pro Ile Ser Trp Val Arg Gln Ala Pro Gly Lys Gly
225                 230                 235                 240

Leu Glu Trp Ile Gly Phe Ile Asn Ser Gly Gly Ser Thr Trp Tyr Ala
                245                 250                 255

Ser Trp Val Lys Gly Arg Phe Thr Ile Ser Arg Thr Ser Thr Thr Val
            260                 265                 270

Asp Leu Lys Met Thr Ser Leu Thr Thr Asp Asp Thr Ala Thr Tyr Phe
        275                 280                 285

Cys Ala Arg Gly Tyr Ser Thr Tyr Tyr Gly Asp Phe Asn Ile Trp Gly
    290                 295                 300

Pro Gly Thr Leu Val Thr Ile Ser Ser Gly Gly Gly Gly Ser Gly Gly
305                 310                 315                 320

Gly Gly Ser Gly Gly Gly Gly Ser Glu Leu Val Met Thr Gln Thr Pro
                325                 330                 335

Ser Ser Thr Ser Gly Ala Val Gly Gly Thr Val Thr Ile Asn Cys Gln
            340                 345                 350

Ala Ser Gln Ser Ile Asp Ser Asn Leu Ala Trp Phe Gln Gln Lys Pro
            355                 360                 365

Gly Gln Pro Pro Thr Leu Leu Ile Tyr Arg Ala Ser Asn Leu Ala Ser
        370                 375                 380

Gly Val Pro Ser Arg Phe Ser Gly Ser Arg Ser Gly Thr Glu Tyr Thr
385                 390                 395                 400

Leu Thr Ile Ser Gly Val Gln Arg Glu Asp Ala Ala Thr Tyr Tyr Cys
                405                 410                 415

Leu Gly Gly Val Gly Asn Val Ser Tyr Arg Thr Ser Phe Gly Gly Gly
                420                 425                 430

Thr Glu Val Val Val Lys Arg Ser Asp Pro Ala Gly Ser Asp Leu Gly
            435                 440                 445

Pro Gln Met Leu Arg Glu Leu Gln Glu Thr Asn Ala Ala Leu Gln Asp
        450                 455                 460

Val Arg Glu Leu Leu Arg Gln Gln Val Arg Glu Ile Thr Phe Leu Lys
465                 470                 475                 480

Asn Thr Val Met Glu Cys Asp Ala Cys Gly Ser Gly Lys Lys Asp Pro
                485                 490                 495

Lys Phe Trp Val Leu Val Val Val Gly Gly Val Leu Ala Cys Tyr Ser
            500                 505                 510

Leu Leu Val Thr Val Ala Phe Ile Ile Phe Trp Val Arg Ser Arg Val
        515                 520                 525

Lys Phe Ser Arg Ser Ala Asp Ala Pro Ala Tyr Gln Gln Gly Gln Asn
530                 535                 540

Gln Leu Tyr Asn Glu Leu Asn Leu Gly Arg Arg Glu Glu Tyr Asp Val
545                 550                 555                 560

Leu Asp Lys Arg Arg Gly Arg Asp Pro Glu Met Gly Gly Lys Pro Arg
                565                 570                 575

Arg Lys Asn Pro Gln Glu Gly Leu Tyr Asn Glu Leu Gln Lys Asp Lys
            580                 585                 590

Met Ala Glu Ala Tyr Ser Glu Ile Gly Met Lys Gly Glu Arg Arg Arg
        595                 600                 605

Gly Lys Gly His Asp Gly Leu Tyr Gln Gly Leu Ser Thr Ala Thr Lys
            610                 615                 620

Asp Thr Tyr Asp Ala Leu His Met Gln Ala Leu Pro Pro Arg
625                 630                 635

<210> SEQ ID NO 28
<211> LENGTH: 1944
<212> TYPE: DNA
<213> ORGANISM: Artificial Sequence
<220> FEATURE:
<223> OTHER INFORMATION: DNA sequence of the ORF of the anti-CD33 COMP
      CAR

<400> SEQUENCE: 28
atgggcacca gcctgctgtg ctggatggcc ctgtgcctgc tgggcgccga ccacgccgat    60
gcctgcccct acagcaaccc cagcctgtgc agcggaggcg gcggcagcga gctgcccacc   120
cagggcacct tctccaacgt gtccaccaac gtgagcccag ccaagcccac caccaccgcc   180
tgtccttatt ccaatccttc cctgtgtagc ggaggggag gcagcccagc ccccagacct   240
cccaccccag cccccaccat cgccagccag cctctgagcc tgagaccga ggcctgccgc   300 ccagccgccg cggcgccgt gcacaccaga ggcctggatt cgcctgcga tatctacatc   360 tgggcccac tggccggcac ctgtggcgtg ctgctgctga gcctggtgat caccctgtac   420

```
tgcaaccacc gcaaccgcag gcgcgtgtgc aagtgcccca ggcccgtggt gagagccgag    480
ggcagaggca gcctgctgac ctgcggcgac gtggaggaga cccaggccc catggccgtg     540 cccactcagg tcctggggtt gttgctactg tggcttacag atgccagatg tgacatccag    600
atgacacagt ctccatcttc cctgtctgca tctgtcggag atcgcgtcac catcacctgt    660
cgagcaagtg aggacattta ttttaattta gtgtggtatc agcagaaacc aggaaaggcc    720
cctaagctcc tgatctatga tacaaatcgc ttggcagatg gggtcccatc acggttcagt    780
ggctctggat ctggcacaca gtatactcta accataagta gcctgcaacc gaagatttc    840 gcaacctatt attgtcaaca ctataagaat tatccgctca cgttcggtca ggggaccaag    900
ctggaaatca aagatctgg tggcggaggg tcaggaggcg gaggcagcgg aggcggtggc    960
tcgggaggcg gaggctcgag atctgaggtg cagttggtgg agtctggggg cggcttggtg    1020
cagcctggag ggtccctgag gctctcctgt gcagcctcag gattcactct cagtaattat    1080
ggcatgcact ggatcaggca ggctccaggg aagggtctgg agtgggtctc gtctattagt    1140
cttaatggtg gtagcactta ctatcgagac tccgtgaagg gccgattcac tatctccagg    1200
gacaatgcaa aaagcaccct ctaccttcaa atgaatagtc tgagggccga ggacacggcc    1260
gtctattact gtgcagcaca ggacgcttat acgggaggtt actttgatta ctggggccaa    1320
ggaacgctgg tcacagtctc gtctatggat cccgccggga gcgacctggg ccctcagatg    1380
ctgcgggagc tgcaggagac aaatgccgcc ctgcaggacg tgcgcgagct gctgagacag    1440
caggtgcggg agattacatt cctgaagaac accgtgatgg agtgcgatgc ctgcggatct    1500
gggaagaagg accccaagtt ctgggtcctg gtggtggtgg gaggcgtgct ggcctgttac    1560
tctctcctgg tgaccgtggc cttcatcatc ttttgggtgc gctcccgggt gaagttttct    1620
cgctctgccg atgccccagc ctatcagcag ggccagaatc agctgtacaa tgaactgaac    1680
ctgggcaggc gggaggagta cgacgtgctg gataagcgga gaggcagaga ccccgagatg    1740
ggcggcaaac acggcgcaa aaatccccag gagggactct ataacgagct gcagaaggac    1800
aaaatggccg aggcctattc cgagatcggc atgaagggag agagaagacg cggaaagggc    1860
cacgacggcc tgtatcaggg attgtccacc gctacaaaag atacatatga tgccctgcac    1920
atgcaggccc tgccacccag atga                                          1944
```

<210> SEQ ID NO 29
<211> LENGTH: 1914
<212> TYPE: DNA
<213> ORGANISM: Artificial Sequence
<220> FEATURE:
<223> OTHER INFORMATION: DNA sequence of the ORF of the anti-ROR-1 COMP CAR

<400> SEQUENCE: 29

```
atgggcacca gcctgctgtg ctggatggcc ctgtgcctgc tgggcgccga ccacgccgat    60
gcctgcccct acagcaaccc cagcctgtgc agcggaggcg gcggcagcga gctgcccacc    120
cagggcacct tctccaacgt gtccaccaac gtgagcccag ccaagcccac caccaccgcc    180
tgtcctattt ccaatcctc cctgtgtagc ggaggggag gcagcccagc ccccagacct    240 cccacccag cccccaccat cgccagccag cctctgagcc tgagacccga ggcctgccgc    300
ccagccgccg cggcgccgt gcacaccaga ggcctggatt tcgcctgcga tatctacatc    360 tgggcccac tggccggcac ctgtggcgtg ctgctgctga gcctggtgat caccctgtac    420
tgcaaccacc gcaaccgcag gcgcgtgtgc aagtgcccca ggcccgtggt gagagccgag    480
```

```
ggcagaggca gcctgctgac ctgcggcgac gtggaggaga acccaggccc catgagacc     540 gacaccctgc tgctgtgggt gctgctgctg tgggtgcccg gcagcaccgg ccagagcgtg    600
aaggagagcg agggcgacct ggtgacccca gccggcaacc tgaccctgac ctgcaccgcc    660
agcggcagcg acatcaacga ctaccccatc agctgggtgc ggcaggcccc aggcaagggc    720
ctggagtgga tcggcttcat caacagcggc ggcagcacct ggtacgccag ctgggtgaag    780
ggccggttca ccatcagccg gaccagcacc accgtggacc tgaagatgac cagcctgacc    840
accgacgaca ccgccaccta cttctgcgcc agaggctaca gcacctacta cggcgacttc    900
aacatctggg gaccggcac cctggtgacc atcagcagcg gaggcggagg gtctgggggc      960
ggcggtagcg gcggaggagg gagcgagctg gtgatgaccc agaccccaag cagcaccagc    1020
ggcgccgtgg gcggcaccgt gaccatcaac tgccaggcca gcagagcat cgacagcaac    1080 ctggcctggt ccagcagaa gcctggccag ccacccaccc tgctgatcta ccgggccagc    1140
aacctggcca gcggcgtgcc cagccggttc agcggcagcc ggagcggcac cgagtacacc    1200
ctgaccatca gcggcgtgca gcgggaggac gccgccacct actactgcct gggcggagtg    1260
ggcaacgtga gctaccggac cagcttcggc ggaggcaccg aggtggtggt gaagcggtcg    1320
gatcccgccg ggagcgacct gggccctcag atgctgcggg agctgcagga gacaaatgcc    1380
gccctgcagg acgtgcgcga gctgctgaga cagcaggtgc gggagattac attcctgaag    1440
aacaccgtga tggagtgcga tgcctgcgga tctgggaaga aggaccccaa gttctgggtc    1500
ctggtggtgg tgggaggcgt gctggcctgt tactctctcc tggtgaccgt ggccttcatc    1560
atcttttggg tgcgctcccg ggtgaagttt tctcgctctg ccgatgcccc agcctatcag    1620
cagggccaga tcagctgta caatgaactg aacctgggca ggcgggagga gtacgacgtg    1680
ctggataagc ggagaggcag agaccccgag atgggcggca accacggcg caaaaatccc    1740 caggagggac tctataacga gctgcagaag gacaaaatgg ccgaggccta ttccgagatc    1800
ggcatgaagg gagagagaag acgcggaaag ggccacgacg gcctgtatca gggattgtcc    1860
accgctacaa aagatacata tgatgccctg cacatgcagg ccctgccacc caga          1914
```

<210> SEQ ID NO 30
<211> LENGTH: 57
<212> TYPE: PRT
<213> ORGANISM: Artificial Sequence
<220> FEATURE:
<223> OTHER INFORMATION: Kinesin motor protein: parallel homodimer

<400> SEQUENCE: 30

Met His Ala Ala Leu Ser Thr Glu Val Val His Leu Arg Gln Arg Thr
1               5                   10                  15

Glu Glu Leu Leu Arg Cys Asn Glu Gln Gln Ala Ala Glu Leu Glu Thr
            20                  25                  30

Cys Lys Glu Gln Leu Phe Gln Ser Asn Met Glu Arg Lys Glu Leu His
        35                  40                  45

Asn Thr Val Met Asp Leu Arg Gly Asn
    50                  55

<210> SEQ ID NO 31
<211> LENGTH: 50
<212> TYPE: PRT
<213> ORGANISM: Artificial Sequence
<220> FEATURE:
<223> OTHER INFORMATION: Hepatitis D delta antigen: parallel homodimer

<400> SEQUENCE: 31

Gly Arg Glu Asp Ile Leu Glu Gln Trp Val Ser Gly Arg Lys Lys Leu
1               5                   10                  15

Glu Glu Leu Glu Arg Asp Leu Arg Lys Leu Lys Lys Ile Lys Lys
            20                  25                  30

Leu Glu Asp Asn Pro Trp Leu Gly Asn Ile Lys Gly Ile Ile Gly
        35                  40                  45

Lys Tyr
    50

<210> SEQ ID NO 32
<211> LENGTH: 61
<212> TYPE: PRT
<213> ORGANISM: Artificial Sequence
<220> FEATURE:
<223> OTHER INFORMATION: Archaeal box C/D sRNP core protein: anti-
      parallel heterodimer

<400> SEQUENCE: 32

Arg Tyr Val Val Ala Leu Val Lys Ala Leu Glu Glu Ile Asp Glu Ser
1               5                   10                  15

Ile Asn Met Leu Asn Glu Lys Leu Glu Asp Ile Arg Ala Val Lys Glu
            20                  25                  30

Ser Glu Ile Thr Glu Lys Phe Glu Lys Lys Ile Arg Glu Leu Arg Glu
        35                  40                  45

Leu Arg Arg Asp Val Glu Arg Glu Ile Glu Glu Val Met
    50                  55                  60

<210> SEQ ID NO 33
<211> LENGTH: 31
<212> TYPE: PRT
<213> ORGANISM: Artificial Sequence
<220> FEATURE:
<223> OTHER INFORMATION: Mannose-binding protein A: parallel homotrimer

<400> SEQUENCE: 33

Ala Ile Glu Val Lys Leu Ala Asn Met Glu Ala Glu Ile Asn Thr Leu
1               5                   10                  15

Lys Ser Lys Leu Glu Leu Thr Asn Lys Leu His Ala Phe Ser Met
            20                  25                  30

<210> SEQ ID NO 34
<211> LENGTH: 29
<212> TYPE: PRT
<213> ORGANISM: Artificial Sequence
<220> FEATURE:
<223> OTHER INFORMATION: Coiled-coil serine-rich protein 1: parallel
      homotrimer

<400> SEQUENCE: 34

Glu Trp Glu Ala Leu Glu Lys Lys Leu Ala Ala Leu Glu Ser Lys Leu
1               5                   10                  15

Gln Ala Leu Glu Lys Lys Leu Glu Ala Leu Glu His Gly
            20                  25

<210> SEQ ID NO 35
<211> LENGTH: 24
<212> TYPE: PRT
<213> ORGANISM: Artificial Sequence
<220> FEATURE:
<223> OTHER INFORMATION: Polypeptide release factor 2: anti-parallel
      heterotrimer Chain A

```
<400> SEQUENCE: 35

Ile Asn Pro Val Asn Asn Arg Ile Gln Asp Leu Thr Glu Arg Ser Asp
1               5                   10                  15

Val Leu Arg Gly Tyr Leu Asp Tyr
            20

<210> SEQ ID NO 36
<211> LENGTH: 51
<212> TYPE: PRT
<213> ORGANISM: Artificial Sequence
<220> FEATURE:
<223> OTHER INFORMATION: Polypeptide release factor 2: anti-parallel
      heterotrimer Chain B

<400> SEQUENCE: 36

Val Val Asp Thr Leu Asp Gln Met Lys Gln Gly Leu Glu Asp Val Ser
1               5                   10                  15

Gly Leu Leu Glu Leu Ala Val Glu Ala Asp Asp Glu Glu Thr Phe Asn
            20                  25                  30

Glu Ala Val Ala Glu Leu Asp Ala Leu Glu Glu Lys Leu Ala Gln Leu
        35                  40                  45

Glu Phe Arg
    50

<210> SEQ ID NO 37
<211> LENGTH: 51
<212> TYPE: PRT
<213> ORGANISM: Artificial Sequence
<220> FEATURE:
<223> OTHER INFORMATION: SNAP-25 and SNARE: parallel heterotetramer
      Chain A

<400> SEQUENCE: 37

Ile Glu Thr Arg His Ser Glu Ile Ile Lys Leu Glu Asn Ser Ile Arg
1               5                   10                  15

Glu Leu His Asp Met Phe Met Asp Met Ala Met Leu Val Glu Ser Gln
            20                  25                  30

Gly Glu Met Ile Asp Arg Ile Glu Tyr Asn Val Glu His Ala Val Asp
        35                  40                  45

Tyr Val Glu
    50

<210> SEQ ID NO 38
<211> LENGTH: 67
<212> TYPE: PRT
<213> ORGANISM: Artificial Sequence
<220> FEATURE:
<223> OTHER INFORMATION: SNAP-25 and SNARE: parallel heterotetramer
      Chain B

<400> SEQUENCE: 38

Ala Leu Ser Glu Ile Glu Thr Arg His Ser Glu Ile Ile Lys Leu Glu
1               5                   10                  15

Asn Ser Ile Arg Glu Leu His Asp Met Phe Met Asp Met Ala Met Leu
            20                  25                  30

Val Glu Ser Gln Gly Glu Met Ile Asp Arg Ile Glu Tyr Asn Val Glu
        35                  40                  45

His Ala Val Asp Tyr Val Glu Arg Ala Val Ser Asp Thr Lys Lys Ala
    50                  55                  60

Val Lys Tyr
65
```

```
<210> SEQ ID NO 39
<211> LENGTH: 69
<212> TYPE: PRT
<213> ORGANISM: Artificial Sequence
<220> FEATURE:
<223> OTHER INFORMATION: SNAP-25 and SNARE: parallel heterotetramer
      Chain C

<400> SEQUENCE: 39

Glu Leu Glu Glu Met Gln Arg Arg Ala Asp Gln Leu Ala Asp Glu Ser
1               5                   10                  15

Leu Glu Ser Thr Arg Arg Met Leu Gln Leu Val Glu Glu Ser Lys Asp
            20                  25                  30

Ala Gly Ile Arg Thr Leu Val Met Leu Asp Glu Gln Gly Glu Gln Leu
        35                  40                  45

Glu Arg Ile Glu Glu Gly Met Asp Gln Ile Asn Lys Asp Met Lys Glu
    50                  55                  60

Ala Glu Lys Asn Leu
65

<210> SEQ ID NO 40
<211> LENGTH: 51
<212> TYPE: PRT
<213> ORGANISM: Artificial Sequence
<220> FEATURE:
<223> OTHER INFORMATION: SNAP-25 and SNARE: parallel heterotetramer
      Chain D

<400> SEQUENCE: 40

Ile Glu Thr Arg His Ser Glu Ile Ile Lys Leu Glu Asn Ser Ile Arg
1               5                   10                  15

Glu Leu His Asp Met Phe Met Asp Met Ala Met Leu Val Glu Ser Gln
            20                  25                  30

Gly Glu Met Ile Asp Arg Ile Glu Tyr Asn Val Glu His Ala Val Asp
        35                  40                  45

Tyr Val Glu
    50

<210> SEQ ID NO 41
<211> LENGTH: 20
<212> TYPE: PRT
<213> ORGANISM: Artificial Sequence
<220> FEATURE:
<223> OTHER INFORMATION: Lac repressor: parallel homotetramer

<400> SEQUENCE: 41

Ser Pro Arg Ala Leu Ala Asp Ser Leu Met Gln Leu Ala Arg Gln Val
1               5                   10                  15

Ser Arg Leu Glu
            20

<210> SEQ ID NO 42
<211> LENGTH: 136
<212> TYPE: PRT
<213> ORGANISM: Artificial Sequence
<220> FEATURE:
<223> OTHER INFORMATION: Apolipoprotein E: anti-parallel heterotetramer

<400> SEQUENCE: 42

Ser Gly Gln Arg Trp Glu Leu Ala Leu Gly Arg Phe Trp Asp Tyr Leu
1               5                   10                  15
```

```
Arg Trp Val Gln Thr Leu Ser Glu Gln Val Gln Glu Glu Leu Leu Ser
            20                  25                  30

Ser Gln Val Thr Gln Glu Leu Arg Ala Leu Met Asp Glu Thr Met Lys
                35                  40                  45

Glu Leu Lys Ala Tyr Lys Ser Glu Leu Glu Glu Gln Leu Thr Ala Arg
    50                  55                  60

Leu Ser Lys Glu Leu Gln Ala Ala Gln Ala Arg Leu Gly Ala Asp Met
65                  70                  75                  80

Glu Asp Val Cys Gly Arg Leu Val Gln Tyr Arg Gly Glu Val Gln Ala
                85                  90                  95

Met Leu Gly Gln Ser Thr Glu Glu Leu Arg Val Arg Leu Ala Ser His
            100                 105                 110

Leu Arg Lys Leu Arg Lys Arg Leu Leu Arg Asp Ala Asp Asp Leu Gln
        115                 120                 125

Lys Arg Leu Ala Val Tyr Gln Ala
    130                 135

<210> SEQ ID NO 43
<211> LENGTH: 29
<212> TYPE: PRT
<213> ORGANISM: Artificial Sequence
<220> FEATURE:
<223> OTHER INFORMATION: heterodimerization domain

<400> SEQUENCE: 43

Gln Leu Glu Lys Glu Leu Gln Ala Leu Glu Lys Glu Asn Ala Gln Leu
1               5                   10                  15

Glu Trp Glu Leu Gln Ala Leu Glu Lys Glu Leu Ala Gln
            20                  25

<210> SEQ ID NO 44
<211> LENGTH: 29
<212> TYPE: PRT
<213> ORGANISM: Artificial Sequence
<220> FEATURE:
<223> OTHER INFORMATION: heterodimerization domain

<400> SEQUENCE: 44

Gln Leu Glu Lys Lys Leu Gln Ala Leu Lys Lys Lys Asn Ala Gln Leu
1               5                   10                  15

Lys Trp Lys Leu Gln Ala Leu Lys Lys Lys Leu Ala Gln
            20                  25

<210> SEQ ID NO 45
<211> LENGTH: 44
<212> TYPE: PRT
<213> ORGANISM: Artificial Sequence
<220> FEATURE:
<223> OTHER INFORMATION: dimerization and docking domain (DDD1)

<400> SEQUENCE: 45

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
            35                  40

<210> SEQ ID NO 46
<211> LENGTH: 18
<212> TYPE: PRT
```

```
<213> ORGANISM: Artificial Sequence
<220> FEATURE:
<223> OTHER INFORMATION: anchoring domain (AD1)

<400> SEQUENCE: 46

Val Gln Ile Glu Tyr Leu Ala Lys Gln Ile Val Asp Asn Ala Ile Gln
1               5                   10                  15

Gln Ala

<210> SEQ ID NO 47
<211> LENGTH: 20
<212> TYPE: PRT
<213> ORGANISM: Artificial Sequence
<220> FEATURE:
<223> OTHER INFORMATION: truncated COMP

<400> SEQUENCE: 47

Gln Gln Val Arg Glu Ile Thr Phe Leu Lys Asn Thr Val Met Glu Cys
1               5                   10                  15

Asp Ala Cys Gly
            20

<210> SEQ ID NO 48
<211> LENGTH: 7
<212> TYPE: PRT
<213> ORGANISM: Artificial Sequence
<220> FEATURE:
<223> OTHER INFORMATION: consensus Tobacco Etch Virus (TEV) cleavage
      site

<400> SEQUENCE: 48

Glu Asn Leu Tyr Phe Gln Ser
1               5

<210> SEQ ID NO 49
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 49

Cys Asp Ala Cys Gly
1               5
```